US010752965B2

(12) United States Patent
Chen

(10) Patent No.: US 10,752,965 B2
(45) Date of Patent: Aug. 25, 2020

(54) CLEAVABLE NUCLEIC ACID LINKERS FOR PROTEIN QUANTIFICATION RATIOING

(71) Applicant: Brian Chen, Brossard (CA)

(72) Inventor: Brian Chen, Brossard (CA)

(*) Notice: Subject to any disclaimer, the term of this patent is extended or adjusted under 35 U.S.C. 154(b) by 217 days.

(21) Appl. No.: 15/534,025

(22) PCT Filed: Dec. 7, 2015

(86) PCT No.: PCT/CA2015/051281
§ 371 (c)(1),
(2) Date: Jun. 8, 2017

(87) PCT Pub. No.: WO2016/090470
PCT Pub. Date: Jun. 16, 2016

(65) Prior Publication Data
US 2019/0032154 A1    Jan. 31, 2019

Related U.S. Application Data

(60) Provisional application No. 62/088,823, filed on Dec. 8, 2014.

(51) Int. Cl.
C12Q 1/6897 (2018.01)
C12N 15/86 (2006.01)
G01N 33/58 (2006.01)
C12N 15/63 (2006.01)
C12N 15/11 (2006.01)
G01N 33/50 (2006.01)

(52) U.S. Cl.
CPC .......... *C12Q 1/6897* (2013.01); *C12N 15/11* (2013.01); *C12N 15/63* (2013.01); *G01N 33/5008* (2013.01); *G01N 33/5023* (2013.01); *G01N 33/582* (2013.01)

(58) Field of Classification Search
None
See application file for complete search history.

(56) References Cited

U.S. PATENT DOCUMENTS

2014/0178914 A1    6/2014    Minshull et al.

FOREIGN PATENT DOCUMENTS

| CN | 103 881 979 A | 6/2014 |
| KR | 2014 0095175 A1 | 8/2014 |
| WO | 2014/142984 A1 | 9/2014 |
| WO | 2014/186409 A1 | 11/2014 |

OTHER PUBLICATIONS

Kim JH, Lee SR, Li LH, Park HJ, Park JH, Lee KY, Kim MK, Shin BA, Choi SY. High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Luke G. Translating 2A research into practice. Innovations in Biotechnology, 2012, pp. 162-186.
Batulan, Z., Haddad, G.A., and Blunck, R. (2010). An intersubunit interaction between S4-S5 linker and S6 is responsible for the slow off-gating component in Shaker K+ channels. The Journal of biological chemistry 285, 14005-14019.
Corish, P., and Tyler-Smith, C. (1999). Attenuation of green fluorescent protein half-life in mammalian cells. Protein engineering 12, 1035-1040.
Cvetkovska, V., Hibbert, A.D., Emran, F., and Chen, B.E. (2013). Overexpression of Down syndrome cell adhesion molecule impairs precise synaptic targeting. Nature neuroscience 16, 677-682.
Diao, F., and White, B.H. (2012). A novel approach for directing transgene expression in *Drosophila* : T2A-Gal4 in-frame fusion. Genetics 190, 1139-1144.
Gaj T., Gersbach, C.A., and Barbas, C.F., 3rd (2013). ZFN, TALEN, and CRISPR/Cas-based methods for genome engineering. Trends in biotechnology 31, 397-405.
Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.
Grueber, W.B., Jan, L.Y., and Jan, Y.N. (2003). Different levels of the homeodomain protein cut regulate distinct dendrite branching patterns of *Drosophila* multidendritic neurons. Cell 112, 805-818.
Furtado, A., and Henry, R. (2002). Measurement of green fluorescent protein concentration in single cells by image analysis. Analytical biochemistry 310, 84-92.
Hardin, P.E., Hall, J.C., and Rosbash, M. (1990). Feedback of the *Drosophila* period gene product on circadian cycling of its messenger RNA levels. Nature 343, 536-540.
Jinek, M., Chylinski, K., Fonfara, I., Hauer, M., Doudna, J.A., and Charpentier, E. (2012). A programmable dual-RNA-guided DNA endonuclease in adaptive bacterial immunity. Science 337, 816-821.
Khmelinskii, A., Keller, P.J., Bartosik, A., Meurer, M., Barry, J.D., Mardin, B.R., Kaufmann, A., Trautmann, S., Wachsmuth, M., Pereira, G., et al. (2012). Tandem fluorescent protein timers for in vivo analysis of protein dynamics. Nature biotechnology 30, 708-714.

(Continued)

*Primary Examiner* — Channing S Mahatan
(74) *Attorney, Agent, or Firm* — Marie-Helene Rochon

(57) ABSTRACT

The present disclosure concerns a Protein Quantification Reporter (PQR) linker which is capable of being cleaved during the translation of a messenger RNA to quantify a protein of interest. The PQR linker can encode a peptide of SEQ ID NO: 23 and have the nucleic acid sequence of SEQ ID NO: 25. The PQR linker is located in a nucleic acid molecule encoding a poly-protein between a reporter protein and the protein of interest. While the messenger RNA encoding the poly-protein is being translated, the presence of the PQR linker causes cleavage of the poly-protein and consequently the release at a stoichiometric ratio of the reporter protein and the protein of interest. The signal associated with the cleaved reporter protein can be measured to estimate or quantify the protein of interest.

21 Claims, 30 Drawing Sheets
Specification includes a Sequence Listing.

(56) References Cited

OTHER PUBLICATIONS

Kim, J.H., Lee, S.R., Li, L.H., Park, H.J., Park, J.H., Lee, K.Y., Kim, M.K., Shin, B.A, and Choi, S.Y. (2011). High cleavage efficiency of a 2A peptide derived from porcine teschovirus-1 in human cell lines, zebrafish and mice. PloS one 6, e18556, pp. 1-8.

Lindstrom, M.S. (2009). Emerging functions of ribosomal proteins in gene-specific transcription and translation. Biochemical and biophysical research communications 379, 167-170.

Luke G.A., de Felipe, R, Lukashev, A., Kallioinen, S.E, Bruno, E.A., and Ryan, M.D. (2008). Occurrence, function and evolutionary origins of '2A-like' sequences in virus genomes. The Journal of general virology 89, 1036-1042.

Mane, V.P., Heuer, M.A., Hillyer, P., Navarro, M.B., and Rabin, R.L. (2008). Systematic method for determining an ideal housekeeping gene for real-time PCR analysis. Journal of biomolecular techniques : JBT 19, 342-347.

Noa, E.M., and Ribas de Pouplana, L. (2012). Speeding with control: codon usage, tRNAs, and ribosomes. Trends in genetics : TIG 28, 574-581.

Pedelacq, J.D., Cabantous, S., Tran, T., Terwilliger, T.C., and Waldo, G.S. (2006). Engineering and characterization of a superfolder green fluorescent protein. Nature biotechnology 24, 79-88.

Pfeiffer, B.D., Ngo, T.T., Hibbard, K.L., Murphy, C., Jenett, A., Truman, J.W., and Rubin, G.M. (2010). Refinement of tools for targeted gene expression in Drosophila. Genetics 186, 735-755.

Reddy, P., Zehring, W.A., Wheeler, D.A., Pirrotta, V., Hadfield, C., Hall, J.C., and Rosbash, M. (1984). Molecular analysis of the period locus in Drosophila melanogaster and identification of a transcript involved in biological rhythms. Cell 38, 701-710.

Shaner, N. C., Lin, M.Z., McKeown, M.R., Steinbach, P.A.., Hazelwood, K.L., Davidson, M.W., and Tsien, R.Y. (2008). Improving the photostability of bright monomeric orange and red fluorescent proteins. Nat Methods 5, 545-551.

Szymczak, A.L., Workman, C.J., Wang, Y., Vignali, K.M., Dilioglou, S., Vanin, E.F., and Vignali, D.A. (2004). Addendum: Correction of multi-gene deficiency in vivo using a single 'self-cleaving' 2A peptide-based retroviral vector. Nature biotechnology 22, 760.

Yang, S., Cohen, C.J., Peng, P.D., Zhao, Y., Cassard, L., Yu, Z., Zheng, Z., Jones, S., Restifo, N.P., Rosenberg, S.A., et al. (2008). Development of optimal bicistronic lentiviral vectors facilitates high-level TCR gene expression and robust tumor cell recognition. Gene therapy 15, 1411-1423.

Zhao, M.L., Sable, E.O., Iverson, L.E., and Wu, C.F. (1995). Functional expression of Shaker K+ channels in cultured Drosophila "giant" neurons derived from Sh cDNA transformants: distinct properties, distribution, and turnover. The Journal of neuroscience : the official journal of the Society for Neuroscience 15, 1406-1418.

Zhou, J.H., Zhang, J., Chen, H.T., Ma, L.N., Ding, Y.Z., Pejsak, Z., and Liu, Y.S. (2011). The codon usage model of the context flanking each cleavage site in the polyprotein of foot-and-mouth disease virus. Infection, genetics and evolution : journal of molecular epidemiology and evolutionary genetics in infectious diseases 11, 1815-1819.

Luke, Translating 2A research into practice, pp. 162-186 in Innovations in Biotechnology ed. By Dr. Eddy Agbo, 2012, ISBN 978-953-51/0096-6.

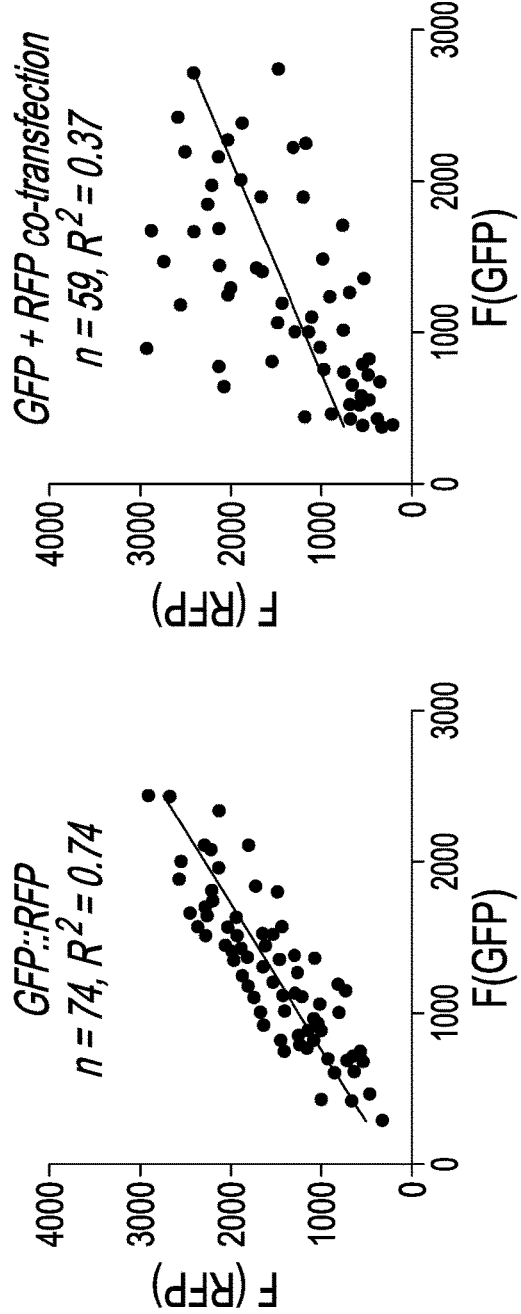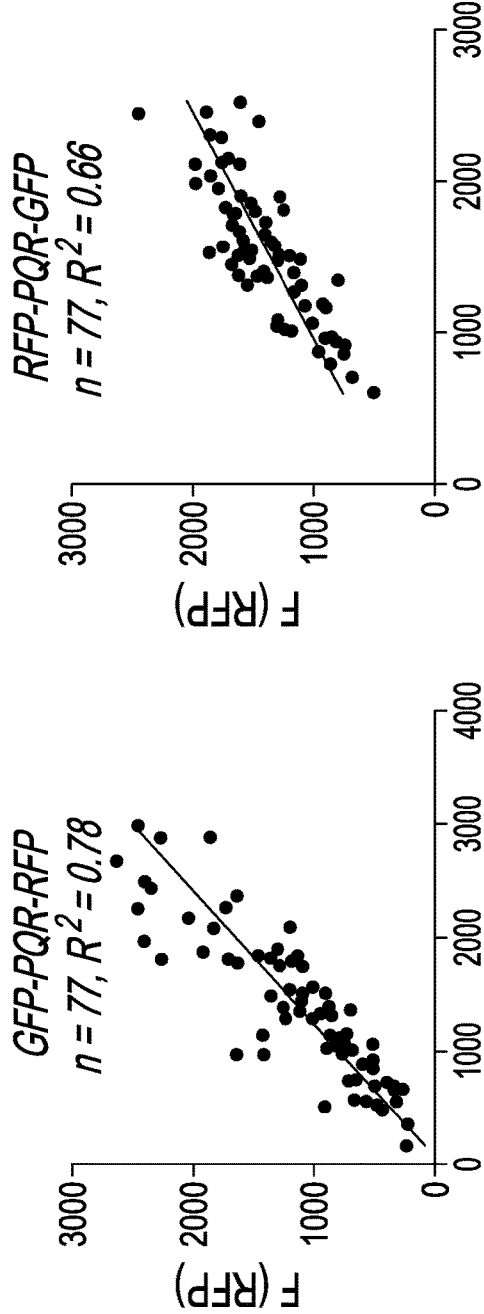
Figure 3A
Figure 3B
Figure 3C
Figure 3D

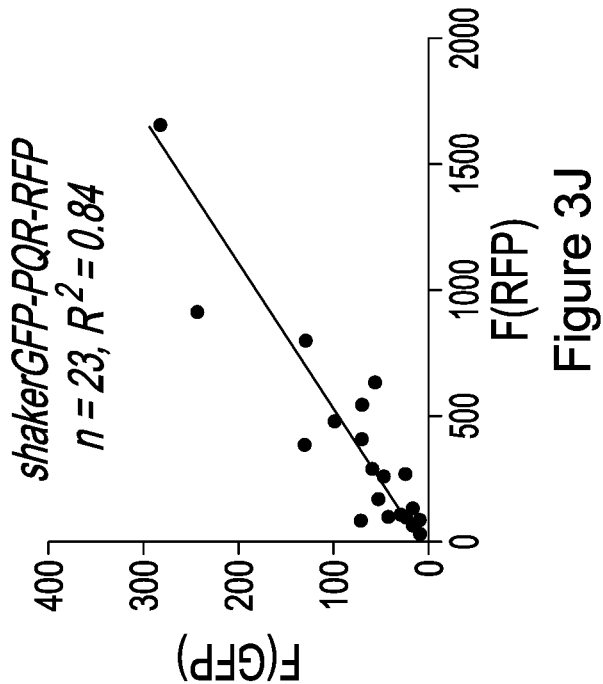
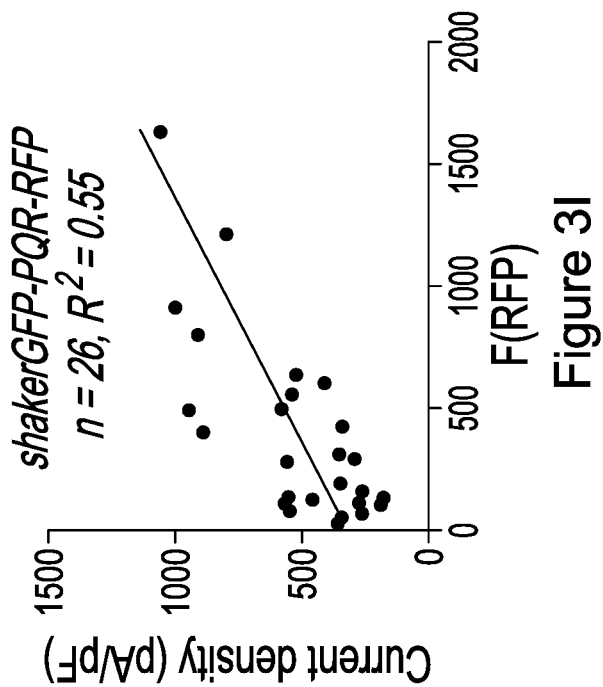
Figure 3I
Figure 3J

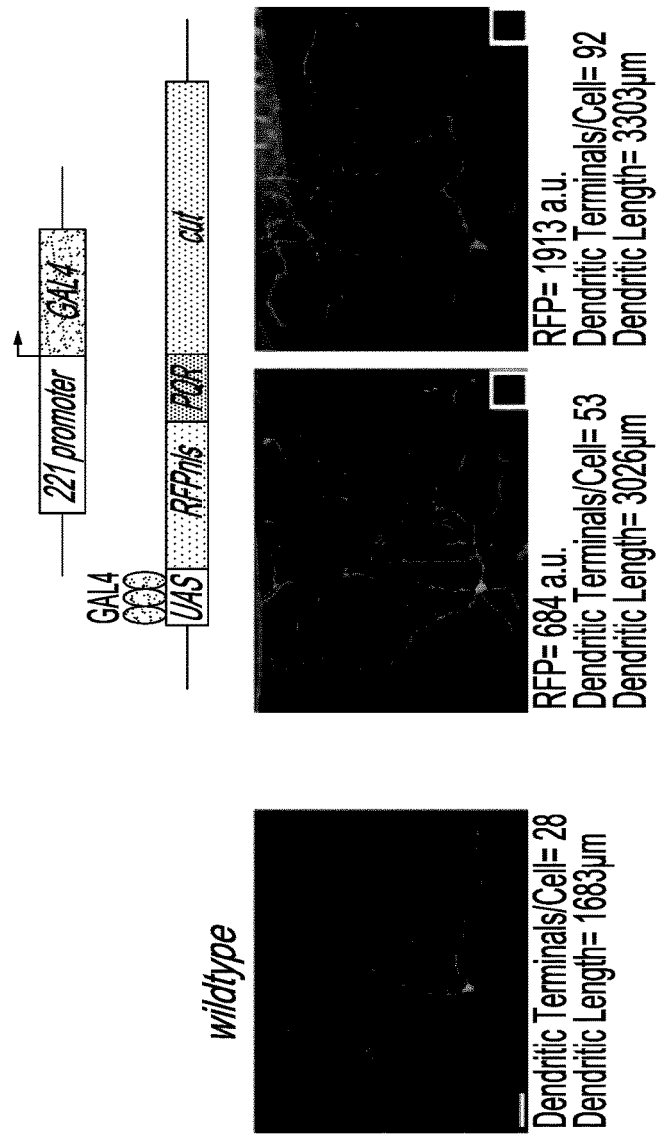
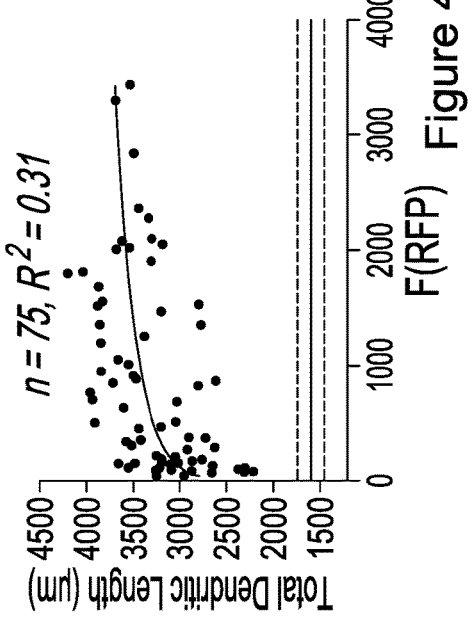
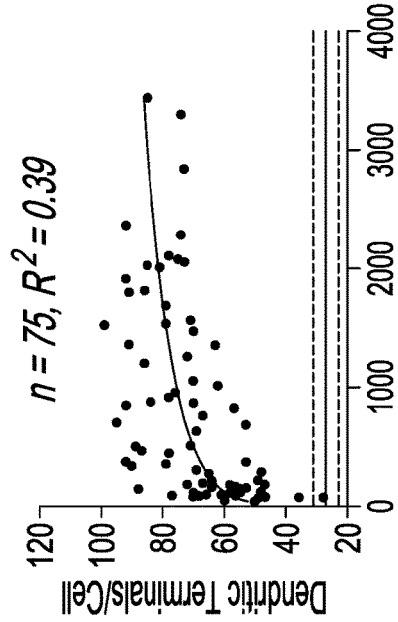
Figure 4C
Figure 4D
Figure 4E

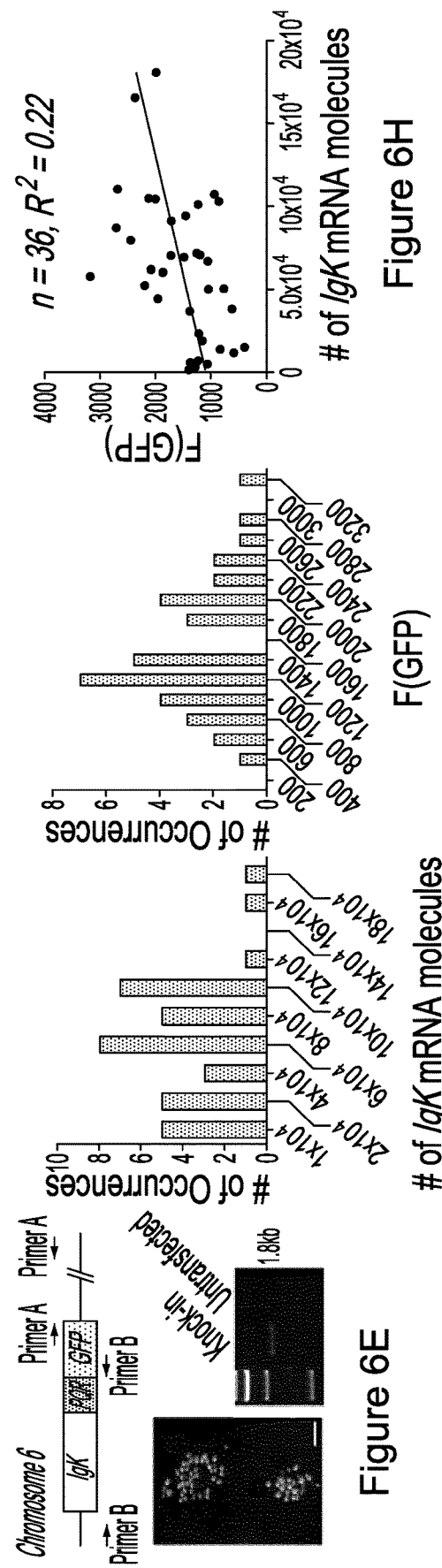

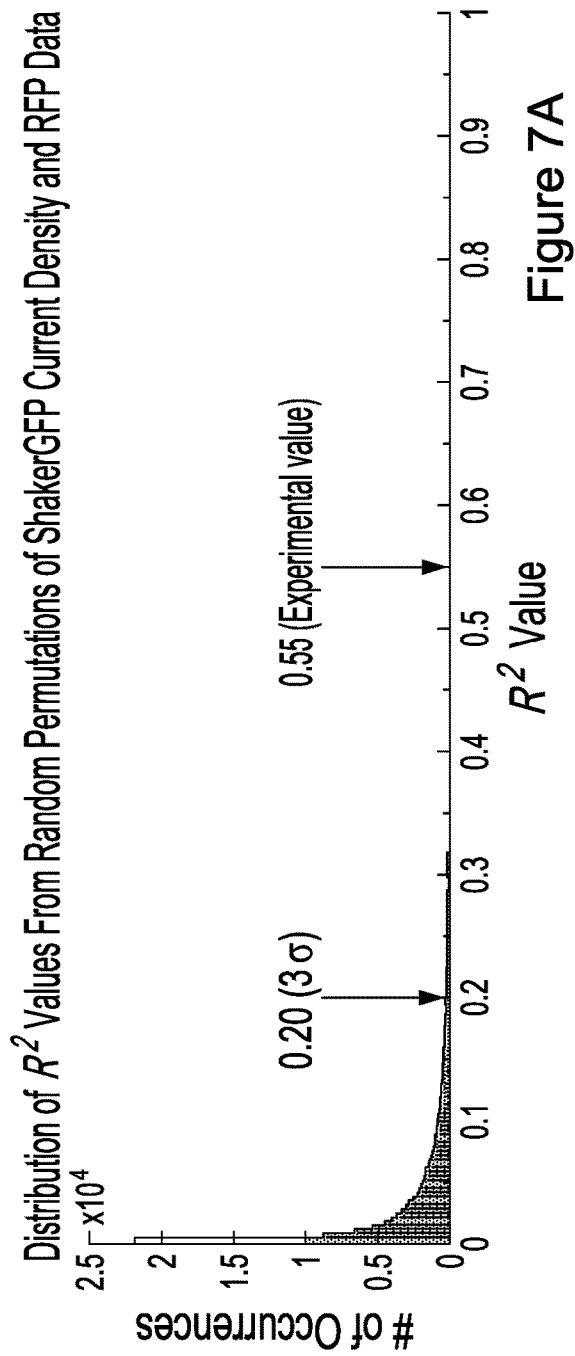
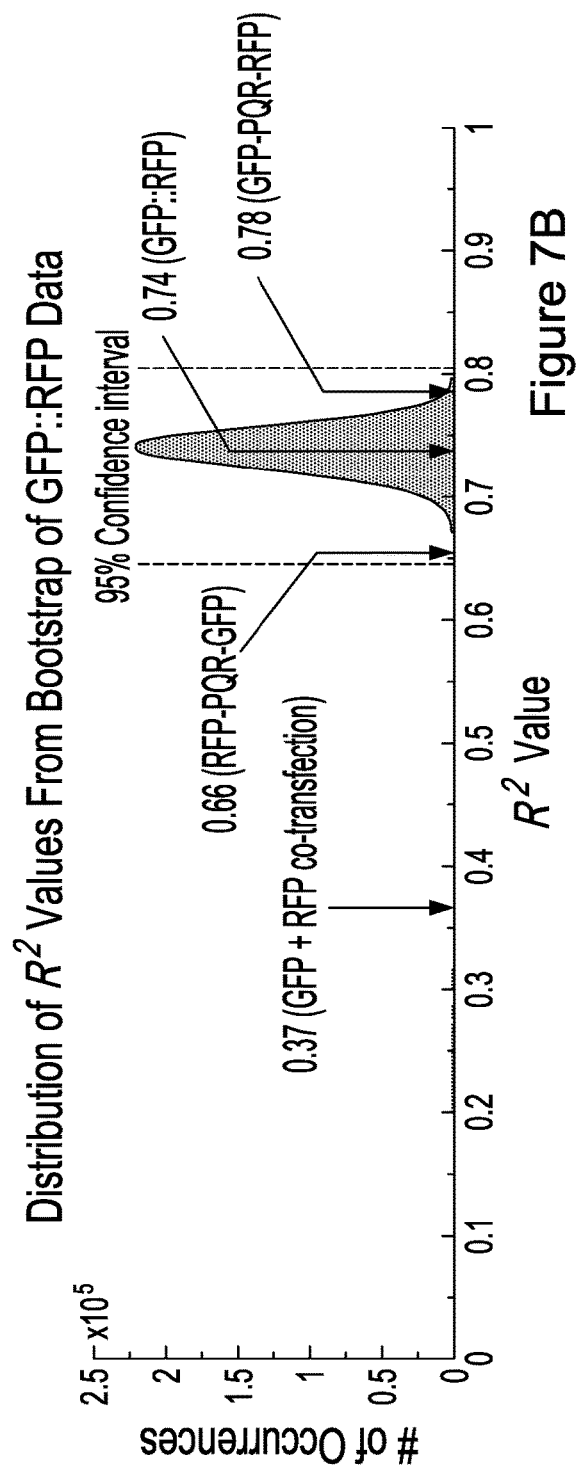
Figure 7A
Figure 7B

Embryos

2nd instar Larval body wall

US 10,752,965 B2

CLEAVABLE NUCLEIC ACID LINKERS FOR PROTEIN QUANTIFICATION RATIOING

CROSS-REFERENCE TO RELATED APPLICATIONS

This application claims priority from U.S. provisional patent application 62/088,823 filed on Dec. 8, 2014. This application is filed concurrently with a sequence listing. The content of the priority application and the sequence listing is incorporated herewith in their entirety.

TECHNOLOGICAL FIELD

This disclosure relates to protein quantification ratioing using a cleavable nucleic acid linker intended to be located in a nucleic acid molecule encoding a protein of interest and a quantifiable protein marker.

BACKGROUND

The two most common methods for measuring absolute or relative protein amounts are protein assays and quantitative Western or immuno-blots. All methods for protein quantitation start with the isolation of large quantities of the cell type of interest due to the limited sensitivity and detection capabilities of these techniques, making them time consuming and laborious. The cellular resolution of these techniques is also limited because the isolated tissue is typically a heterogeneous population of cells that can include a wide range of cell types outside of a user's interest. These techniques are necessarily destructive processes as cells must be lysed to extract their protein content to be manipulated for the detection processes. Inaccuracies in quantitation using immuno-detection are further compounded by variabilities in antibody used to detect the protein, such as the avidity and affinity of the antibody, access of the antibody to the protein epitope, phosphorylation state of the protein, and cross-reactivities of the antibody. The use of a "housekeeping" protein for normalization is subject to the same limitations, as housekeeping protein quantification is still dependent on antibody detection, and differences across conditions, along with cellular heterogeneity can increase or decrease the housekeeping protein quantified without affecting the protein of interest (e.g., epithelial cells within neural tissue may not express a neural protein), leading to an inaccurate ratio between the protein of interest and the normalization control.

It would be highly desirable to be provided with a protein quantification method which would have heightened sensitivity and/or sensibility. It would also be desirable to be provided with a non-destructive protein quantification method that could allow, for example, live cell tracking. It would further be desirable to be provided with a protein quantification method that could be applied to a single cell. It would also be desirable to track and quantify protein production amounts over time in a cell by performing real-time measurements of protein production in single cells, at cellular or sub-cellular resolution.

BRIEF SUMMARY

The present disclosure concerns a Protein Quantitation Reporter (PQR) linker which is capable of being cleaved during the translation of a messenger RNA to quantify a protein of interest. The PQR linker can encode a peptide of SEQ ID NO: 23 and have the nucleic acid sequence of SEQ ID NO: 25. To quantify the protein of interest, the PQR linker is included in a nucleic acid molecule encoding a reporter protein and the protein of interest. In the nucleic acid molecule, the PQR linker is located between the reporter protein and the protein of interest. While the messenger RNA encoding the two proteins is being translated, the presence of the PQR linker forces a cleavage event between the two proteins and consequently causes the release of a stoichiometry ratio of the reporter protein and the protein of interest. The signal associated with the cleaved reporter protein can be measured to estimate or quantify the protein of interest.

According to a first aspect, the present disclosure provides a protein quantitation reporter linker molecule for quantifying a protein of interest in a host cell. Broadly, the protein quantitation reporter encodes a cleavable peptide having the amino acid sequence of SEQ ID NO: 23 and is a nucleic acid molecule having the nucleic acid sequence of SEQ ID NO: 25. The cleavable peptide has the amino acid sequence of SEQ ID NO: 23:

$$\text{GSGX}_1\text{X}_2\text{X}_3\text{X}_4\text{X}_5\text{X}_6\text{X}_7\text{X}_8\text{X}_9\text{LX}_{10}\text{X}_{11}\text{X}_{12}\text{GDVEX}_{13}\text{N}_{PGP} \quad \text{(SEQ ID NO: 23)}$$

in which $X_1$ is V or absent; $X_2$ is K or absent; $X_3$ is Q or absent; $X_4$ is T, C, A or absent; $X_5$ is L, T or E; $X_6$ is N or G; $X_7$ is F, Y or R; $X_8$ is D, A, G or S; $X_9$ is L or S; $X_{10}$ is K or L; $X_{11}$ is L, T or Q; $X_{12}$ is A or C and $X_{13}$ at position 21 is S or E.

The nucleic acid molecule has the nucleic acid sequence of SEQ ID NO: 25:

(SEQ ID NO: 25)
$N_1N_2N_3 \ N_4N_5N_6 \ N_7N_8N_9 \ N_{10}N_{11}N_{12} \ N_{13}N_{14}N_{15} \ N_{16}N_{17}$ $N_{18} \ N_{19}N_{20}N_{21} \ N_{22}N_{23}N_{24} \ N_{25}N_{26}N_{27}N_{28}N_{29}N_{30} \ N_{31}$ $N_{32}N_{33} \ N_{34}N_{35}N_{36} \ N_{37}N_{38}N_{39} \ N_{40}N_{41}N_{42} \ N_{43}N_{44}N_{45}$ $N_{46}N_{47}N_{48} \ N_{49}N_{50}N_{51} \ N_{52}N_{53}N_{54}N_{55}N_{56}N_{57} \ N_{58}N_{59}$ $N_{60} \ N_{61}N_{62}N_{63} \ \text{AAY CCN}_{64} \ \text{GGA CCN}_{65}$ in which $N_1$ to $N_{63}$ are any nucleic acid capable of forming codons encoding $\text{GSGX}_1\text{X}_2\text{X}_3\text{X}_4\text{X}_5\text{X}_6\text{X}_7\text{X}_8\text{X}_9\text{LX}_{10}\text{X}_{11}\text{X}_{12}\text{GDVEX}_{13}$ of SEQ ID NO: 23, $N_{64}$ is T or U and $N_{65}$ is T or U; and at least 50% of the codons encoding $X_1X_2X_3X_4X_5X_6X_7X_8X_9\text{L}X_{10}X_{11}X_{12}\text{GDVEX}_{13}$ of SEQ ID NO: 23 correspond to the codons least favored in the host cell. In an embodiment, the cleavable peptide has the amino acid sequence of SEQ ID NO: 24:

$$\text{GSGX}_{14}\text{X}_{15}\text{X}_{16}\text{X}_{17}\text{X}_{18}\text{X}_{19}\text{LX}_{20}\text{X}_{21}\text{X}_{22}\text{GDVEENPGP} \quad \text{(SEQ ID NO: 24)}$$

in which $X_{14}$ is A or absent; $X_{15}$ is E or T; $X_{16}$ is G or N; $X_{17}$ is R or F; $X_{18}$ is G or S; $X_{19}$ is S or L; $X_{20}$ is L or K; $X_{21}$ is T or Q and $X_{22}$ is C or A. In another embodiment, the protein quantitation reporter linker molecule is a deoxyribonucleic (DNA) molecule. In still a further embodiment, the protein quantitation reporter linker molecule has a nucleic acid sequence of SEQ ID NO: 26:

(SEQ ID NO: 26)
$N_1N_2N_3 \ N_4N_5N_6 \ N_7N_8N_9 \ N_{10}N_{11}N_{12} \ N_{13}N_{14}N_{15} \ N_{16}N_{17}$

-continued $N_{18}\ N_{19}N_{20}N_{21}\ N_{22}N_{23}N_{24}\ N_{25}N_{26}N_{27}N_{28}N_{29}N_{30}\ N_{31}N_{32}$ $N_{33}N_{34}N_{35}N_{36}\ N_{37}N_{38}N_{39}\ N_{40}N_{41}N_{42}\ N_{43}N_{44}N_{45}\ N_{46}N_{47}$ $N_{48}\ N_{49}N_{50}N_{51}\ N_{52}N_{53}N_{54}N_{55}N_{56}N_{57}\ N_{58}N_{59}N_{60}$ $N_{61}N_{62}N_{63}$ AAY CCT GGA CCT in which $N_1$ to $N_{63}$ are any nucleic acid capable of forming codons encoding $GSGX_1X_2X_3X_4X_5X_6X_7X_8X_9LX_{10}X_{11}X_{12}GDVEX_{13}$ of SEQ ID NO: 23. In yet another embodiment, in the nucleic acid encoding the protein quantitation reporter linker, at least 80% of the codons encoding $X_1X_2X_3X_4X_5X_6X_7X_8X_9LX_{10}X_{11}X_{12}GDVEX_{13}$ of SEQ ID NO: 23 correspond to the codons least favored in the host cell.

In a second aspect, the present disclosure provides a vector for quantifying a protein of interest in a host cell, said vector comprising a first nucleic acid molecule encoding the protein quantitation reporter linker described herein. In an embodiment, the vector further comprises a second nucleic acid molecule encoding a reporter protein operatively linked to the first nucleic acid molecule so that the first nucleic acid molecule and second nucleic acid molecule are transcribed as a single messenger RNA transcript from the vector. In another embodiment, the vector further comprises a third nucleic acid molecule encoding a protein of interest operatively linked to the first nucleic acid molecule so that the first nucleic acid molecule and the third nucleic acid molecule are transcribed as a single messenger RNA transcript from the vector. In still another embodiment, the vector further comprises a second nucleic acid molecule encoding a reporter protein and a third nucleic acid molecule encoding a protein of interest, wherein the second nucleic acid molecule and the third nucleic acid molecule are operatively linked to the first nucleic acid molecule and wherein the first nucleic acid molecule is located between the second nucleic acid molecule and the third nucleic acid molecule, so that the first nucleic acid molecule, the second nucleic acid molecule and the third nucleic acid molecule are transcribed as a single messenger RNA transcript from the vector. In yet another embodiment, the second nucleic acid molecule is upstream of the third nucleic acid molecule or downstream of the third nucleic acid molecule. In still a further embodiment, the reporter protein is selected from the group consisting of a fluorescent protein, an antibiotic-resistance protein, an immunoglobulin protein, an ion channel, a transcription factor, a ribosomal protein, an enzyme and a receptor. In yet a further embodiment, the fluorescent protein is selected from the group consisting of a green-fluorescent protein (GFP), a red fluorescent protein (RFP), a yellow fluorescent protein (YFP), a blue fluorescent protein (BFP) and a cyan fluorescent protein (CFP).

According to a third aspect, the present disclosure provides a kit for quantifying a protein of interest in a host cell, said kit comprising the vector of described herein and instructions for using the vector to quantify the protein of interest.

According to a fourth aspect, the present disclosure provides a transgenic host cell comprising the vector described herein.

According to a fifth aspect, the present disclosure provides a transgenic host cell comprising (i) a first nucleic acid molecule encoding the protein quantitation reporter linker described herein, (ii) a second nucleic acid molecule encoding a reporter protein and (iii) a third nucleic acid molecule encoding a protein of interest, wherein the second nucleic acid molecule and the third nucleic acid molecule are operatively linked to the first nucleic acid molecule and wherein the first nucleic acid molecule is located between the second nucleic acid molecule and the third nucleic acid molecule, so that the first nucleic acid molecule, the second nucleic acid molecule and the third nucleic acid molecule are transcribed as a single messenger RNA transcript. In an embodiment, the first nucleic acid molecule, the second nucleic acid molecule and the third nucleic acid molecule are integrated in the genome of the host cell.

According to a sixth aspect, the present disclosure provides a host comprising the transgenic host cell described herein.

According to a seventh aspect, the present disclosure provides a method for quantifying a protein of interest in a host or a host cell. Broadly the method comprises (i) expressing the vector described herein in the host or the host cell so as to cause the generation of a nucleic acid transcript encoding a poly-protein, wherein the poly-protein comprises the protein of interest, a cleavable peptide and a reporter protein and wherein the cleavable peptide can be cleaved during the translation of the nucleic acid transcript to generate a cleaved reporter protein and (ii) measuring a signal associated with the cleaved reporter protein to quantify the protein of interest. In an embodiment, the reporter protein is a fluorescent protein and step (ii) further comprises determining the fluorescence associated with the cleaved reporter protein. In still another embodiment, the host cell is a living cell. In yet another embodiment, the host cell is a single cell.

BRIEF DESCRIPTION OF THE DRAWINGS

Having thus generally described the nature of the invention, reference will now be made to the accompanying drawings, showing by way of illustration, a preferred embodiment thereof, and in which:

FIG. 3A shows that red and green fluorescence intensities of HEK293 cells expressing a fusion protein of GFP and RFP (GFP::RFP) were linearly correlated with a coefficient of determination, $R^2=0.74$ (n=74 cells, $P<0.001$). Fluorescence values are in arbitrary units.

FIG. 3B shows that co-transfection of GFP and RFP produced a weak correlation between fluorescence intensities (n=59 cells, $P<0.001$).

FIG. 3C shows that insertion of a PQR between GFP and RFP produces red and green fluorescence intensities that were linearly correlated. $R^2$ values for GFP-PQR-RFP (n=77) was not significantly different from the fusion protein data ($P>0.05$).

FIG. 3D shows that insertion of a PQR between GFP and RFP produces red and green fluorescence intensities that were linearly correlated. $R^2$ values for RFP-PQR-GFP (n=77) was not significantly different from the fusion protein data ($P>0.05$).

Steady-state current was measured at +mV and current density (pA/pF) was calculated using the membrane capacitance.

FIG. 3I shows that red fluorescence intensities were correlated with $K^{30}$ channel current density in cells expressing ShakerGFP-PQR-RFP. $R^2$ values for current density to RFP, and GFP to RFP were not significantly different from the current density to GFP positive control data (P>0.05); see also FIGS. 7 and 9. These correlations were not due to unseparated RFP fusion products since green fluorescence was restricted to the membrane, and red fluorescence remained cytoplasmic (images in 3G). All fluorescence intensities are plotted in arbitrary units (a.u.).

FIG. 3J shows that red fluorescence intensities were correlated with green fluorescence in cells expressing ShakerGFP-PQR-RFP. $R^2$ values for current density to RFP, and GFP to RFP were not significantly different from the current density to GFP positive control data (P>0.05); see also FIGS. 7 and 9. These correlations were not due to unseparated RFP fusion products since green fluorescence was restricted to the membrane, and red fluorescence remained cytoplasmic (images in 3G). All fluorescence intensities are plotted in arbitrary units (a.u.).

Figure 4A:
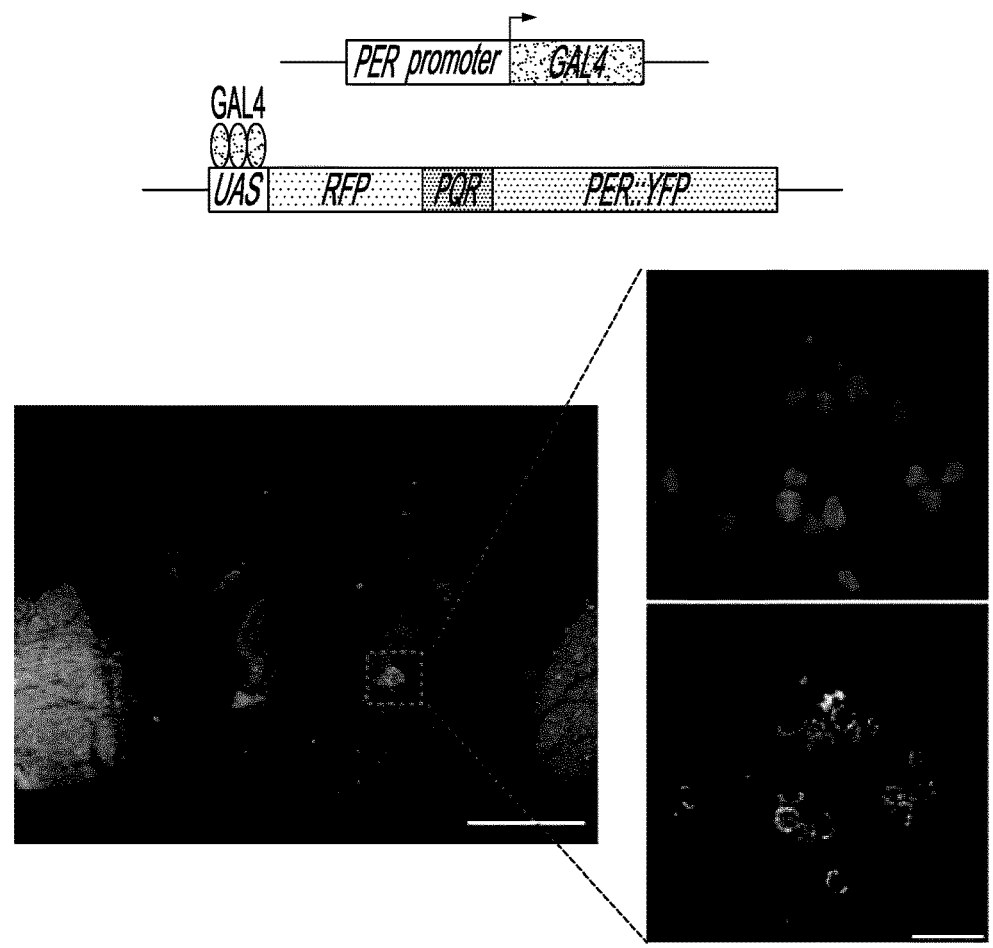

FIG. 4A illustrates that PQR can relate cellular phenotype as a function of protein concentration. PQR can detect cyclic increases in protein concentration over time. RFP-PQR-PER::YFP was used to quantitate changes in PER transcription factor levels in single neurons in the animal. An image of the Drosophila brain is shown with RFP and PER::YFP expression restricted to the small lateral ventral neurons (dotted box and right panels) using Per-Gal4 to drive UAS—RFP-PQR-PER::YFP. Red fluorescence within the neurons remained in the cytoplasm, and yellow fluorescence was peri-nuclear. Scale bars are 100 μm (left panel) and 10 μm (right panels).

Figure 4B:
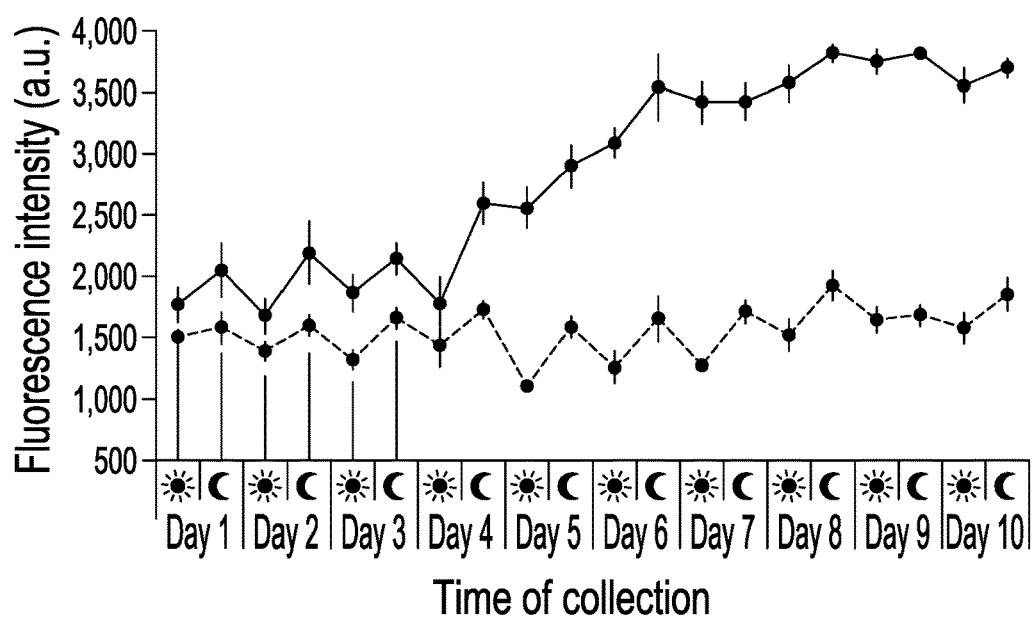

FIG. 4B shows that red fluorescence (full line) increased cyclically in neurons over days. Flies were entrained on a 12 hour light-dark cycle and red and yellow fluorescence intensities were measured within single neurons at zeitgeber time 0 (sun symbol) and 12 (moon symbol) (n=6 cells/6 animals/time point). Yellow fluorescence (dashed line) intensities cycles every 24 hours without accumulating beyond a fixed value, reflecting the rapid lifetime of PER. Red fluorescence (fill line) intensities were also cyclical, but gradually increased over several days, reflecting the integrated amount of PER produced over time. Error bars are S.E.M. See also FIG. 10.

FIG. 4C shows PQR in single living neurons being used to quantitatively relate dendritic complexity with Cut protein levels. Dendritic complexity of Drosophila da neurons is regulated by the transcription factor Cut. Wild-type class I da Neurons (left panel) have relatively simple dendritic arbors. Expression of RFPnls-PQR-cut within class I neurons increases dendritic branch number and total dendritic branch length (middle and right panels). Red fluorescence within the nucleus (inset in middle and right panels) reflecting Cut protein levels indicates that Cut controls dendritic growth in a concentration dependent manner. Posterior is up and dorsal to the right in all three panels. Scale bar is 30 μm.

FIG. 4D shows that dendritic complexity is logarithmically dependent on Cut protein concentration. The average number of dendritic branch terminals is indicated by the solid grey line (+1 S.D., dashed lines).

FIG. 4E shows that dendritic complexity is logarithmically dependent on Cut protein concentration. The total dendritic length in wild-type neurons is indicated by the solid grey line (+1 S.D., dashed lines).

Figure 5A:
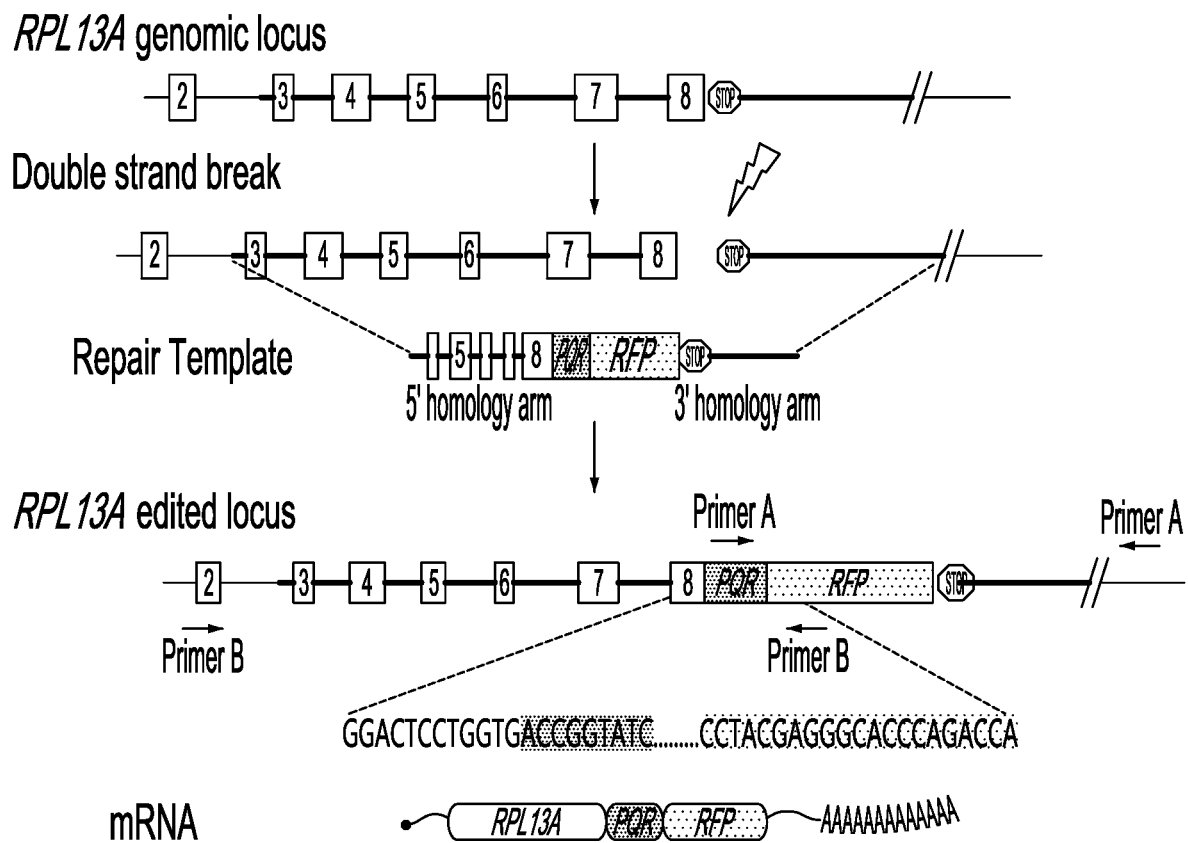

FIG. 5A illustrates that PQRs can be inserted into any genomic locus to quantitate endogenous protein levels. Insertion of a PQR before the final stop codon of the edogenous gene maintains the mRNA production fidelity and the 3' untranslated region (UTR) for all isoforms of the mRNA with the PQR. A site-specific DNA double-strand break is created using the CRISPR-Cas9 system. The break is repaired by the cell using homologous recombination, and in the presence with the PQR edited version. Shaded nucleotide sequences represent genomic sequencing results of an edited mouse RPL13A gene with a PQR-RFP insertion.

Figure 5B:
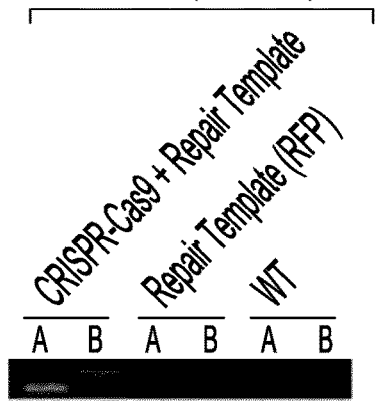
Figure 5B:
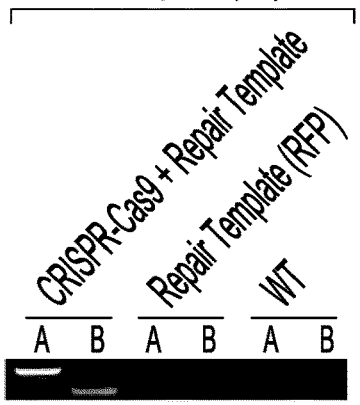
Figure 5B:
Figure 5B:

FIG. 5B shows that targeted genome editing allows for insertion of a PQR into the human genome. A repair template and guide RNA for CRISPER-Cas9 was designed for the RPL13A gene in human. RPL13A gene edited with PQR produced RFP. PQR insertion was verified using genomic PCR genotyping with primer pairs (see Table 4B) that spanned PQR and outside the homology arms, followed by genomic sequencing. Scale bars are 100 μm.

Figure 5C:
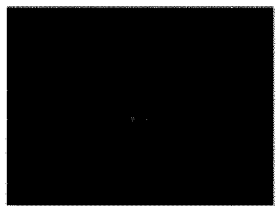
Figure 5C:

FIG. 5C shows that targets genome editing allows for insertion of a PQR into the drosophila genome. A repair template and guide RNA for CRISPR-Cas9 was designed for the RPL13A gene in drosophila. RPL13A gene edited with PQR produced RFP. PQR insertion was verified using genomic PCR genotyping with primer pairs (see Table 4B) that spanned PQR and outside the homology arms, followed by genomic sequencing. Scale bars are 100 μm.

Figure 5D:
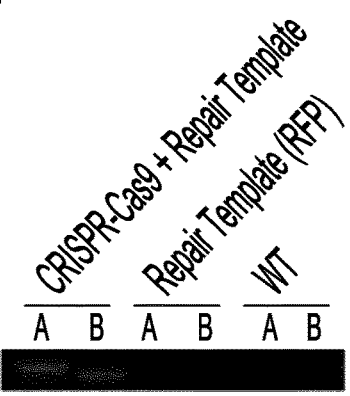
Figure 5D:
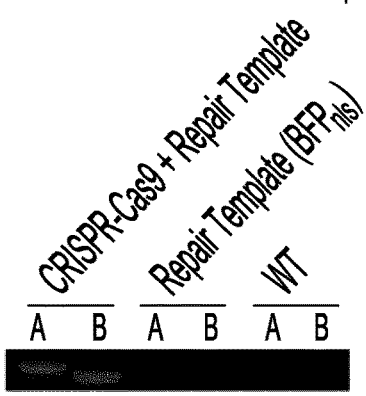
Figure 5D:
Figure 5D:
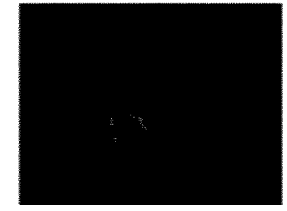
Figure 5D:
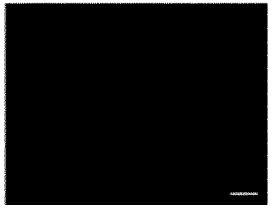

FIG. 5D shows that targets genomes editing allows for insertion of a PQR into the mouse genome. A repair template and guide RNA for CRISPER-Cas9 was designed for the RPL13A gene in mouse. RPL13A gene edited with PQR produced RFP or BFP with a nuclear localization signal (BFPnls). PQR insertion was verified using genomic PCR genotyping with primer pairs (see Table 4B) that spanned PQR and outside the homology arms, followed by genomic sequencing. Scale bars are 100 μm.

Figures 6A, 6B, 6C, 6D:
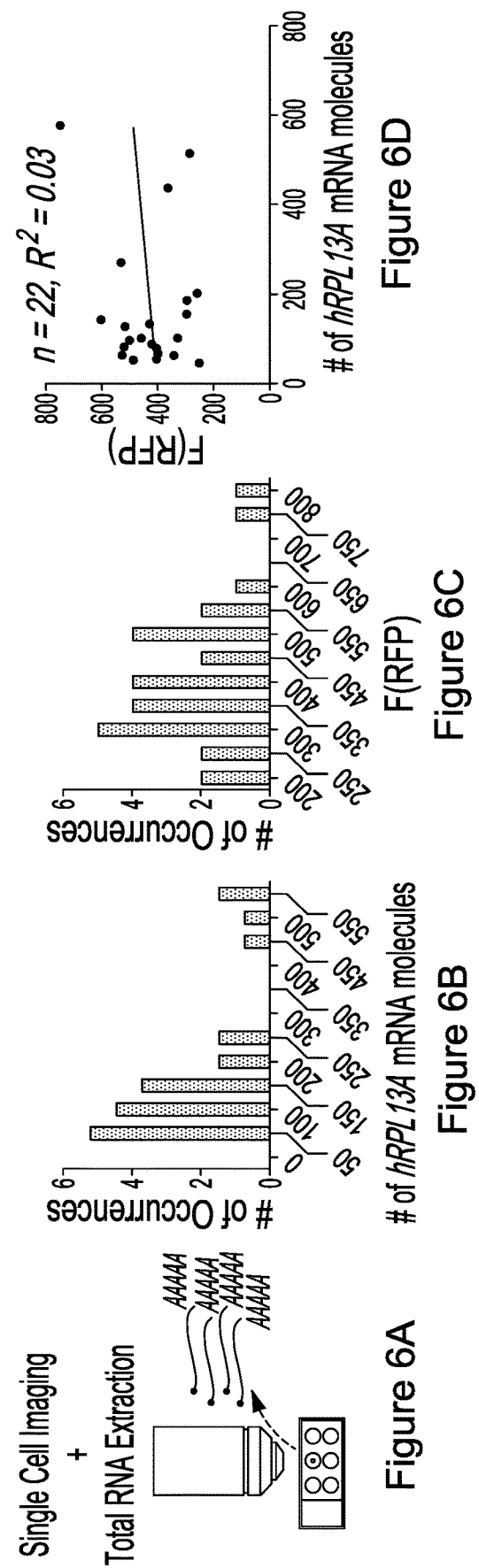

FIG. 6A illustrates protein quantification in single cells. Fluorescence intensity of single cells with a PQR knock-in is measured and cells are then lysed for total RNA extraction and single cell quantitative PCR.

FIG. 6B demonstrates that the frequency distribution of RPL13A mRNA amounts measured from single HEK293 cells exhibits moderate expression of the RPL13A gene. Quantitative PCR of RPL13A mRNA specifically containing PQR constructs was performed to avoid variability due to heterozygosity or polyploidy of the cells.

FIG. 6C shows that RFP fluorescence intensities (in arbitrary units) from single RPL13A-PQR-RFP knock-in cells exhibit a moderate distribution.

FIG. 6D shows that RFP fluorescence intensities (in arbitrary units) from single RPL13A-PQR-RFP knock-in cells exhibit a weak linear correlation to mRNA amounts (n=22. $R^2$=0.03).

FIG. 6E shows that the endogenous immunoglobulin kappa light chain (lgK) locus is edited to insert a PQR-GFP reporter at the end of the constant region in 22c10 mouse hybridoma cells (top panel). The correct insertion is verified by PCR primer pairs (see Table 4B) that lie within and outside of the locus (arrows, bottom right panel). 22c10 hybridoma cells produce green fluorescence (bottom left panel) after insertion of a PQR-GFP into the endogenous lgK locus. Scale bar is 25 μm. Representative PCR genotyping results show the expected size in the CRISPR-Cas9 transfected cells.

FIG. 6F shows that frequency distribution of lgK mRNA amounts measured from single 22c10 cells exhibits a broad range and high level of mRNA and protein expression.

FIG. 6G shows that frequency distribution of PQR-GFP fluorescence intensities measured from single 22c10 cells exhibits the broad range and high level of mRNA and protein expression.

FIG. 6H shows that the lgK protein expression was not strongly correlated with its mRNA amounts; see also FIG. 9.

FIG. 7A illustrates the statistical analysis of $R^2$ values from experiments, related to FIG. 3. How accurate are our $R^2$ values for each experiment? We tested the null hypothesis that the experimental variables were independent of each other and that the true $R^2$ value was 0. We used the permutation test to obtain a P value on the likelihood of obtaining out $R^2$ value by randomly shuffling the data and calculating a new $R^2$ value, repeated for one million runs. A representative example is shown for the frequency distribution of randomly permuted $R^2$ values derived from the ShakerGFP current density versus RFP data. The experimental R2 value was 0.55(n=28 cells) and was highly significant from the average randomly permuted $R^2$ value, with three S.D.=0.20.

FIG. 7B shows Bootstrap of positive control fusion protein data being used to compare between experiments. Our experimentally derived $R^2$ values were not equal to 1 most likely due to non-linear differences in protein kinetics between the two proteins, intramolecular interactions for the fusion proteins, and experimental precision. Given that our $R^2$ values for each experiment were significantly greater than random covariance (i.e., the true R2 is not close to 0) (a) but less than a perfect $R^2$=1, we needed a method to quantitatively compare $R^2$ values between experiments. We used the data from the fusion protein experiments as positive controls to compare the $R^1$ values among other conditions. We used the bootstrap method to generate a 95% confidence interval for the true $R^2$ value of the positive controls. We randomly chose 80% of the positive control data points to calculate a new $R^2$ value and repeated this for ten million runs, and used these simulated $R^2$ values to obtain upper and lower estimates of the positive control $R^2$ values. A representative example is shown for the frequency distribution of $R^2$ values calculated from randomly choosing 90% of the GFP::RFP data, performed ten million times. $R^2$ values for the RFP-PQR-GFP and GFP-PQR-RFP fell within the 95% confidence interval, whereas the $R^2$ value for co-transfection of GFP and RFP did not.

Figures 8A, 8B, 8C:
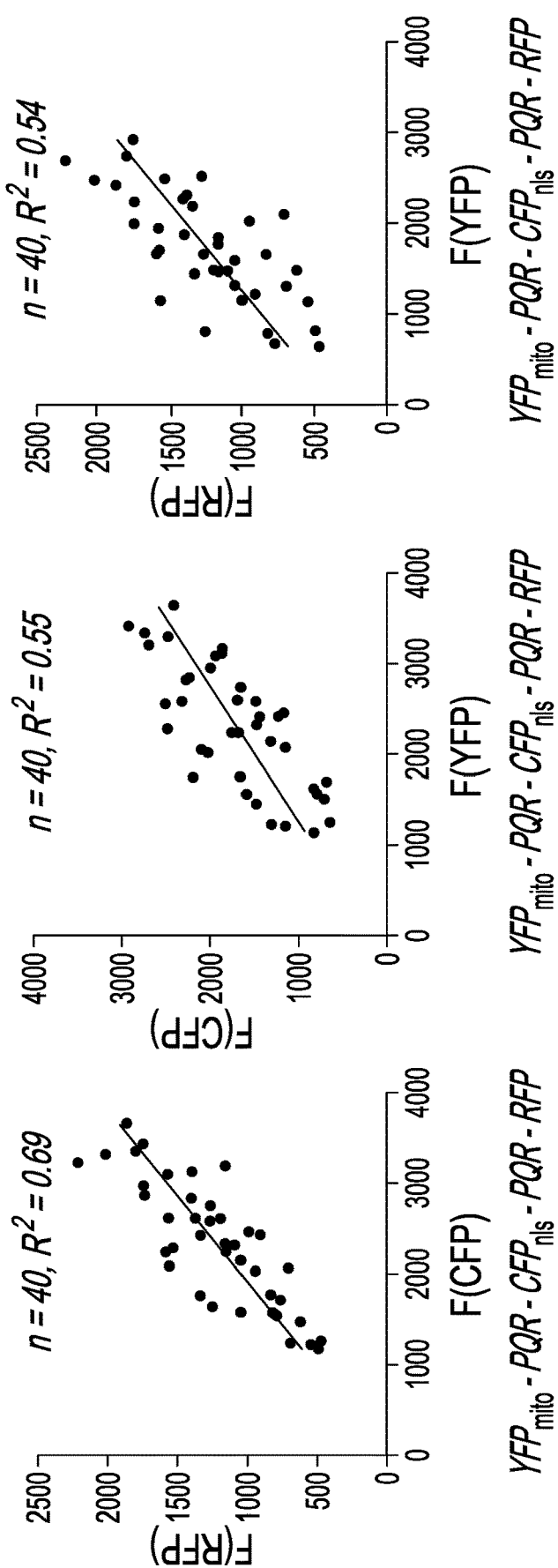

FIG. 8A illustrates that Protein Quantitation Rationing can be used with multiple microscopy methods and multiple fluorophores within different subcellular compartments, related to FIG. 3. Image analysis of HEK293 cells expressing YFPmito-PQR-CFPnls-PQR-RFP demonstrates linear correlations between RFP and CFP fluorescence intensities within different subcellular compartments. We used mitochondrial (mito) and nuclear (nls) localization signals on YFP and CFP, respectively, with RFP remaining cytosolic. Fluorescence intensities within the nucleus compared to cytoplasm were consistently the most highly correlated.

FIG. 8B shows an image analysis of HEK293 cells expressing YFPmito-PQR-CFPnls-PQR-RFP demonstrating linear correlations between CFP and YFP fluorescence intensities within different subcellular compartments. We used mitochondrial (mito) and nuclear (nls) localization signals on YFP and CFP, respectively, with RFP remaining cytosolic.

FIG. 8C shows an image analysis of HEK293 cells expressing YFPmito-PQR-CFPnls-PQR-RFP demonstrating linear correlations between RFP and YFP fluorescence intensities within difference subcellular compartments. We used mitochondrial (mito) and nuclear (nls) localization signals on YFP and CFP, respectively, with RFP remaining cytosolic.

Figure 8E:
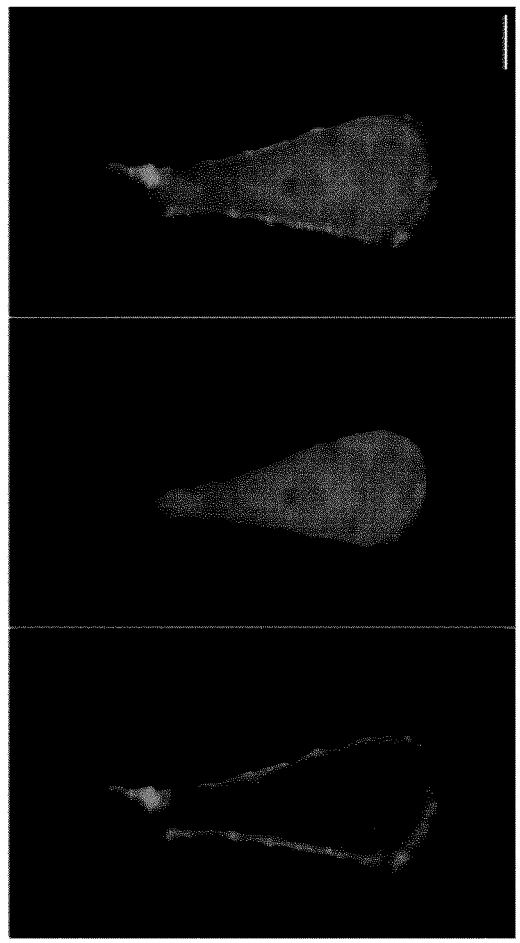
Figure 8D:
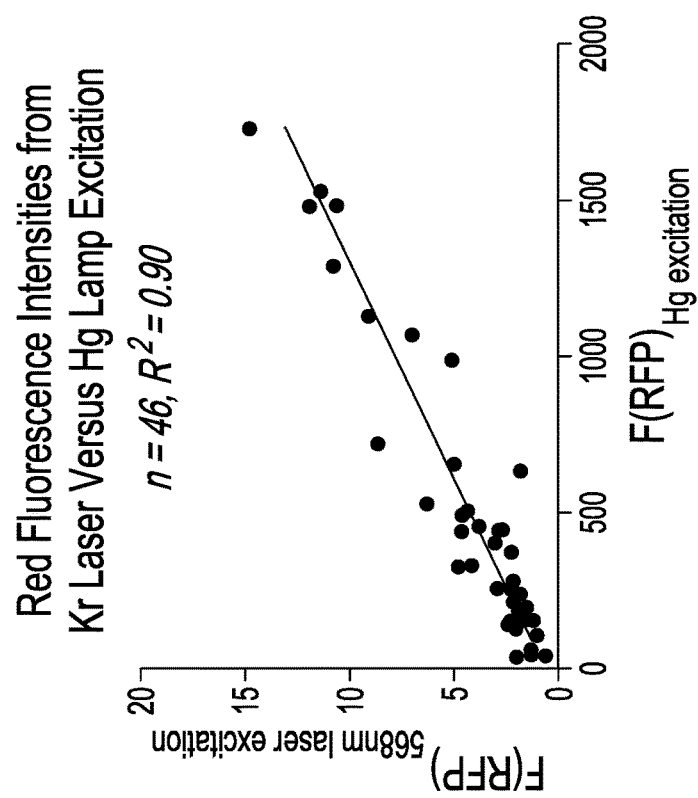

FIG. 8D shows that different fluorescence microscopy methods can be used with PQR. Fluorescence output remains linear between different excitation sources and microscopy methods. HEK293 cells expressing ShakerGFP-PQR-REP were imaged using a spinning disk confocal microscope. Red Fluorescence intensities were highly correlated between excitation methods using a Kr 568nm laser and Hg lamp with $R^2$=0.90(n=46 cells, P<0.001). All excitation methods, fluorophores, and microscopy methods tested produces $R^2$ values ≥0.90 (representative example shown).

FIG. 8E shows that HEK293 cells transfected with RFP-PQR-ShakerGFP did not display inappropriate localization of the Shaker $K^+$ channel, despite the addition of the remaining proline at the N-terminus of the transmembrane channel due to separation of the PQR peptide. These results demonstrate that our PQRs separate robustly regardless of the order or size of the upstream or downstream genes, and that the addition of the N-terminus or C-terminus PQR tags do not interfere with protein function or trafficking.

Figures 9A, 9B, 9C:
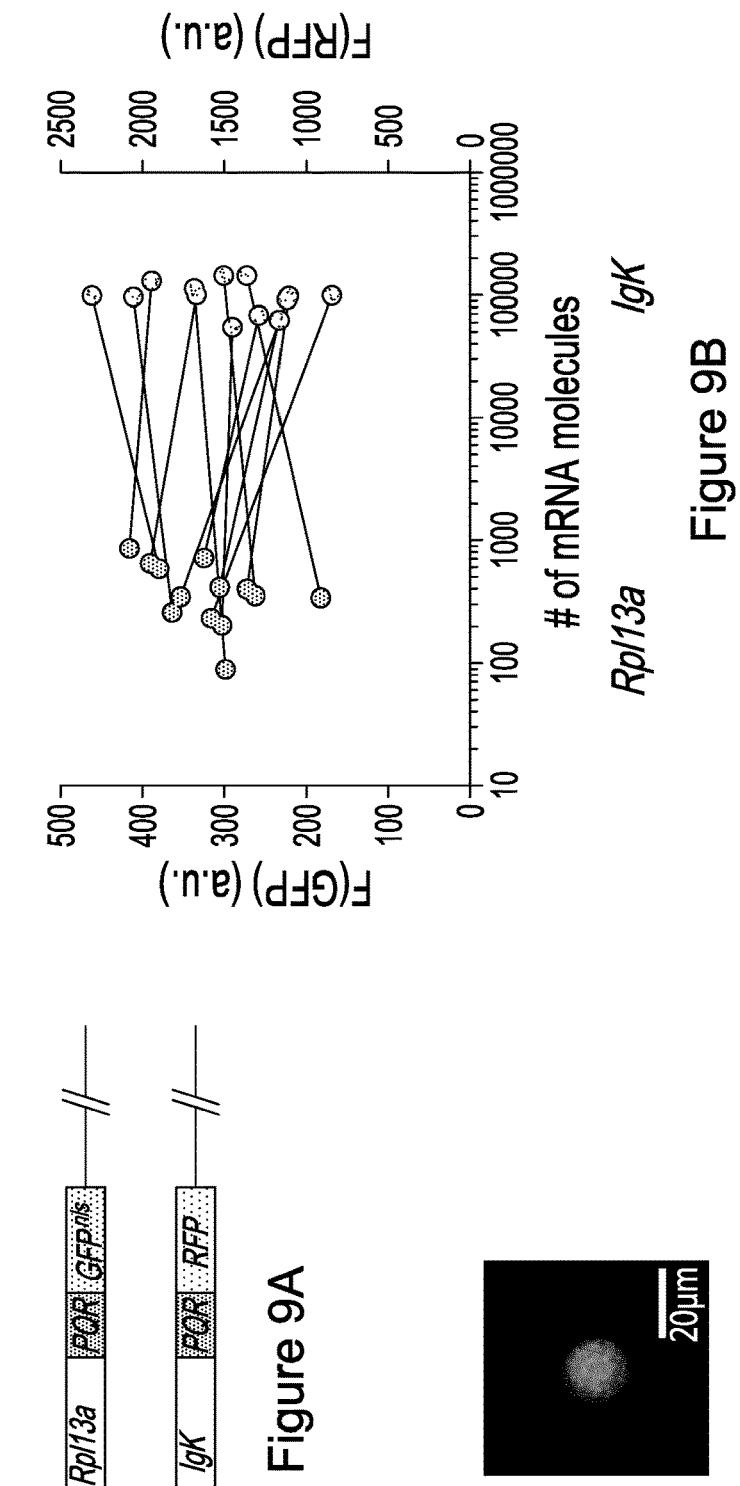

FIG. 9A illustrates that RNA and protein quantitation of both Rpl13a and lgk simultaneously in single living cells using a double knock-in, related to FIG. 6. POQR-GFPnls was inserted into the mouse Rpl13a locus on chromosome 7 using CRISPR-Cas9 genome editing, while PQR-RFP was inserted into the lgk locus on chromosome 6.

FIG. 9B shows that protein expression minimally co-varies with mRNA expression for both genes. The number of RNA transcripts for both genes (x-axis) were measured using qPCR of single cells and green and red fluorescence intensities were measured using a standard fluorescence microscope. Black lines connect the data from the same cell.

FIG. 9C shows a representative example of a double knock-in 22c10 cell expressing GFP in the nucleus and RFP in the cytoplasm, which corresponds to its RPL13A and lgk protein amounts, respectively. Scale bar is 20 µm.

Figure 10A:
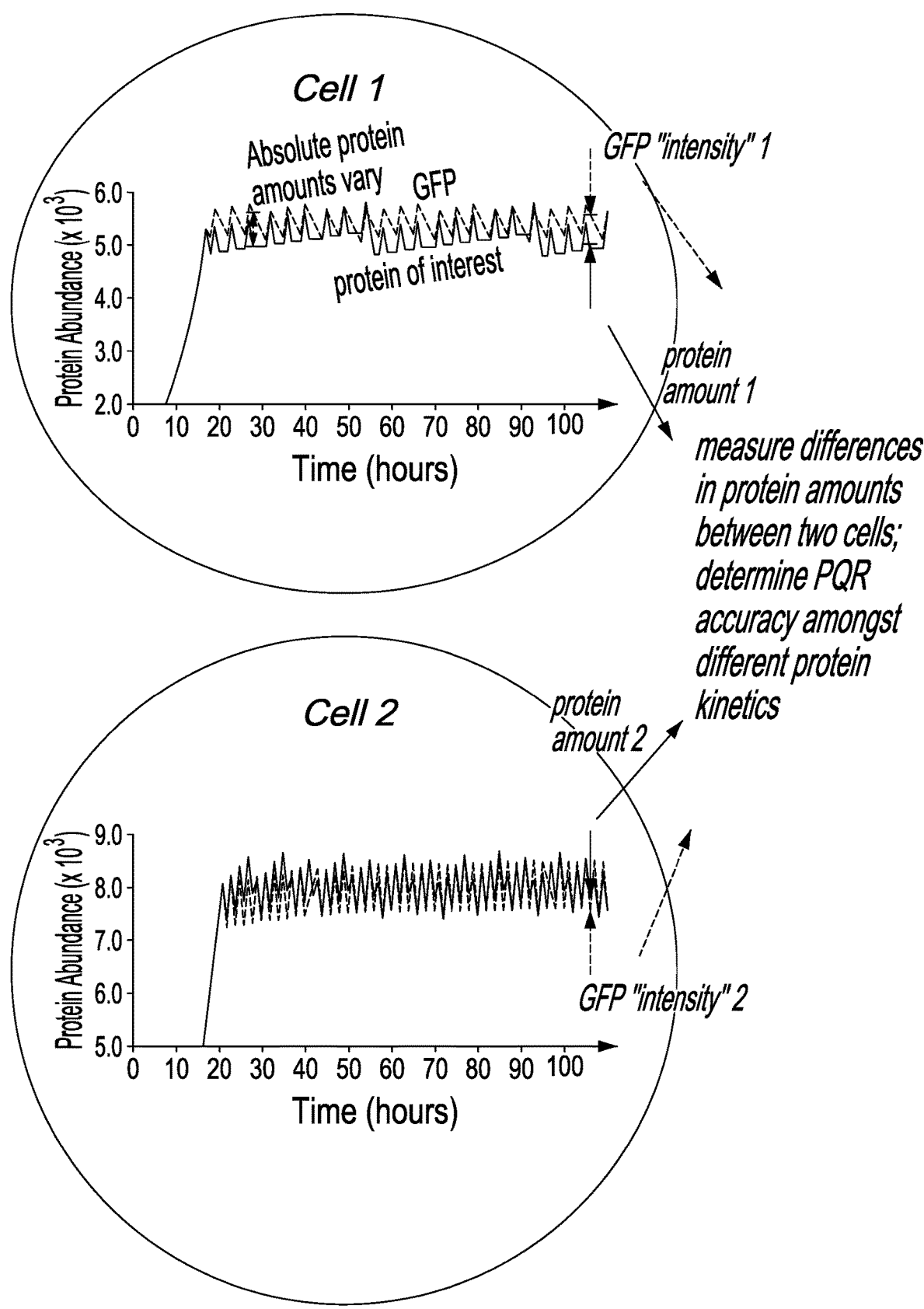

FIG. 10A illustrates that PQR can accurately measure relative protein amounts, related to FIG. 4. Simulation of cells expressing a protein of interest with a PQR. Protein of interest data was modeled from human, mouse, and yeast proteome datasets, and each cell had a random ON and OFF rate, abundance, and lifetime for the protein of interest. PQR-GFP had identical ON rates as well as protein production amounts. When the PQR fluorophore has different kinetics than the protein of interest, absolute protein quantification is inaccurate due to differences in protein turnover (Cell 1, black arrows). By measuring the relative amounts of GFP and comparing this to the relative amounts of the protein of interest, relative protein quantification is highly accurate even for cells with widely varying protein expression (Cell 2, note protein of abundance and kinetics).

Figure 10B:
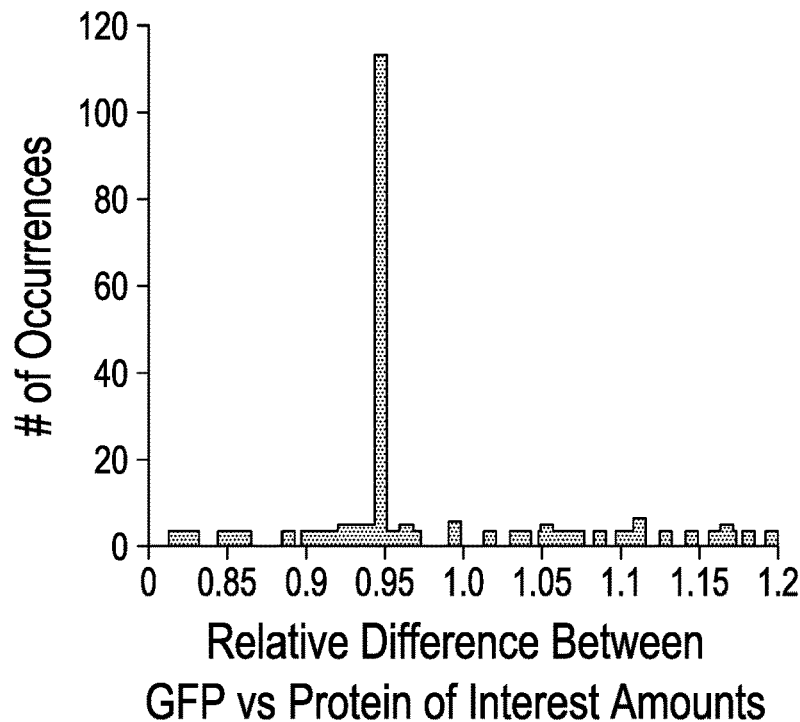

FIG. 10B shows a representative example of histogram of relative differences between GFP and protein of interest measurements over 1,000 trials for the protein in (10A). Relative difference greater than 1 indicate that the PQR-GFP measurement would overestimates of the true protein of interest amount. PQR has >90% accuracy at >85% pf data points across tens of thousands of protein simulations.

Figure 10C:
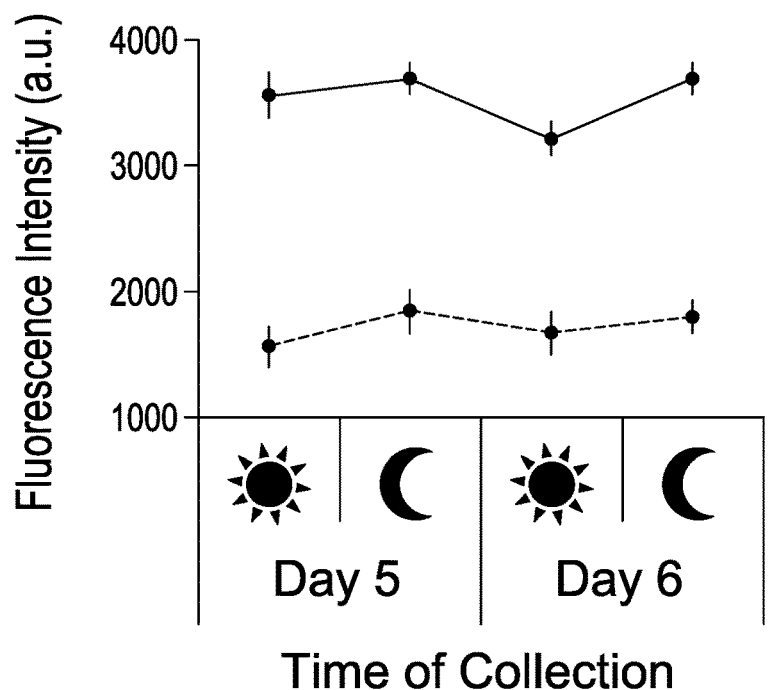

FIG. 10C shows PQR measurements in Drosophila neurons controlling circadian rhythms in phase cycling with PER protein production, at an arbitrary animal age. Small lateral ventral neurons in the Drosophila brain expressing Per-Gal4 to drive UAS—RFP-PQR-PER::YFP were analyzed for yellow (dashed line) and red (full line) fluorescence. Red fluorescence intensity values cycled in phase with yellow fluorescence at Day 5 and 6 when measured with a lower acquisition setting than in FIG. 4. Error bars are S.E.M.

Figures 11A, 11B:
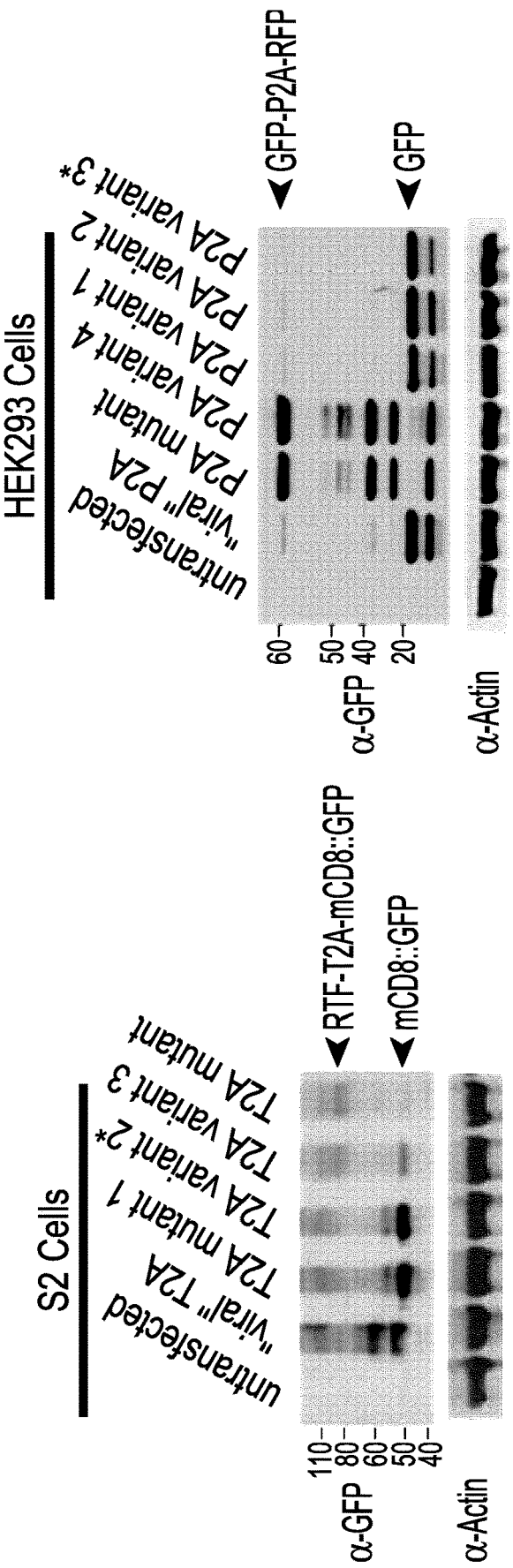

FIG. 11A illustrates the full immuno-blots of different CHYSEL variants and PQR constructs used, related to Experimental Procedures. Screening through different CHYSEL variants from different viruses and within different model ogranism cell lines produced PQR CHYSEL variants with consistent separation of the upstream and downstream proteins. Different cell lines were performed to detect the presence of GFP fused to RFP, and GFP alone. Uncropped blot of T2A-derived sequence variant from FIG. 2. Variant chosen for PQR produces more cleaved protein (lower arrowheads for mCD8::GFP) and less fusion product (upper arrowheads for RFP-T2A-mCD8::GFP). than other CHYSEL peptides. Asterisk denotes the variant chosen as the PQR sequence for experiments (see Example 2 and FIG. 2 legend).

FIG. 11B shows screening of different CHYSEL variants from different viruses and within different model organism cell lines producing PQR CHYSEL variants with consistent separation of the upstream and downstream proteins. Different cell lines were transfected with GFP-CHYSEL-RFP, and Western blots using anti-GFP antibody were performed to detect the presence of GFP fused to RFP, and GFP alone. Uncropped blot of P2A-derived sequence variant from FIG. 2. Variant chosen for PQR produces more cleaved protein (lower arrowheads for GFP) and less fusion product (upper arrowheads for GFP-P2A-RFP) than other CHYSEL peptides. Asterisk denotes the variant chosen as the PQR sequence for experiments (see Example 2 and FIG. 2 legend).

Figures 11C, 11D:
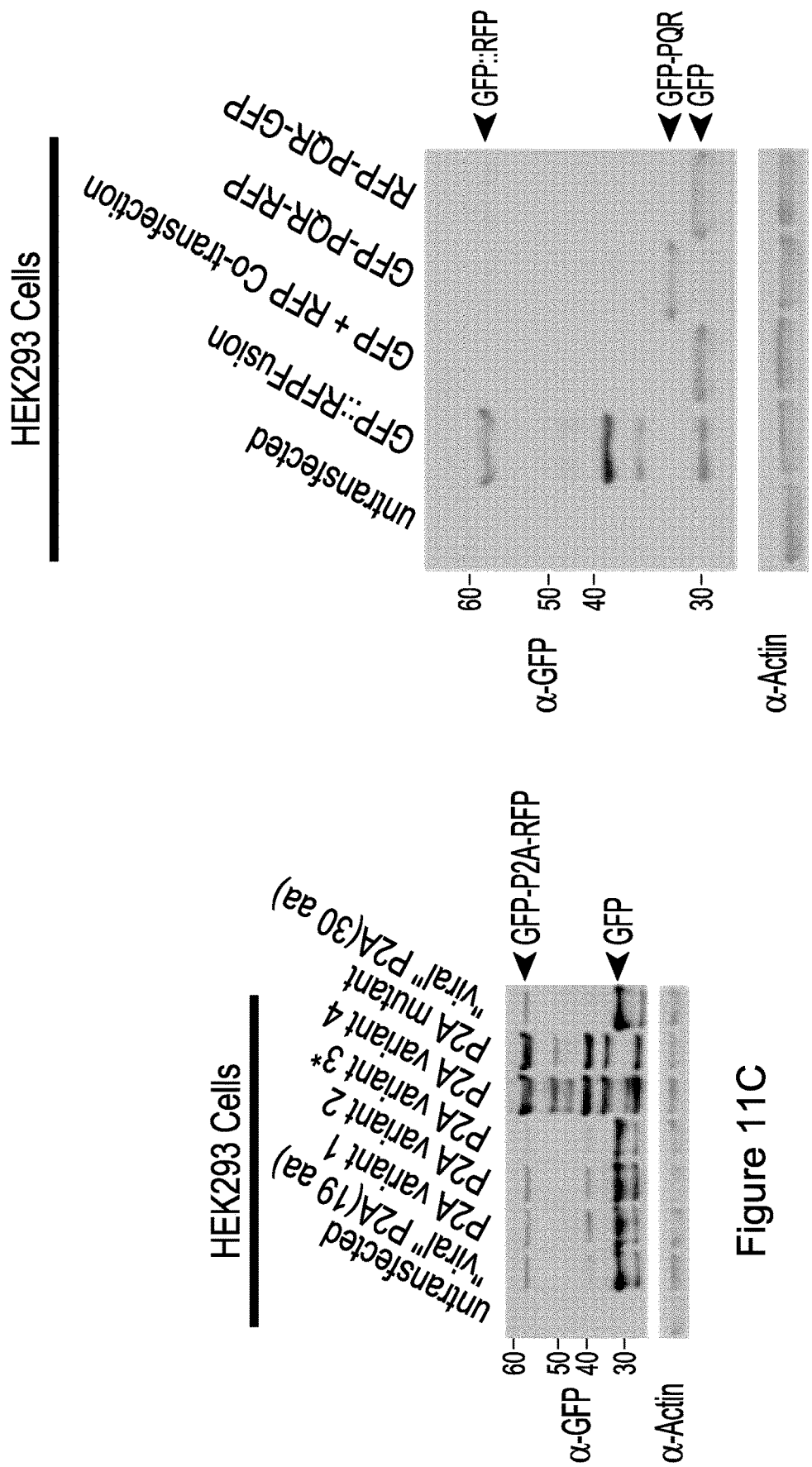

FIG. 11C shows screening of different CHYSEL variants from different viruses and within different model organism cell lines producing PQR CHYSEL variants with consistent separation of the upstream and downstream proteins. Different cell lines were transfected with GFP-CHYSEL-RFP, and Western blots using anti-GFP antibody were performed to detect the presence of GFP fused to RFP, and GFP alone, PQR sequences outperform all other versions of CHYSEL peptides including both short (19 amino acids) and long (30 amino acids) viral sequences.

FIG. 11D shows uncropped immuno-blots on all PQR constructs used in experiments to demonstrate the absence of any fusion protein products that might confound our analysis, HEK293 cells expressing fusion protein GFP::RFP. GFP and RFP plasmids co-transfected. GFP-PQR-RFP, and RFP-PQR-GFP were lysed 5 days after transfection. Collected protein content was analyzed using anti-GFP antibody. Cells that were transfected with either GFP-PQR-RFP or RFP-PQE-GFP produced low or undetectable amounts of fusion product (upper arrow).

Figures 11E, 11F:
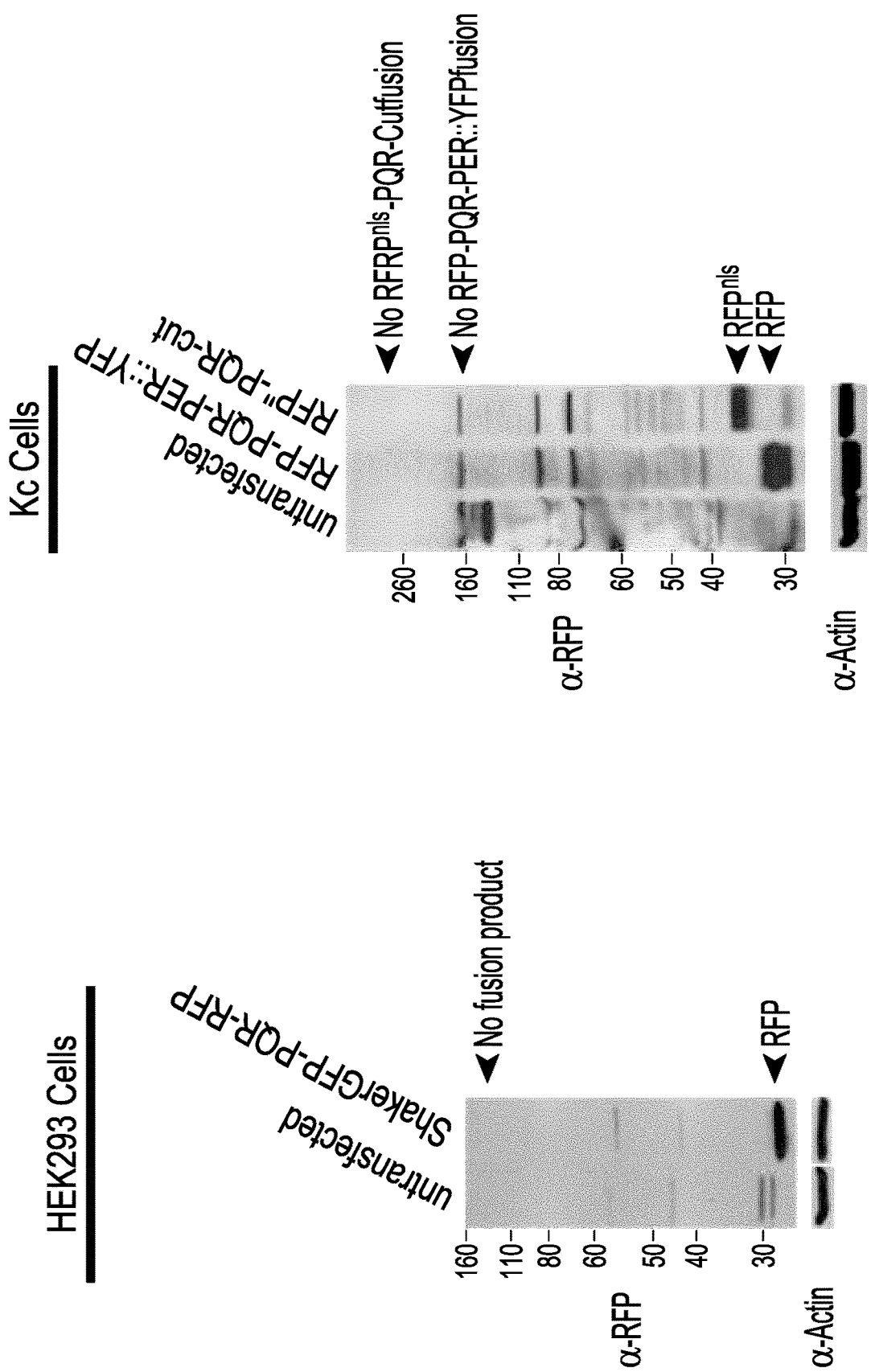

FIG. 11E shows uncropped immuno-blots on all PQR constructs used in experiments to demonstrate the absence of any fusion protein products that might confound our analysis, HEK293 cells expressing ShakerGFP-PQR-RFP were analyzed in Western blots using anti-RFP antibody, and no fusion product was detected.

FIG. 11F shows uncropped immuno-blots on all PQR constructs used in experiments to demonstrate the absence of any fusion protein products that might confound our analysis. Kc cells expressing RFP-PQR-PER::YFP and RFPnls-PQR-cut were analyzed in immuno-blots using anti-RFP antibody. No fusion proteins were produced from either of the two PQR constructs.

Figures 12A, 12B:
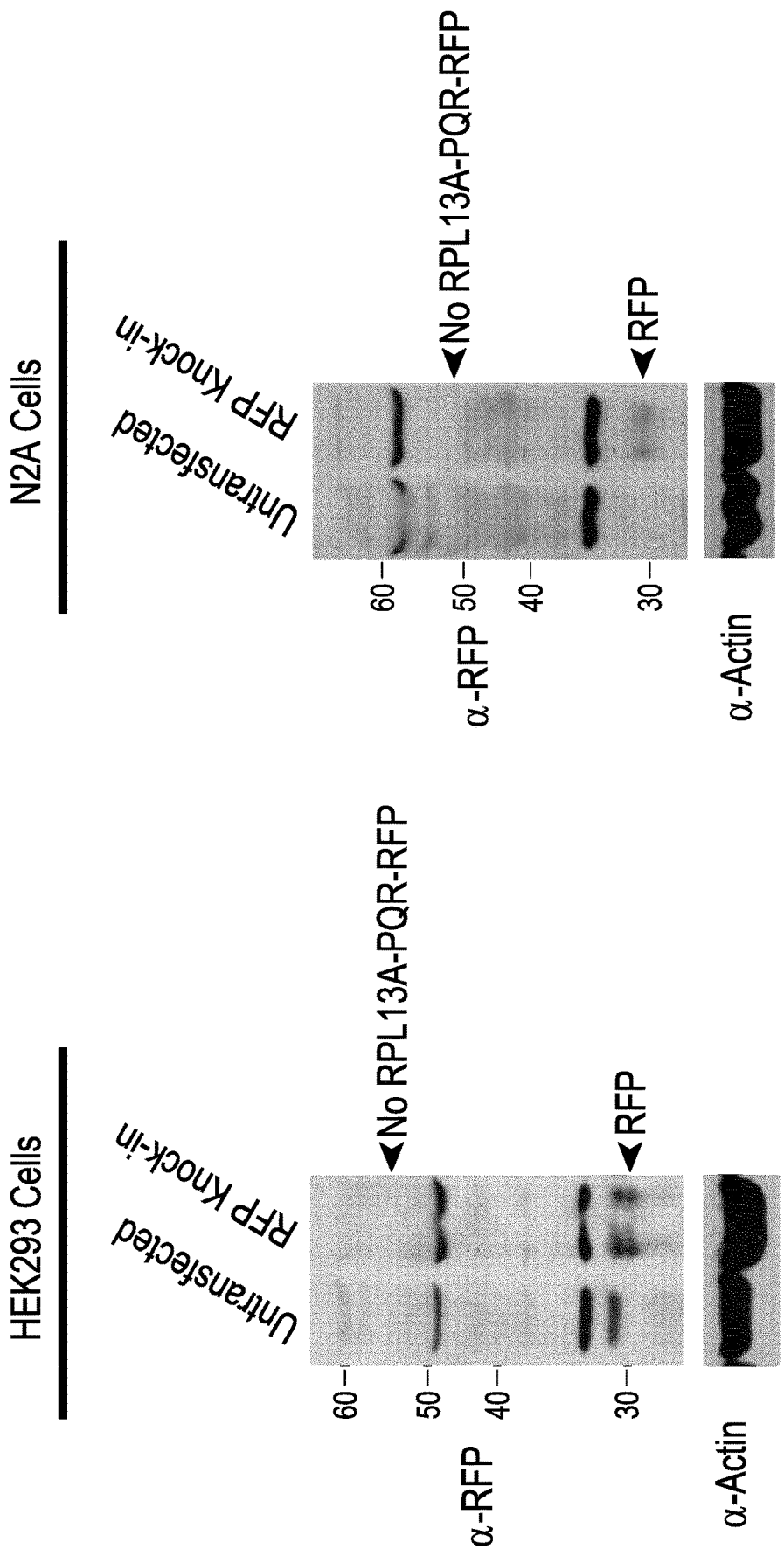

FIG. 12A illustrates that the knock-in of PQR into endogenous loci does not produce fusion proteins nor significantly after the mRNA expression, related to Experimental Procedures. Genome-edited HEK293 cells were lysed and protein content was analyzed using immunoblots against RFP. RFP protein bands were observed, but no fusion protein products were detected.

FIG. 12B illustrates that the knock-in of PQR into endogenous loci does not produce fusion proteins nor significantly alter the mRNA expression, related to Experimental Procedures. Genome-edited N2A cells were lysed and protein content was analyzed using immunoblots against RFP. RFP protein bands were observed, but no fusion protein products were detected.

Figure 12E:
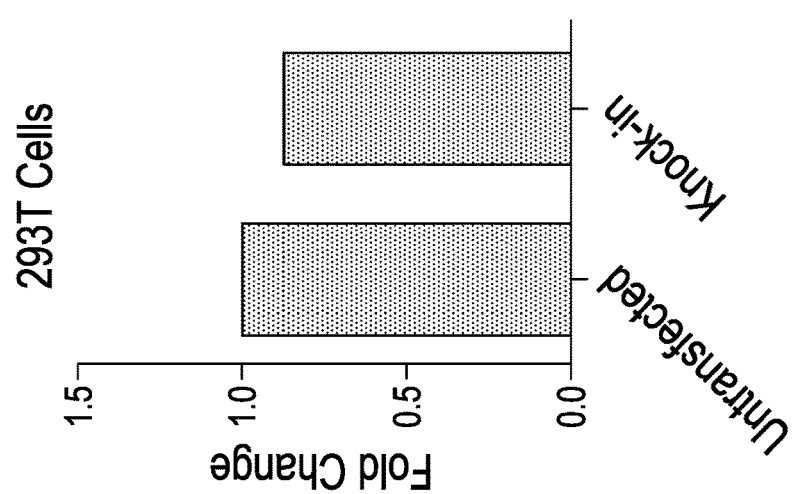
Figure 12D:
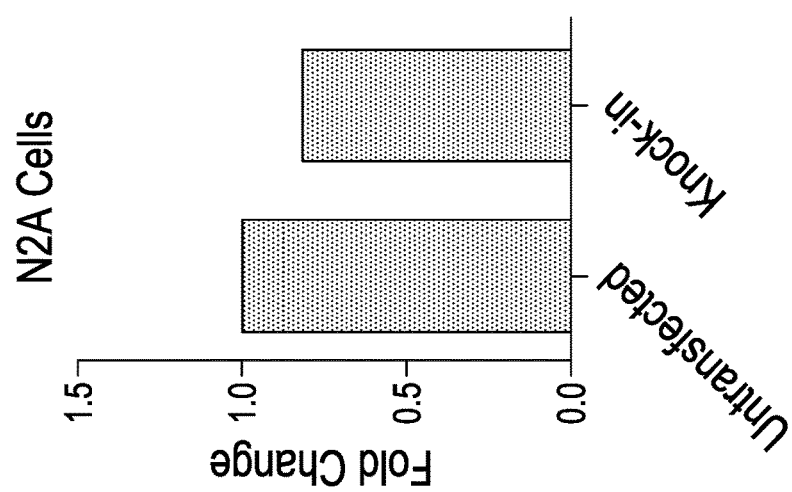
Figure 12C:
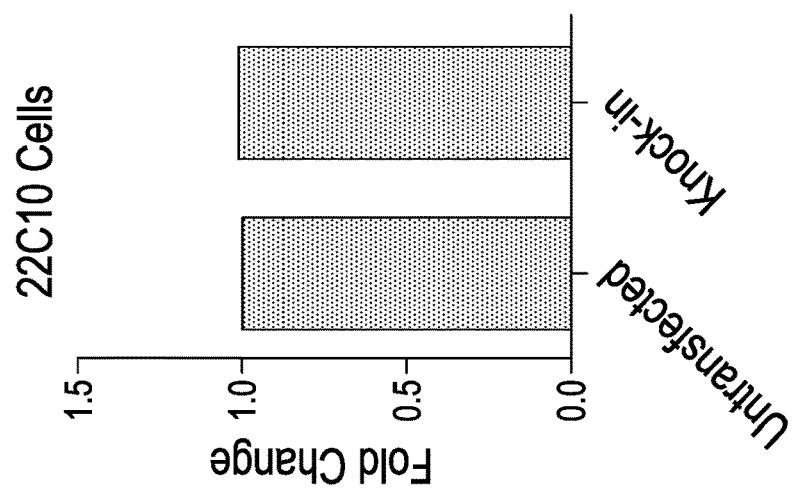

FIG. 12C shows a quantitative real-time PCR analysis of knock-in PQR cells demonstrating that relative levels of mRNA of the PQR-edited gene are not changed. PQR-specific mRNA was measured and normalized to GAPDH mRNA levels and compared as fold changes from the levels in untransfected cells. In 22c10, qPCR experiments were performed in duplicate with technical replicates in duplicate on the lgk loci.

FIG. 12D shows a quantitative real-time PCR analysis of knock-in PQR cells demonstrating that relative levels of mRNA of the PQR-edited gene are not changes. PQR-specific mRNA was measured and normalized to GAPDH mRNA levels and compared as fold changes from the levels in untransfected cells. in N2A cells, experiments were performed in quadruplicate with technical replicates in duplicate on the RPL13A locus.

FIG. 12E shows a quantitative real-time PCR analysis of knock-in PQR cells demonstrating that relative levels of mRNA of the PQR-edited gene are not changed. PQR-specific mRNA was measured and normalized to GAPDH mRNA levels and compared as fold changes from the levels in untransfected cells. In HEK293T (293T) cells, qPCR experiments were performed in duplicate with technical replicates in duplicate on the RPL13A loci.

Figures 13A, 13B:
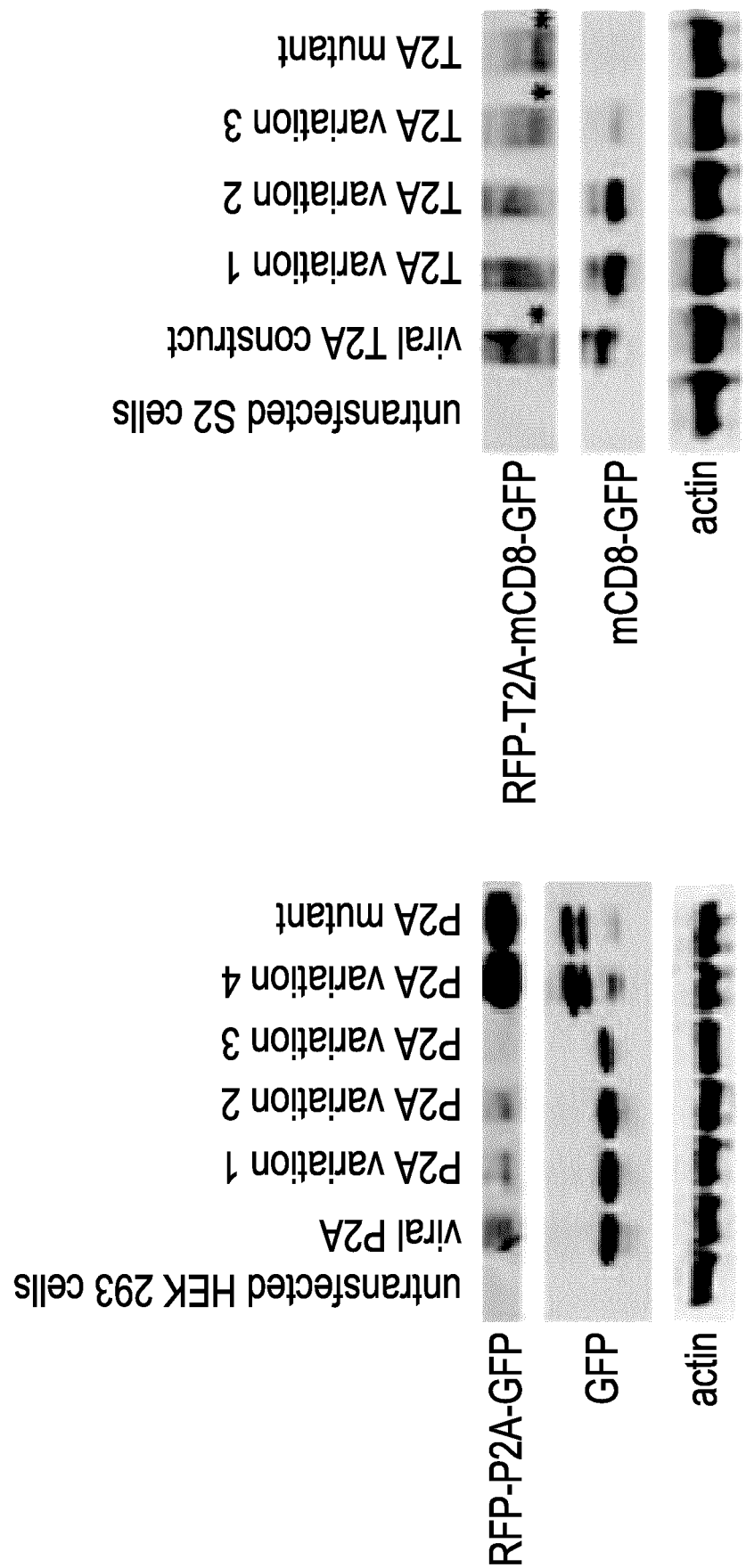

FIG. 13A illustrates the importance of codon de-optimization in the PQR. Western blot results provided as the amount of the fusion protein (RFP-GFP), of the cleaved protein (GFP) and a house-keeping protein (actin) in function of DNA sequence used. "Viral" P2A, variations 1, 2, 3, and 4, correspond to SEQ ID NOs: 5, 6. 10, 11, and 12, respectively.

FIG. 13B shows western blot results provided as the amount of the fusion protein (RFP-GFP), of the cleaved protein (GFP) and a house-keeping protein (actin) in function of DNA sequence used. "Viral" T2A, variations 1, 2, and 3, correspond to SEQ ID NOs: 8, 19, 15, and 16, respectively.

Figure 13D:
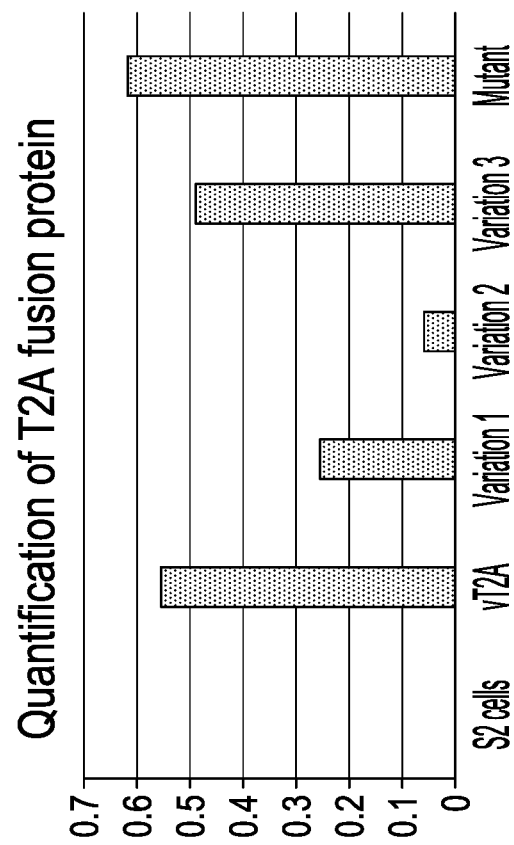
Figure 13C:
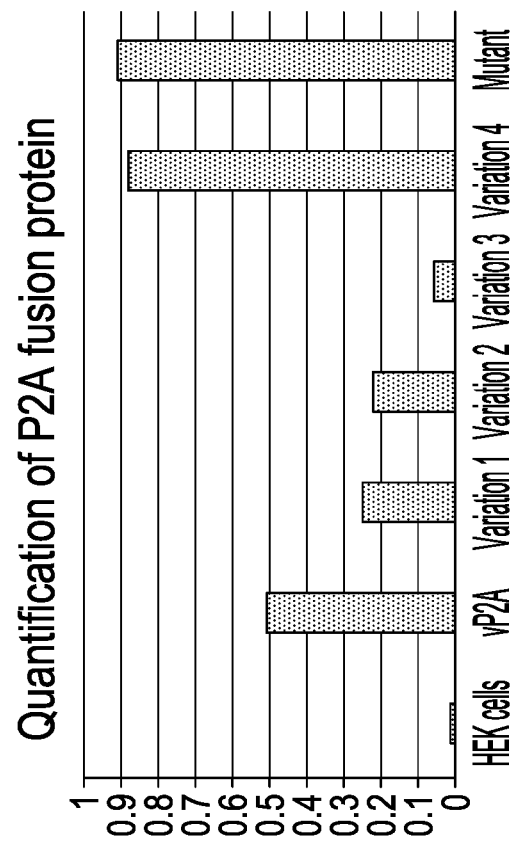

FIG. 13C shows a quantification of western blot results from 13A.

FIG. 13D shows a quantification of western blot results from 13B.

Figure 14A:
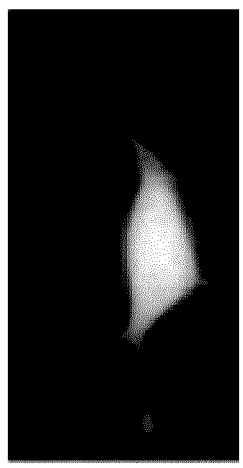
Figure 14A:
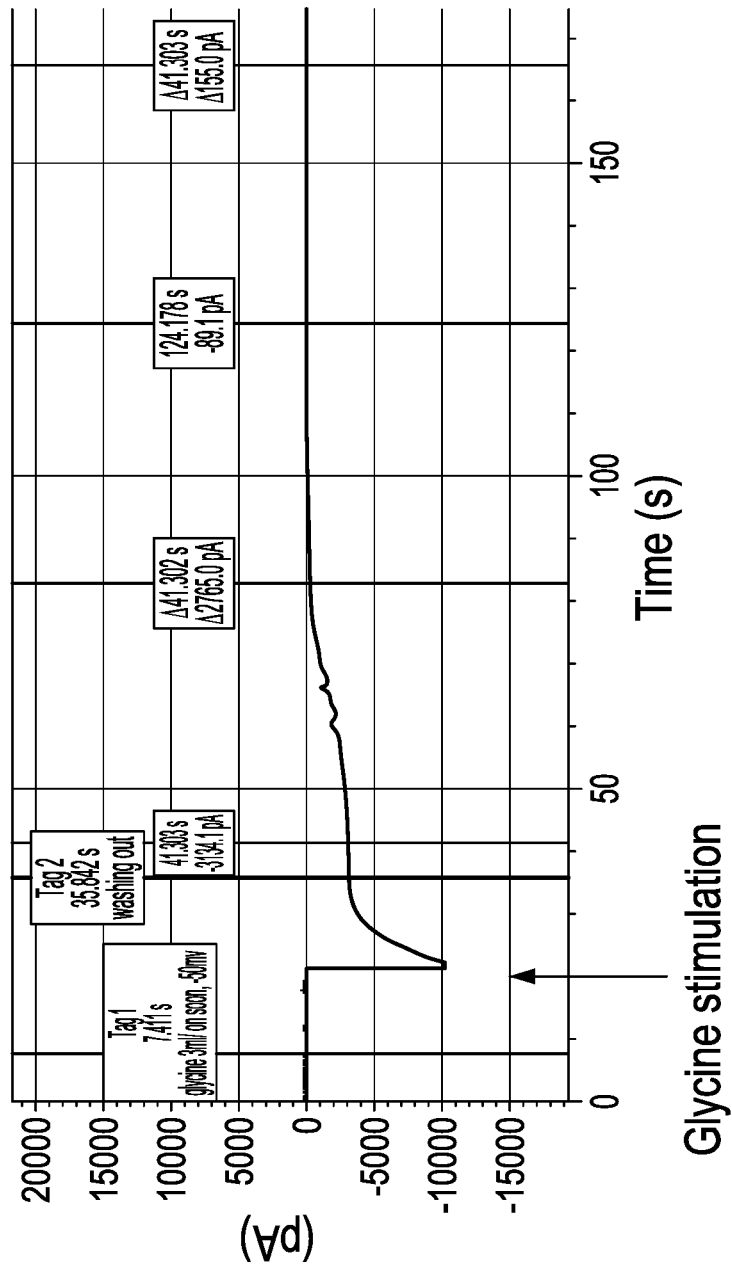

FIG. 14A illustrates modifications of the Glycine-Serine-Glycine (GSG) in CHYSEL peptides. The glycine receptor was expressed with GFP using F2A peptide with a GSG modification (i.e., addition). HEK 293 cells expressing the glycine receptor with the GSG modification were imaged (top panel) and whole cell patch clamp electrophysiology was performed (bottom panel). Cells expressing the gylcine receptor with the GSG modification displayed uniform GFP fluorescent throughout the cell indicating appropriate cleavage of the two proteins, and produces large glycine mediated currents. Scale bar is 10 μm.

Figure 14B:
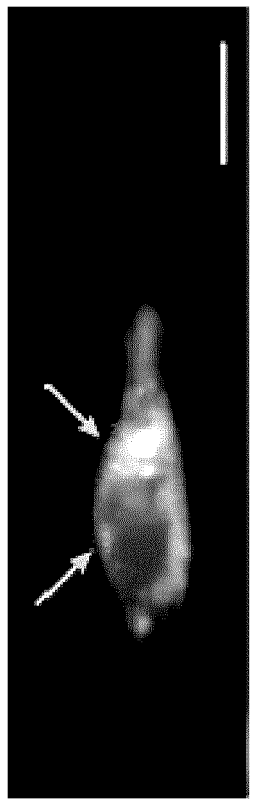
Figure 14B:
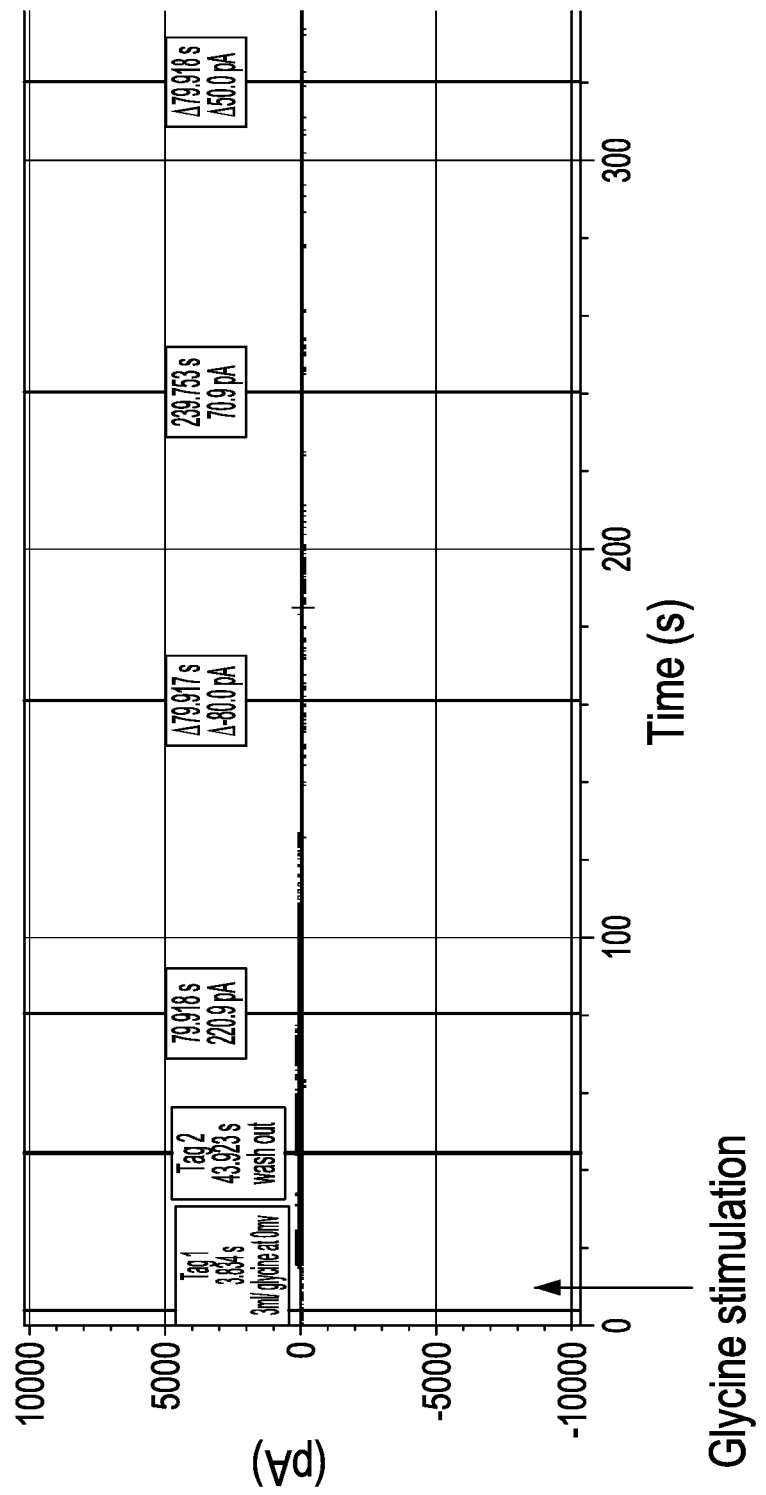

FIG. 14B illustrates modifications of the Glycine-Serine-Glycine (GSG) in CHYSEL peptides. The glycine receptor was expressed without the GSG modification. HEK 293 cells expressing the glycine receptor and GFP without the GSG modification to the CHYSEL peptide contained GFP puncta throughout the cell where the un-cleaved fusion protein was degraded and sequestered within multiple inclusion bodies (top panel, yellow arrows), and produced no detectable Glycine current (bottom panel). Scale bar is 10 μm.

Figure 15A:
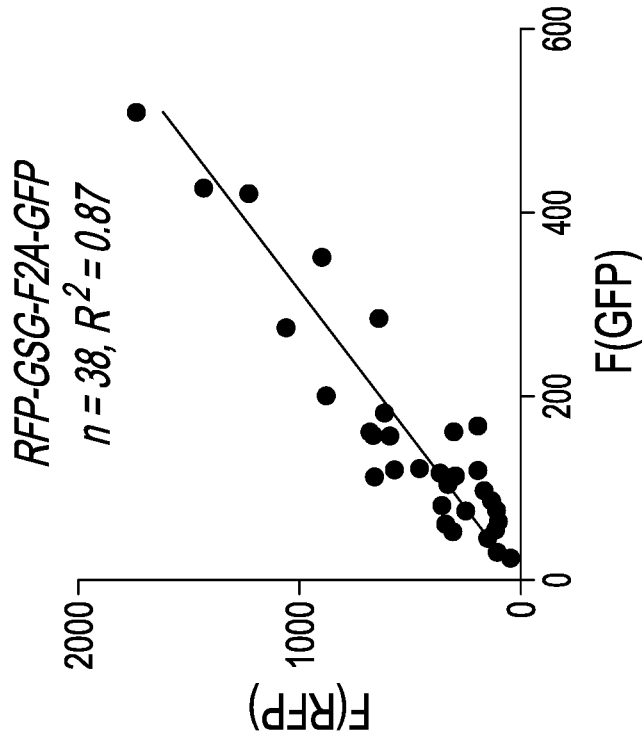

FIG. 15A illustrates similar linear correlations between fluorophores separated using F2A peptide with a GSG modification. Insertion of a GSG-F2A peptide between GFP and RFP produces red and green fluorescence intensities that were linearly correlated. $R^2$ values for GFP-GSG-F2A-RFP were similar to those obtained using P2A and T2A constructs.

Figure 15B:
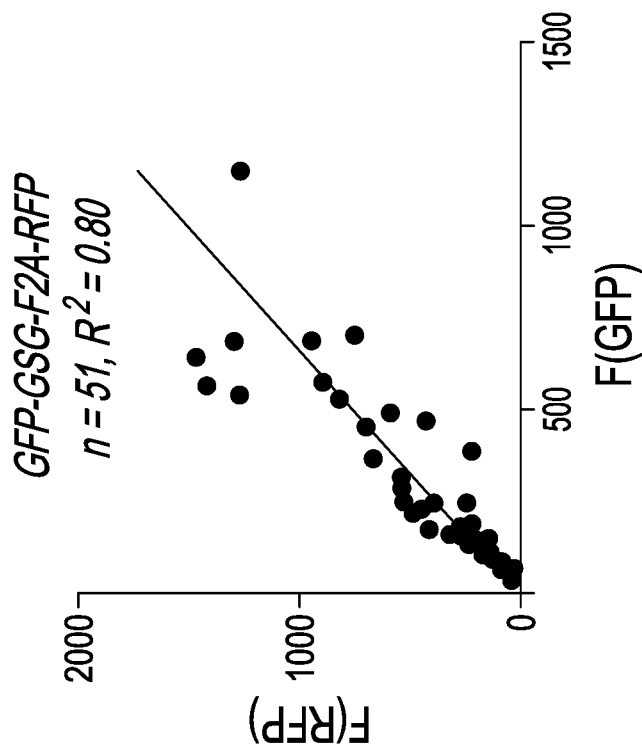

FIG. 15B illustrates similar linear correlations between fluorophores separated using F2A peptide with a GSG modification. Insertion of a GSG-F2A peptide between GFP and RFP produces red and green fluorescence intensities that were linearly correlated. $R^2$ values for GFP-GSG-F2A-RFP were similar to those obtained using P2A and T2A constructs.

Figure 16A:
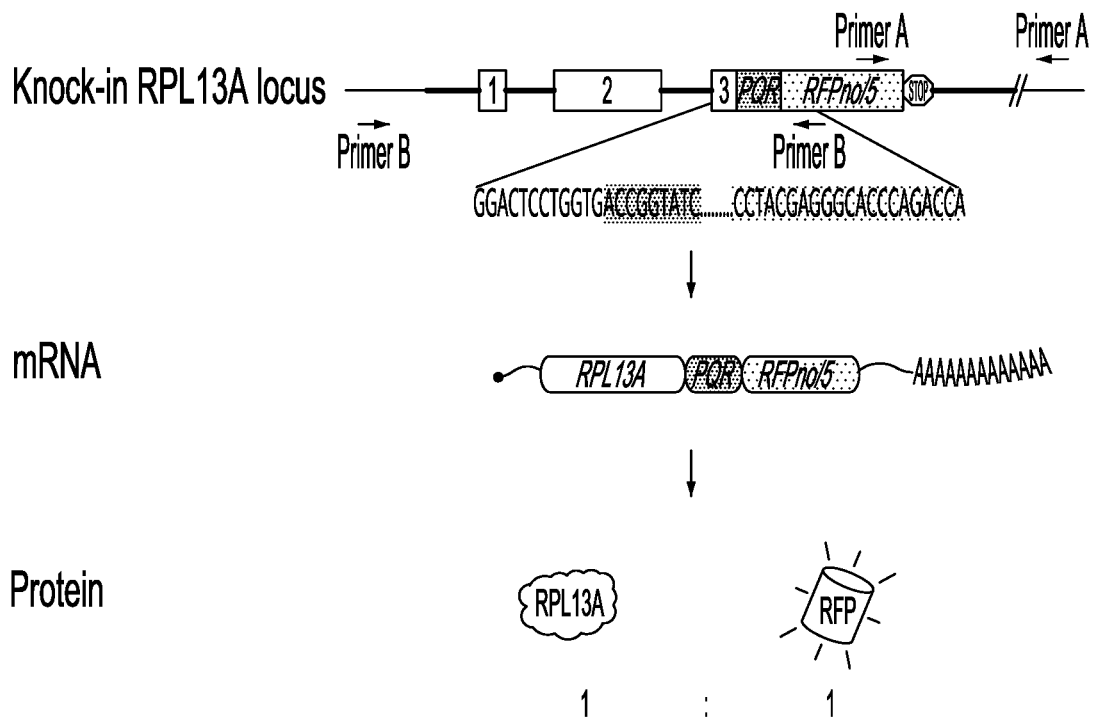

FIG 16A illustrates the design of a RPL13A-PQR-RFP-nols knock-in Drosophila. A knock-in Drosophila expressing the nucleolar RFP (RFPnols) reporter from the endogenous RPL13A locus. Shaded nucleotide sequences represent genomic sequencing results of an edited Drosophila RPL13A gene with a PQR-RFPnols insertion.

Figure 16B:
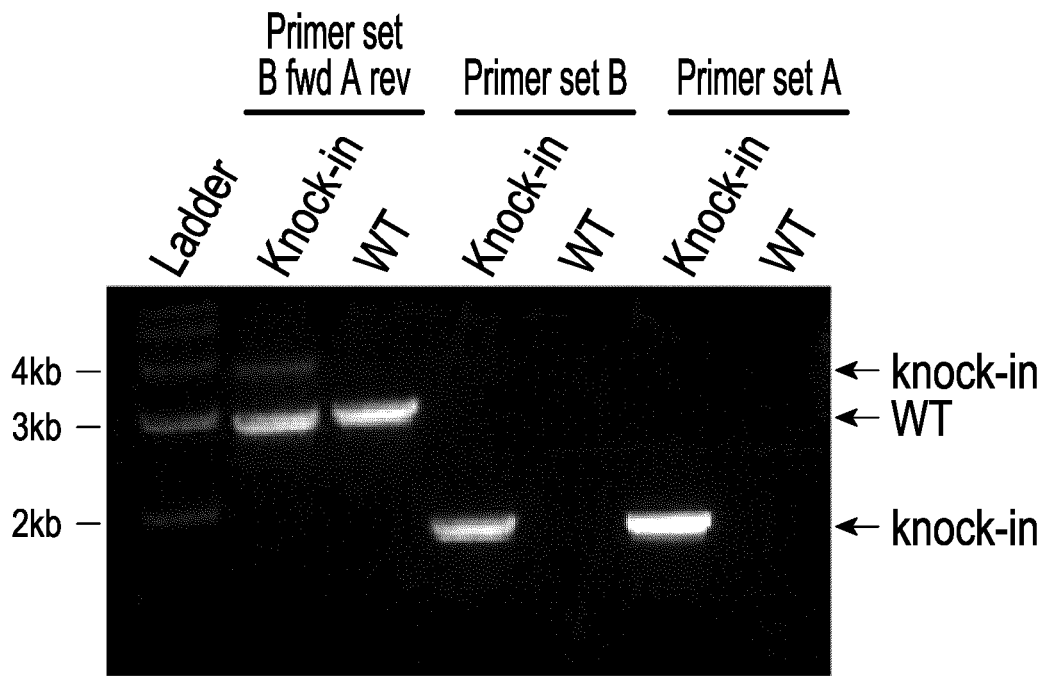

FIG. 16B shows a heterozygous RPL13A-PQR-RFPnols fly verified using genomic PCR genoptyping with primer pairs (see Table 4B) that spanned PQR-RFPnols and outside of the homology arms. For primers spanning outside of homology arms (see Table 4B), PQR-RFPnols allele can produce PCR product size of 3.9 kb (upper arrow), while WT allele resulted in PCR product size of 3 kb (middle arrow). When primer set A or B was used for genotyping, only the knock-in fly produced PCR amplicon of kb 1.8 kb (bottom arrow).

Figure 16C:
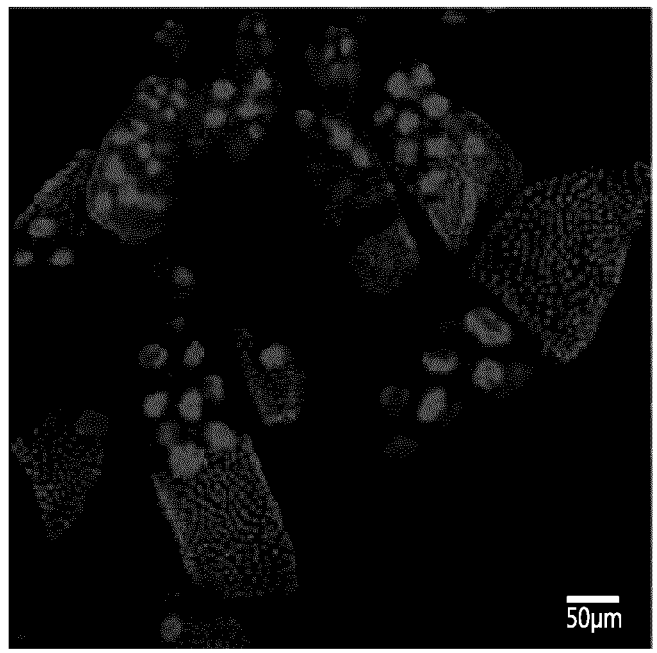

FIG. 16C shows fluorescence micrographs of red nuclei observed from all the cells in embryos. Scale bars are 50 μm.

Figure 16D:
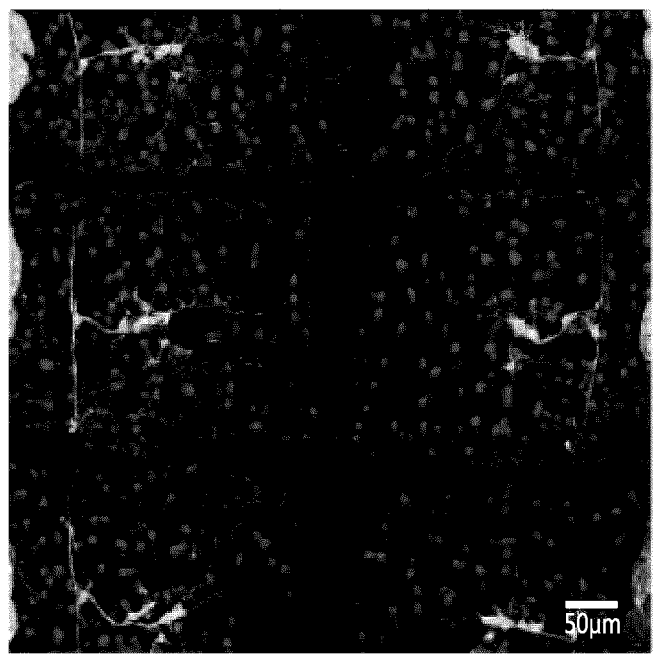

FIG. 16D shows fluorescence micrographs of red nuclei observed from all the cells in larval body walls. Dopamine Neurons labeled in Green were used to visually delineate each segment of an entire larval body. Scale bars are 50 μm.

DETAILED DESCRIPTION

The present disclosure concerns a method of quantifying a protein of interest as well as tools associated thereto. The method relies on the use of a Protein Quantitation Reporter (PQR) linker which is capable of being cleaved during the protein translation of a messenger RNA to quantify a protein of interest. The PQR linker is a nucleic acid molecule encoding a peptide linker located between a reporter protein and the protein of interest. While the messenger RNA encoding the poly-protein is being translated, the PQR peptide linker is cleaved which causes the release, in a stoichiometric ratio, of the reporter protein and the protein of interest. The signal associated with the cleaved reporter protein can be measured to estimate or quantify the protein of interest.

Protein Quantitation Reporter (PQR) Linker

In its broadest embodiment, the PQR linker encodes a cleavable peptide located between two proteins. The PQR linker is intended to be cleaved, during protein translation to produce a stoichiometric ratio of a reporter protein and the protein of interest. In an embodiment, the PQR linker is cleaved at a frequency of at least 95% and, in some further embodiment, the PQR linker is cleaved at a frequency of at least 96%, 97%, 98% or 99%. The signal associated to reporter protein is thus proportional to the amount of protein of interest and is used to determine the relative amount of the protein of interest within the cell.

In an embodiment, the PQR linker encodes a modified cis-acting hydrolase element (CHYSEL) peptide to which a GSG tripeptide has been added to the amino (i.e., $NH_2$) terminus. The CHYSEL peptide includes, at its carboxyl end, a "PGP" tri-peptide. In such embodiment, the PQR linker encodes a cleavable peptide which can be cleaved between the carboxy's penultimate glycine and the carboxy's ultimate proline of the CHYSEL peptide. CHYSEL peptides, also known as "2A" and "2A-like" peptides, come from a broad range of Group IV, positive-sense single stranded RNA viruses such as the in Picornaviridae family including the Aphthoviruses: Equine rhinitis A virus (expressing the E2A peptide), the Foot-and-mouth disease virus (expressing the F2A peptide), and also the Teschovirus: Porcine teschovirus (expressing the P2A peptide). CHYSEL peptides of the 2A-like variety can come from Alphapermutotetraviruses in the Permutotetraviridae family, such as the Thosea asigna (expressing the T2A peptide), or from the Dicistroviridae family such as *Drosophila* C virus (expressing the D2A peptide). Table 1 lists some of the known CHYSEL peptides.

TABLE 1

Viral CHYSEL peptide sequences and associated GSG-modified CHYSEL peptides.

| Organism | Amino acid sequence of known CHYSEL peptide | Amino acid sequence of GSG-modified CHYSEL peptide (SEQ ID NO:) | SEQ ID NO: |
|---|---|---|---|
| EMC-B | GIFNAHYAGYFADLLIHDIETNPGP | *GSG*GIFNAHYAGYFADLLIHDIETNPGP | 27 |
| EMC-D | GIFNAHYAGYFADLLIHDIETNPGP | *GSG*GIFNAHYAGYFADLLIHDIETNPGP | 28 |
| EMC-PV21 | RIFNAHYAGYFADLLIHDIETNPGP | *GSG*RIFNAHYAGYFADLLIHDIETNPGP | 29 |
| MENGO | HVFETHYAGYFSDLLIHDVETNPGP | *GSG*HVFETHYAGYFSDLLIHDVETNPGP | 30 |
| TME-GD7 | KAVRGYHADYYKQRLIHDVEMNPGP | *GSG*KAVRGYHADYYKQRLIHDVEMNPGP | 31 |
| TME-DA | RAVRAYHADYYKQRLIHDVEMNPGP | *GSG*RAVRAYHADYYKQRLIHDVEMNPGP | 32 |
| TME-BEAN | KAVRGYHADYYRQRLIHDVETNPGP | *GSG*KAVRGYHADYYRQRLIHDVETNPGP | 33 |

TABLE 1-continued

Viral CHYSEL peptide sequences and associated GSG-modified CHYSEL peptides.

| Organism | Amino acid sequence of known CHYSEL peptide | Amino acid sequence of GSG-modified CHYSEL peptide (SEQ ID NO:) | SEQ ID NO: |
|---|---|---|---|
| Theiler's-Like Virus | KHVREYHAAYYKQRLMHDVETNPGP | GSGKHVREYHAAYYKQRLMHDVETNPGP | 34 |
| Ljungan virus (174F) | MHSDEMDFAGGKFLNQCGDVETNPGP | GSGMHSDEMDFAGGKFLNQCGDVETNPGP | 35 |
| Ljungan virus (145SL) | MHNDEMDYSGGKFLNQCGDVESNPGP | GSGMHNDEMDYSGGKFLNQCGDVESNPGP | 36 |
| Ljungan virus (87-012) | MHSDEMDFAGGKFLNQCGDVETNPGP | GSGMHSDEMDFAGGKFLNQCGDVETNPGP | 37 |
| Ljungan virus (M1146) | YHDKDMDYAGGKFLNQCGDVETNPGP | GSGYHDKDMDYAGGKFLNQCGDVETNPGP | 38 |
| FMD-A10 | LLNFDLLKLAGDVESNPGP | GSGLLNFDLLKLAGDVESNPGP | 39 |
| FMD-A12 | LLNFDLLKLAGDVESNPGP | GSGLLNFDLLKLAGDVESNPGP | 40 |
| FMD-C1 | LLNFDLLKLAGDVESNPGP | GSGLLNFDLLKLAGDVESNPGP | 41 |
| FMD-O1G | LLNFDLLKLAGDMESNPGP | GSGLLNFDLLKLAGDMESNPGP | 42 |
| FMD-O1K | LTNFDLLKLAGDVESNPGP | GSGLTNFDLLKLAGDVESNPGP | 43 |
| FMD-O (Taiwan) | LLNFDLLKLAGDVESNPGP | GSGLLNFDLLKLAGDVESNPGP | 44 |
| FMD-O/SK | LLSFDLLKLAGDVESNPGP | GSGLLSFDLLKLAGDVESNPGP | 45 |
| FMD-SAT3 | MCNFDLLKLAGDVESNPGP | GSGMCNFDLLKLAGDVESNPGP | 46 |
| FMD-SAT2 | LLNFDLLKLAGDVESNPGP | GSGLLNFDLLKLAGDVESNPGP | 47 |
| ERAV | CTNYSLLKLAGDVESNPGP | GSGCTNYSLLKLAGDVESNPGP | 48 |
| ERBV | GATNFSLLKLAGDVELNPGP | GSGGATNFSLLKLAGDVELNPGP | 49 |
| ERV-3 | GATNFDLLKLAGDVESNPGP | GSGGATNFDLLKLAGDVESNPGP | 50 |
| PTV-1 | GPGATNFSLLKQAGDVEENPGP | GSGGPGATNFSLLKQAGDVEENPGP | 51 |
| PTV-2 | GPGATNFSLLKQAGDVEENPGP | GSGGPGATNFSLLKQAGDVEENPGP | 52 |
| PTV-3 | GPGASSFSLLKQAGDVEENPGP | GSGGPGASSFSLLKQAGDVEENPGP | 53 |
| PTV-4 | GPGASNFSLLKQAGDVEENPGP | GSGGPGASNFSLLKQAGDVEENPGP | 54 |
| PTV-5 | GPGAANFSLLRQAGDVEENPGP | GSGGPGAANFSLLRQAGDVEENPGP | 55 |
| PTV-6 | GPGATNFSLLKQAGDVEENPGP | GSGGPGATNFSLLKQAGDVEENPGP | 56 |
| PTV-7 | GPGATNFSLLKQAGDVEENPGP | GSGGPGATNFSLLKQAGDVEENPGP | 57 |
| PTV-8 | GPGATNFSLLKQAGDIEENPGP | GSGGPGATNFSLLKQAGDIEENPGP | 58 |
| PTV-9 | GPGATNFSLLKQAGDVEENPGP | GSGGPGATNFSLLKQAGDVEENPGP | 59 |
| PTV-10 | GPGATNFSLLKQAGDVEENPGP | GSGGPGATNFSLLKQAGDVEENPGP | 60 |
| PTV-11 | GPGATNFSLLKRAGDVEENPGP | GSGGPGATNFSLLKRAGDVEENPGP | 61 |
| CrPV | FLRKRTQLLMSGDVESNPGP | GSGFLRKRTQLLMSGDVESNPGP | 62 |
| DCV | EAARQMLLLLSGDVETNPGP | GSGEAARQMLLLLSGDVETNPGP | 63 |
| ABPV | GSWTDILLLLSGDVETNPGP | GSGGSWTDILLLLSGDVETNPGP | 64 |
| ABPV isolate Poland 1 | GSWTDILLLLSGDVETNPGP | GSGGSWTDILLLLSGDVETNPGP | 65 |
| ABPV isolate Hungary 1 | GSWTDILLLWSGDVETNPGP | GSGGSWTDILLLWSGDVETNPGP | 66 |
| IFV | TRAEIEDELIRAGIESNPGP | GSGTRAEIEDELIRAGIESNPGP | 67 |
| TaV | RAEGRGSLLTCGDVEENPGP | GSGRAEGRGSLLTCGDVEENPGP | 68 |
| EEV | QGAGRGSLVTCGDVEENPGP | GSGQGAGRGSLVTCGDVEENPGP | 69 |
| APV | NYPMPEALQKIIDLESNPPP | GSGNYPMPEALQKIIDLESNPPP | 70 |

TABLE 1-continued

Viral CHYSEL peptide sequences and associated GSG-modified CHYSEL peptides.

| Organism | Amino acid sequence of known CHYSEL peptide | Amino acid sequence of GSG-modified CHYSEL peptide (SEQ ID NO:) | SEQ ID NO: |
|---|---|---|---|
| KBV | GTWESVLNLLAGDIELNPGP | *GSG*GTWESVLNLLAGDIELNPGP | 71 |
| PnPV (a) | AQGWVPDLTVDGDVESNPGP | *GSG*AQGWVPDLTVDGDVESNPGP | 72 |
| PnPV (b) | IGGGQKDLTQDGDIESNPGP | *GSG*IGGGQKDLTQDGDIESNPGP | 73 |
| Ectropis oblique picorna-like virus (A) | AQGWAPDLTQDGDVESNPGP | *GSG*AQGWAPDLTODGDVESNPGP | 74 |
| Ectropis obliqua picorna-like virus (B) | IGGGQRDLTQDGDIESNPGP | *GSG*IGGGQRDLTQDGDIESNPGP | 75 |
| Providence virus (a) | VGDRGSLLTCGDVESNPGP | *GSG*VGDRGSLLTCGDVESNPGP | 76 |
| Providence virus (b) | SGGRGSLLTAGDVEKNPGP | *GSG*SGGRGSLLTAGDVEKNPGP | 77 |
| Providence virus (c) | GDPIEDLTDDGDIEKNPGP | *GSG*GDPIEDLTDDGDIEKNPGP | 78 |
| Bovine Rotavirus | SKFQIDRILISGDIELNPGP | *GSG*SKFQIDRILISGDIELNPGP | 79 |
| Porcine Rotavirus | AKFQIDKILISGDVELNPGP | *GSG*AKFQIDKILISGDVELNPGP | 80 |
| Human Rotavirus | SKFQIDKILISGDIELNPGP | *GSG*SKFQIDKILISGDIELNPGP | 81 |

As indicated above, the PQR linker encodes a "modified" CHYSEL peptide in which the tripeptide "GSG" has been added to the amino (i.e.g, NH$_2$) terminus of the wild-type CHYSEL peptide. In an embodiment, the PQR linker encodes any CHYSEL peptide listed in Table 1 to which the tripeptide "GSG" has been added to the amino terminus (such as those listed in the third column of Table 1).

In another embodiment, the PQR linker encodes a peptide encompassed in the consensus sequence of a CHYSEL peptide which has been modified to bear a "GSG" tripeptide at the amino (NH$_2$) terminus. Table 2 provides a comparison of various CHYSEL peptides as well as associated consensus sequences. For example, the PQR linker can encode a peptide encompassed in the consensus sequence from the F2A, E2A, T2A and P2A peptides (as shown in the amino acid sequence of SEQ ID NO: 21, 5$^{th}$ entry on Table 2) to which as GSG tripeptide has been added (as shown in the amino acid sequence of SEQ ID NO: 23).

(SEQ ID NO: 21)
$X_1X_2X_3X_4X_5X_6X_7X_8X_9LX_{10}X_{11}X_{12}GDVEX_{13}NPGP$ (SEQ ID NO: 23)
$GSGX_1X_2X_3X_4X_5X_6X_7X_8X_9LX_{10}X_{11}X_{12}GDVEX_{13}NPGP$

In both the amino acid sequences of SEQ ID NO: 21 and 23, $X_1$ is V or absent; $X_2$ is K or absent; $X_3$ is Q or absent; $X_4$ is T, C, A or absent; $X_5$ is L, T or E; $X_6$ is N or G; $X_7$ is F, Y or R; $X_8$ is D, A, G or S; $X_9$ is L or S; $X_{10}$ is K or L; $X_{11}$ is L, T or Q; $X_{12}$ is A or C and $X_{13}$ is S or E.

TABLE 2

Comparison of CHYSEL peptides reveals a conserved sequence of amino acids (taken from Szymczak et al., 2004). First line corresponds to the F2A peptide, second line corresponds to the E2A peptide, third line corresponds to the T2A peptide and the fourth line corresponds to the P2A peptide. The fifth line corresponds to the consensus sequence obtained from comparing the F2A, E2A, T2A and P2A peptides. The sixth line corresponds to the consensus obtained from comparing T2A and P2A peptides.

| Description | -21 | -20 | -19 | -18 | -17 | -16 | -15 | -14 | -13 | -12 | -11 | -10 | -9 | -8 | -7 | -6 | -5 | -4 | -3 | -2 | -1 | 0 |
|---|---|---|---|---|---|---|---|---|---|---|---|---|---|---|---|---|---|---|---|---|---|---|
| F2A (SEQ ID NO: 17) | V | K | Q | T | L | N | F | D | L | L | K | L | A | G | D | V | E | S | N | P | G | P |
| E2A (SEQ ID NO: 18) | — | — | Q | C | T | N | Y | A | L | L | K | L | A | G | D | V | E | S | N | P | G | P |
| T2A (SEQ ID NO: 19) | — | — | — | — | E | G | R | G | S | L | L | T | C | G | D | V | E | E | N | P | G | P |
| P2A (SEQ ID NO: 20) | — | — | — | A | T | N | F | S | L | L | K | Q | A | G | D | V | E | E | N | P | G | P |
| Consensus (all) (SEQ ID NO: 21) | | $X_1$ | $X_2$ | $X_3$ | $X_4$ | $X_5$ | $X_6$ | $X_7$ | $X_8$ | $X_9$ | L | $X_{10}$ | $X_{11}$ | $X_{12}$ | G | D | V | E | $X_{13}$ | N | P | G | P |
| Consensus T2A/P2A (SEQ ID NO: 22) | — | — | — | $X_{14}$ | $X_{15}$ | $X_{16}$ | $X_{17}$ | $X_{18}$ | $X_{19}$ | L | $X_{20}$ | $X_{21}$ | $X_{22}$ | G | D | V | E | E | N | P | G | P |

In another example, the PQR linker can encode a peptide encompassed in the consensus sequence from the T2A and P2A peptides (as shown in the amino acid sequence of SEQ ID NO: 22, 6$^{th}$ entry on Table 2) to which as GSG tripeptide has been added (as shown in the amino acid sequence of SEQ ID NO: 24):

$X_{14}X_{15}X_{16}X_{17}X_{18}X_{19}LX_{20}X_{21}X_{22}$GDVEENPGP (SEQ ID NO: 22)

GSG$X_{14}X_{15}X_{16}X_{17}X_{18}X_{19}LX_{20}X_{21}X_{22}$GDVEENPGP (SEQ ID NO: 24)

In both the amino acid sequences of SEQ ID NO: 22 and 24, $X_{14}$ is A or absent; $X_{15}$ is E or T; $X_{16}$ is G or N; $X_{17}$ is R or F; $X_{18}$ is G or S; $X_{19}$ is S or L; $X_{20}$ is L or K; $X_{21}$ is T or Q and $X_{22}$ is C or A.

In some embodiments, the PQR can include one or more additional amino acids of the CHYSEL peptide which is/are found upstream (from the N-terminus) of those presented in Table 2. For example, the PQR can include up to 11 additional amino acids found upstream of the amino acid sequences shown in Table 2. If the PQR includes one or more of upstream amino acid, it also should include a "GSG" tri-peptide linker at its N-terminal end. Exemplary longer CHYSEL peptides are can have the amino acid sequence of SEQ ID NO: 96 to which a "GSG" tri-peptide linker has been added at its N-terminal end.

In yet a further embodiment, the PQR linker can encode the P2A peptide from the porcine teschovirus-1 (SEQ ID NO: 1) modified to bear the GSG tripeptide (SEQ ID NO: 3). In still a further embodiment, the PQR linker can encode the T2A peptide from the Thosea asigna insect virus (SEQ ID NO: 2) modified to bear the GSG tripeptide (SEQ ID NO: 26).

In the context of the present disclosure, the PQR linker is a nucleic acid molecule which encodes the cleavable peptide disclosed herein and is capable of being transcribed into a messenger RNA molecule. The PQR linker molecules can have the generic nucleic acid sequence set forth in SEQ ID NO: 25:

(SEQ ID NO: 25)
$N_1N_2N_3$ $N_4N_5N_6$ $N_7N_8N_9$ $N_{10}N_{11}N_{12}$ $N_{13}N_{14}N_{15}$ $N_{16}N_{17}$ $N_{18}$ $N_{19}N_{20}N_{21}$ $N_{22}N_{23}N_{24}$ $N_{25}N_{26}N_{27}N_{28}N_{29}N_{30}$ $N_{31}$ $N_{32}N_{33}$ $N_{34}N_{35}N_{36}$ $N_{37}N_{38}N_{39}$ $N_{40}N_{41}N_{42}$ $N_{43}N_{44}N_{45}$ $N_{46}$ $N_{47}N_{48}$ $N_{49}N_{50}N_{51}N_{52}N_{53}N_{54}N_{55}N_{56}N_{57}$ $N_{58}N_{59}$ $N_{60}$ $N_{61}N_{62}N_{63}$ AAY CC$N_{64}$ GGA CC$N_{65}$

In the nucleic acid sequence of SEQ ID: 25, $N_1$ to $N_{63}$ represent any nucleic acid capable of forming codons encoding the subsequence GSG$X_1X_2X_3X_4X_5X_6X_7X_8X_9LX_{10}X_{11}X_{12}$GDVE$X_{13}$ of SEQ ID NO: 23 (corresponding to residues 1 to 21 of SEQ ID NO: 23) or the subsequence GSG$X_{14}X_{15}X_{16}X_{17}X_{18}X_{19}LX_{20}X_{21}X_{22}$GDVEE of SEQ ID NO: 24 (corresponding to residues 1 to 18 of SEQ ID NO: 24). Further, $N_{64}$ can be T or U and $N_{65}$ can be T or U.

When the PQR linker is a DNA molecule, it can be represented by the nucleic acid sequence of SEQ ID NO: 26:

(SEQ ID NO: 26)
$N_1N_2N_3$ $N_4N_5N_6$ $N_7N_8N_9$ $N_{10}N_{11}N_{12}$ $N_{13}N_{14}N_{15}$ $N_{16}N_{17}$

-continued $N_{18}$ $N_{19}N_{20}N_{21}$ $N_{22}N_{23}N_{24}$ $N_{25}N_{26}N_{27}N_{28}N_{29}N_{30}$ $N_{31}$ $N_{32}N_{33}$ $N_{34}N_{35}N_{36}$ $N_{37}N_{38}N_{39}$ $N_{40}N_{41}N_{42}$ $N_{43}N_{44}N_{45}$ $N_{46}$ $N_{47}N_{48}$ $N_{49}N_{50}N_{51}$ $N_{52}N_{53}N_{54}N_{55}N_{56}N_{57}$ $N_{58}N_{59}$ $N_{60}$ $N_{61}N_{62}N_{63}$ AAY CCT GGA CCT In the nucleic acid sequence of SEQ ID NO: 26, $N_1$ to $N_{63}$ represent any nucleic acid capable of forming codons encoding the subsequence GSG$X_1X_2X_3X_4X_5X_6X_7X_8X_9LX_{10}X_{11}X_{12}$GDVE$X_{13}$ of SEQ ID NO: 23 (corresponding to residues 1 to 21 of SEQ ID NO: 23) or the subsequence GSG$X_{14}X_{15}X_{16}X_{17}X_{18}X_{19}LX_{20}X_{21}X_{22}$GDVEE of SEQ ID NO: 24 (corresponding to residues 1 to 18 of SEQ ID NO: 24).

Exemplary nucleic acid sequences capable of encoding the cleavable peptides include those presented at SEQ ID NO: 4 (wild-type sequence from the porcine teschovirus) as well as at SEQ ID NO: 6 (wild-type sequence from the thosea asigna insect virus).

It is important that the codons of the nucleic acid sequence of the PQR linker encoding the subsequence NPGP of SEQ ID NO: 23 (corresponding to residues 22 to 25 of SEQ ID NO: 23) or 24 (corresponding to residues 19 to 22 of SEQ ID NO: 24) be identical to the codons used in the wild-type 2A and 2A-like peptides. As such, the codons of the PQR linker encoding the subsequence NPGP of SEQ ID NO: 23 (corresponding to residues 22 to 25 of SEQ ID NO: 23) or 24 (corresponding to residues 19 to 22 of SEQ ID NO: 24) correspond to:

AAY CC$N_{64}$ GGA CC$N_{65}$ (residues 64 to 75 of SEQ ID NO: 25, in which $N_{64}$ and $N_{65}$ can independently be T or U), when the PQR linker is a DNA or a RNA molecule; or AAY CCT GGA CCT (residues 55 to 66 of SEQ ID NO: 26), when the PQR linker is a DNA molecule.

In an embodiment, the PQR linker is a ribonucleic acid (RNA) molecule. In another embodiment, the PQR linker is a deoxyribonucleic acid (DNA) molecule. In yet another embodiment, the PQR linker can be a nucleic acid molecule including both ribonucleic acid nucleotides and deoxyribonucleic nucleotides (i.e., a DNA/RNA mixture).

The codons encoding the subsequence $X_1X_2X_3X_4X_5X_6X_7X_8X_9LX_{10}X_{11}X_{12}$GDVE$X_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) can be modified to increase the cleavage of the peptide and/or the stoichiometric ratio between the reporter protein and the protein of interest. For example, one or more codons encoding $X_1X_2X_3X_4X_5X_6X_7X_8X_9LX_{10}X_{11}X_{12}$GDVE$X_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) can be selected to correspond to the least preferred codon used in a particular host.

It is known in the art that various codons can encode the same amino acid and that different organism use some codons preferentially. It has been surprisingly found herein that when the codons encoding the subsequence $X_1X_2X_3X_4X_5X_6X_7X_8X_9LX_{10}X_{11}X_{12}$GDVE$X_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) were selected to include the most preferred codons used in a particular host, the cleavage of the PQR linker in the particular host was substantially decreased, which prevented quantifying the protein of interest. On the other hand, when the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) were selected to include some least preferred codons used in a particular host (e.g., de-optimized), the cleavage of the PQR linker was increased in the particular host, which, in some embodiments, allowed protein quantification.

Consequently, in an embodiment, at least some of the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) are not those which are preferably used in the host in which the protein quantification is intended to be performed. In still another embodiment, at least one of the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) is selected to be the least preferred codon used in the host in which the protein quantification is intended to be performed. In yet another embodiment, at least 2, 3, 4, 5, 6, 7, 8, 9, 10, 11, 12, 13, 14, 15, 16, 17, 18, 19 or 20 of the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or at least 2, 3, 4, 5, 6, 7, 8, 9, 10, 11, 12, 13, 14, 15, 16 or 17 of the codons encoding the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) are selected to be the least preferred codon used in the host in which the protein quantification is intended to be performed.

In still a further embodiment, at least 50%, at least 60%, at least 70%, at least 80%, at least 90% or at least 95% of the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) are selected to be the least preferred codon used in the host in which the protein quantification is intended to be performed. In yet another embodiment, all the codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24) are selected to be the least preferred codon used in the host in which the protein quantification is intended to be performed. In embodiments in which some but not all codons encoding the subsequence $X_1X_2X_3X_4X_5X_6X_7X_8X_9LX_{10}X_{11}X_{12}$GDVEX$_{13}$ of SEQ ID NO: 23 (corresponding to residues 4 to 21 of SEQ ID NO: 23) or the subsequence $X_{14}X_{15}X_{16}X_{17}X_{18}X_{19}LX_{20}X_{21}X_{22}$GDVEE of SEQ ID NO: 24 (corresponding to residues 4 to 18 of SEQ ID NO: 24), the least preferred codons used can be located preferentially at the 5' terminus of the nucleic acid molecule.

In embodiments in which the PQR linker encodes additional amino acids than those presented in SEQ ID NO: 23 or SEQ ID NO: 24, the PQR linker can include, for those additional amino acid, one or more least-favored codons being used.

To select codons least preferred in a particular host, it is possible to refer to Tables 3A and 3B below. Such tables include the most (Table 3A) and the least preferred (Table 3B) codons in function of the host. In order to include codons least preferred from a particular host, it is possible to select the codon associate to the particular host in Table 3B and/or to exclude the most preferred codon associated to the particular host in Table 3A.

Exemplary nucleic acid sequences containing codons which are least preferred in mammalian or *Drosophila* hosts include, but are not limited to the nucleic acid molecule having the nucleic acid sequence shown in SEQ ID NO: 9, 10, 11, 12, 14, 15 or 16.

TABLE 3A

Most preferred codons used for amino acids in function of origin of the host.

| Amino Acid | Human | Mouse | Yeast Rat (*S. cerevisea*) | Insect (*D. melanogaster*) | Bacteria (*E. coli*) |
|---|---|---|---|---|---|
| Alanine (A) | GCC | GCC | GCC GCT | GCC | GCC |
| Arginine (R) | CGG | CGG | AGG AGA | CGC | CGC |
| Asparagine (N) | AAC | AAC | AAC AAT | AAC | AAC |
| Aspartic acid (D) | GAC | GAC | GAC GAT | GAT | GAT |
| Cysteine (C) | TGC | TGC | TGC TGT | TGC | TGC |
| Glutamine (Q) | CAG | CAG | CAG CAA | CAG | CAG |
| Glutamic acid (E) | GAG | GAG | GAG GAA | GAG | GAA |

TABLE 3A-continued

Most preferred codons used for amino acids in function of origin of the host.

| Amino Acid | Human | Mouse | Yeast Rat (S. cerevisea) | Insect (D. melanogaster) | Bacteria (E. coli) |
|---|---|---|---|---|---|
| Glycine (G) | GGC | GGC | GGC GGT | GGC | GGC |
| Histidine (H) | CAC | CAC | CAC CAT | CAC | CAT |
| Isoleucine (I) | ATC | ATC | ATC ATT | ATC | ATT |
| Leucine (L) | CTG | CTG | CTG TTG | CTG | CTG |
| Lysine (K) | AAG | AAG | AAG AAA | AAG | AAA |
| Methionine (M) | ATG | ATG | ATG ATG | ATG | ATG |
| Phenylalanine (F) | TTC | TTC | TTC TTT | TTC | TTT |
| Proline (P) | CCC | CCC | CCC CCA | CCC | CCG |
| Serine (S) | AGC | AGC | AGC TCT | AGC | AGC |
| Threonine (T) | ACC | ACC | ACC ACT | ACC | ACC |
| Tryptophan (W) | TGG | TGG | TGG TGG | TGG | TGG |
| Tyrosine (Y) | TAC | TAC | TAC TAT | TAC | TAT |
| Valine (V) | GTG | GTG | GTG GTT | GTG | GTG |

TABLE 3B

Least preferred codon used for amino acids in function of origin of the host. (—) indicates that, besides the codon listed in Table 3A, no other codon exists for this amino acid.

| Amino Acid | Human | Mouse | Yeast Rat (S. cerevisea) | Insect (D. melanogaster) | Bacteria (E. coli) |
|---|---|---|---|---|---|
| Alanine (A) | GCG | GCG | GCG GCG | GCA | GCT |
| Arginine (R) | CGT | CGT | CGT CGG | CGG | CGA |
| Asparagine (N) | AAT | AAT | AAT AAC | AAT | AAT |
| Aspartic acid (D) | GAT | GAT | GAT GAC | GAC | GAC |
| Cysteine (C) | TGT | TGT | TGT TGC | TGT | TGT |
| Glutamine (Q) | CAA | CAA | CAA CAG | CAA | CAA |
| Glutamic acid (E) | GAA | GAA | GAA GAG | GAA | GAG |
| Glycine (G) | GGT | GGT | GGT GGG | GGG | GGA |
| Histidine (H) | CAT | CAT | CAT CAC | CAT | CAC |
| Isoleucine (I) | ATA | ATA | ATA ATC | ATA | ATA |
| Leucine (L) | CTA | CTA | CTA CTC | CTA | CTA |
| Lysine (K) | AAA | AAA | AAA AAG | AAA | AAG |
| Methionine (M) | — | — | — — | — | — |
| Phenylalanine (F) | TTT | TTT | TTT TTC | TTT | TTC |
| Proline (P) | CCG | CCG | CCG CCG | CCT | CCC |
| Serine (S) | TCG | TCG | TCG TCG | TCT | TCG |

TABLE 3B-continued

Least preferred codon used for amino acids in function of origin of the host. (—) indicates that, besides the codon listed in Table 3A, no other codon exists for this amino acid.

| Amino Acid | Human | Mouse | Yeast Rat (S. cerevisea) | Insect (D. melanogaster) | Bacteria (E. coli) |
|---|---|---|---|---|---|
| Threonine (T) | ACG | ACG | ACG ACG | CCT | ACA |
| Tryptophan (W) | — | — | — — | — | — |
| Tyrosine (Y) | TAT | TAT | TAT TAC | TAT | TAC |
| Valine (V) | GTA | GTA | GTA GTG | GTA | GTA |

Vector Comprising the PQR Linker and Associated Tools

The PQR linker can be presented in the form of a vector which is at least designed to also encode a reporter protein and a protein of interest. In the methods described herein, the PQR linker is intended to be located between the two proteins, i.e., between a nucleic acid sequence encoding a protein of interest and a nucleic acid sequence encoding the reporter protein. In the context of the present disclosure, the nucleic acid molecule of the PQR linker is referred to as the "first" nucleic acid molecule, the nucleic acid molecule encoding the reporter protein is referred as the "second" nucleic acid molecule and the nucleic acid molecule encoding the protein of interest is referred to as the "third" nucleic acid molecule.

In its simplest embodiment, the vector comprises the first nucleic acid molecule (i.e., the PQR linker) and is designed to allow for the subsequent integration of the second nucleic acid molecule (i.e., encoding the reporter protein) and of the third nucleic acid molecule (i.e., encoding the protein of interest) on each side of the first nucleic acid molecule. The vector must be designed to allow for the transcription of a mRNA encoding the entire poly-protein sequence, comprising the PQR linker flanked on each side by the reporter protein and the protein of interest. This embodiment of the vector allows a maximum of flexibility for the end-user to select a particular reporter protein and a particular protein of interest. In an embodiment, the second nucleic acid molecule (i.e., encoding the reporter protein) is intended to be located upstream of the first nucleic acid molecule and the third nucleic acid molecule (i.e., encoding the protein of interest) is intended to be located downstream of the first nucleic acid molecule. Alternatively, the second nucleic acid molecule (i.e., encoding the reporter protein) can be intended to be located downstream of the first nucleic acid molecule while the third nucleic acid molecule (i.e., encoding the protein of interest) can be intended to be located upstream of the first nucleic acid molecule.

In another embodiment, the vector can comprise both the PQR linker and the second nucleic acid sequence (i.e., encoding the reporter protein). In this embodiment, the end-user is provided with a customizable vector in which the third nucleic acid molecule (i.e., encoding the protein of interest) can be inserted and used. In this embodiment, the second nucleic acid molecule (i.e., encoding the reporter protein) can be located upstream of the first nucleic acid molecule and the third nucleic acid molecule (i.e., encoding the protein of interest) is intended to be located downstream of the first nucleic acid molecule. Alternatively, the second nucleic acid molecule (i.e., encoding the reporter protein) can be located downstream of the first nucleic acid molecule and the third nucleic acid molecule (i.e., encoding the protein of interest) is intended to be located upstream of the first nucleic acid molecule.

In another embodiment, the vector can comprise both the PQR linker and the third nucleic acid sequence (i.e., encoding the protein of interest). In this embodiment, the end-user is provided with a customizable vector in which the second nucleic acid molecule (i.e., encoding the reporter protein) can be inserted and used. In this embodiment, the second nucleic acid molecule (i.e., encoding the reporter protein) is intended to be located upstream of the first nucleic acid molecule and the third nucleic acid molecule (i.e., encoding the protein of interest) can be intended to be located downstream of the first nucleic acid molecule. Alternatively, the second nucleic acid molecule (i.e., encoding the reporter protein) is intended to be located downstream of the first nucleic acid molecule and the third nucleic acid molecule (i.e., encoding the protein of interest) can be intended to be located upstream of the first nucleic acid molecule.

In yet another embodiment, the vector can comprise the PQR linker, the second nucleic acid sequence (i.e., encoding the reporter protein) and the third nucleic acid molecule (i.e., encoding the protein of interest). In this embodiment, the end-user is provided with a ready-to-use vector to quantify a specific protein of interest using a specific reporter protein. In this embodiment, the second nucleic acid molecule (i.e., encoding the reporter protein) can be located upstream of the first nucleic acid molecule and the third nucleic acid molecule (i.e., encoding the protein of interest) can be located downstream of the first nucleic acid molecule. Alternatively, the second nucleic acid molecule (i.e., encoding the reporter protein) can be located downstream of the first nucleic acid molecule and the third nucleic acid molecule (i.e., encoding the protein of interest) can be located upstream of the first nucleic acid molecule.

The vectors described herein are designed to allow for the expression of one or more fusion protein (comprising the reporter protein and the protein of interest as well as the PQR linker). When a plurality of proteins of interest or reporter proteins are transcribed from the vector, each protein can be the same or different and comprises a reporter protein, a protein of the interest and a PQR linker between the reporter protein and the protein of interest.

In a further embodiment, the vector can be a linear vector or a circular vector. The vector can also be an integratable vector and as such can comprise a nucleic acid sequence capable of favoring or allowing integration of the vector in the genome of the host cell. In such embodiment, once integrated, some of the sequence of the original vector may have been removed during integration. In another embodiment, the vector can replicate independently from the host genome and as such can comprise a suitable origin of replication. The vector can also include a further nucleic acid molecule encoding a selection marker protein to identify host cells bearing the vector from those not bearing the vector.

In yet another embodiment, the vector can further comprise, upstream of the sequence encoding the poly-protein a regulatory sequence (promoter, enhancer and the like) for allowing the transcription of the mRNA of the poly-protein. If it is intended to study the expression of the protein of interest in its wild-type environment, it is possible to use the regulatory region associated with the protein of interest upstream of the poly-protein. It is also possible to introduce such vector in a host cell which has been previously knocked-down or knocked out for expression of the protein of interest. In other embodiments, it is possible to use other regulatory regions (e.g., constitutive or inducible regulatory regions) upstream of the poly-protein.

In still another embodiment, the vector can be designed to be integrated in the host's genome either in an unspecific or a specific manner (e.g., using the CRISPR/Cas9 system).

In the vectors described herein, the second nucleic acid molecule encodes a reporter protein. In the context of the present disclosure, a reporter protein is a protein which generates a quantifiable signal (either endogenously or via its enzymatic or biologic activity). The reporter protein can be, for example a fluorescent protein (such as, for example, a green fluorescent protein (GFP), a red fluorescent protein (RFP), a yellow fluorescent protein (YFP), a blue fluorescent protein (BFP) or a cyan fluorescent protein (CFP)), an antibiotic-resistance protein, an immunoglobulin or a immunoglobulin fragment, an ion channel, a transcription factor, a ribosomal protein, an enzyme and/or a receptor.

The vector can be any vector suitable for expressing the mRNA encoding the poly-protein. For example, the vector can be derived from a virus (e.g., retrovirus, adenovirus, herpes or vaccinia), from a yeast (e.g., an artificial chromosome or cosmid), from a bacteria (e.g., a bacterial plasmid for example), or from a wholly synthetic sequence.

The present disclosure can also provide a control vector which encodes for a control poly-protein which comprises a reporter protein, a protein of interest and a control PQR linker between the reporter protein and the protein of interest. The control PQR linker is not cleaved during the translation of the mRNA encoding the control fusion protein. The control vector can be used as a negative control to determine the signal associated with the reporter protein in an uncleaved form (i.e., while remaining in the fusion protein). As such, the vector and the control vector can be used together and should preferably comprise the same reporter protein, the same protein of interest, but a different PQR (one that can be cleaved in the vector, and one that cannot be cleaved in the control vector).

The present disclosure also provides for a kit for performing protein quantification using the vector described herein. In its simplest embodiment, the kit comprises the vector described herein and instructions on how to use the vector to quantify the protein of interest. For example, the instructions can indicate how to introduce the second nucleic acid molecule in the vector, how to introduce the third nucleic acid molecule in the vector, how to introduce the vector in a host cell, how to integrate the vector into the genome, how to select for host cell bearing the vector and/or how to measure the signal from the cleaved reporter protein. The kit can also provide a control vector and instructions on how to use the control vector to quantify the protein of interest. The kit can further provide a host cell and instructions on how to use the control vector to quantify the protein of interest.

The present disclosure also provides for a host cell or host organism comprising the nucleic acid molecule encoding the protein of interest, PQR linker and reporter (either in the form of a vector (independent or integrated in the genome) or in the form of an integrated nucleic acid molecule. The host cell, or host cell in a multi-cellular host organism, is capable of transcribing the nucleic acid molecule encoding the protein of interest and including the PQR linker and reporter. The host cell can be any eukaryotic cell. Exemplary eukaryotic cells include mammalian cells (such as human cells, rodent cells), other animal cells (such as fish cells, amphibian cells, insect cells, worm cells), plant cells, algal cells, fungal cells (such as yeast cells and mold cells).

Method for Quantifying Proteins in Host Cells

The present disclosure also provides method for quantifying a protein of interest in a host cell. The protein can be measured in vitro (when the host cell can be maintained in in vitro conditions), in vivo (when the host cell is located in a multicellular organism) or ex vivo (when the host cell is removed from a multicellular organism). In some embodiments, the protein can even be measured in living cells. In some specific embodiments, the protein can be measure at the single-cell level.

In the context of the present disclosure, the nucleic acid transcript associated with the poly-protein is a single nucleic acid molecule which is capable of being cleaved inside the PQR linker (between the codon encoding the penultimate glycine residue and the codon encoding the ultimate proline residue of the PQR linker). As such, the translation of the nucleic acid transcript of the poly-protein can generate two distinct proteins: the reporter protein and the protein of interest. Depending on which side the two proteins are located, these proteins will also contain one or more residues of the PQR linker. The protein located upstream of the PQR linker in the nucleic acid transcript will bear, at its carboxy (COOH) terminus all the residues of the PQR linker, except the ultimate proline residue. The protein located downstream of the PQR linker in the nucleic acid transcript will bear, at its amino ($NH^2$) terminus, the ultimate proline residue of the PQR linker.

The first step of this method requires that the vector encoding the poly-protein (which includes the PQR linker) be expressed in a host cell. Expression of the poly-protein can be driven from regulatory sequences present in the vector, upstream or downstream, of the poly-protein. Alternatively, expression of the poly-protein can be driven from endogenous regulatory sequences present in the host's genome by integrating the poly-protein specifically in the host's genome. The method can be practiced on any eukaryotic host cell which can transcribe the poly-protein in a poly-cistronic nucleic acid transcript and translate the resulting nucleic acid transcript. Without limitation the host cell can be a mammalian (such as a human), a plant, an insect, a yeast, a mold, and/or an algae.

The method can be designed to accommodate the quantification of more than one protein of interest. In order to do so, more than one PQR and reporter protein are encoded on the same vector or more than one vector is transferred inside the host cell. Preferably, each poly-protein comprises a distinct protein of interest and a distinct reporter protein. Care should also be taken when combining two or more reporter proteins in the same cell so as to avoid or minimize an overlap in the signal associated with each of the reporter proteins.

This first step may optionally include constructing the vector to include a reporter protein and/or a protein of interest, transferring the vector inside the host cell, integrating the vector inside the genome of the host cell and/or manipulating (for example, knocking down) the endogenous expression of the protein in the host cell. As indicated above, the nucleic acid sequence of the PQR linker is de-optimized (i.e., modified to include the least favored codons) in function of the host cell on which the quantification method will be practiced.

Once the nucleic acid transcript associated with the polyprotein is expressed, it can be cleaved during the translation process to generate, at a stoichiometric ratio (and in some embodiment, in an equimolar ratio), a cleaved reporter protein and a cleaved protein of interest. The next step of the method is thus to measure the signal associated with the cleaved reporter protein to estimate or quantify the amount of the protein of interest. The measure of the signal can be repeated in time or conducted only once.

The second step is dependent on the type of reporter protein being used. For example, if the reporter protein is a fluorescent protein, then this second step will include a determination of fluorescence. In such an example, it may be necessary determine the fluorescence which is specific to the cleaved reporter protein and/or to determine the background fluorescence which is not associated with the cleaved reporter protein. In another example, when the reporter protein is an enzyme, the second step can include contacting the enzyme with a substrate which will, upon the enzyme's activity, provide or remove a signal which can be measured and, optionally be quantified. In such an example, it may be necessary to provide a control value in the absence of the substrate. In still another example, if the reporter protein is an antibody, then this second step could include a determination of the antibody amount (either by flow cytometry, an ELISA and the like). In yet another example, if the reporter protein is an ion channel, then this second step could include measuring the activity associated by the channel.

Once the signal associated with the reporter protein has been obtained, it is used to estimate the amount of the protein of interest. For example, the signal can be graphically compared to a standard curve associating the fluorescence to the amount of the protein of interest. In another example, the PQR fluorescence signal of a protein of interest can be compared to the fluorescence signal (i.e., in another channel) of another protein of interest, for normalization or for analysis of differential protein production. In another example, and as described herein, the estimation of the protein based on the signal of the reporter protein with can be done through a linear regression technique. A linear regression that goes through the origin (0,0) could be performed between a standard (offline) measure of the protein of interest and the signal of the reporter protein. The slope of this regression (and the y intercept) enables the conversion of the fluorescent signal to the estimated value for the parameter. In another example, the PQR fluorescence signal of a protein of interest can be measured and compared against a measured phenotype, in a single cell. This can be used to determine the relationship between protein concentration and cellular phenotype. In a further example, the PQR fluorescence signal can be measured over time in the same cell to quantify the change in protein production over time, such as before and after an experimental manipulation, drug induction, or intervention.

As it will be shown below, a method to quantitate protein concentrations in single living cells using a fluorescent reporter was developed (FIG. 1). Modified virus sequences that allow for an equimolar separation of an upstream protein of interest and a downstream protein of interest were used, all contained within a single strand of RNA. When a fluorescent reporter is separated from the protein of interest, the number of fluorescent molecules produced are stoichiometric with the number of molecules of the protein of interest produced, and thus the fluorescence output can be used as a readout for the number of molecules of interest produced, i.e., its relative protein concentration (FIG. 1).

Figure 1A:
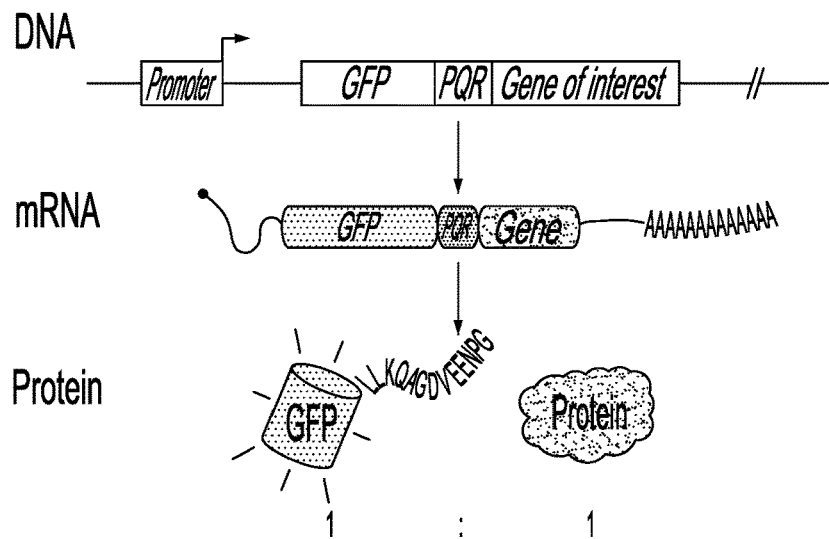
FIG. 1A illustrates that Protein Quantitation Ratioing (PQR) can determine relative protein concentration in single living cells. Stoichiometric protein translation can quantitate protein amounts. Insertion of a Protein Quantitation Reporter (PQR) between a fluorescent reporter (GFP) and a gene of interest creates a polycistronic mRNA for co-transcription and co-translation of GFP and the gene of interest. The PQR construct allows for one molecule of GFP (having an additional) C-terminal tail consisting of residues 6 to 18 of SEQ ID NO: 1 for example) to be synthesized for every one proportional to the concentration of GFP, then the fluorescence output of GFP is directly proportional to the concentration of GFP, then the fluorescence intensity of a cell can be used to quantitate the concentration of the protein of interest.
Figure 1B:
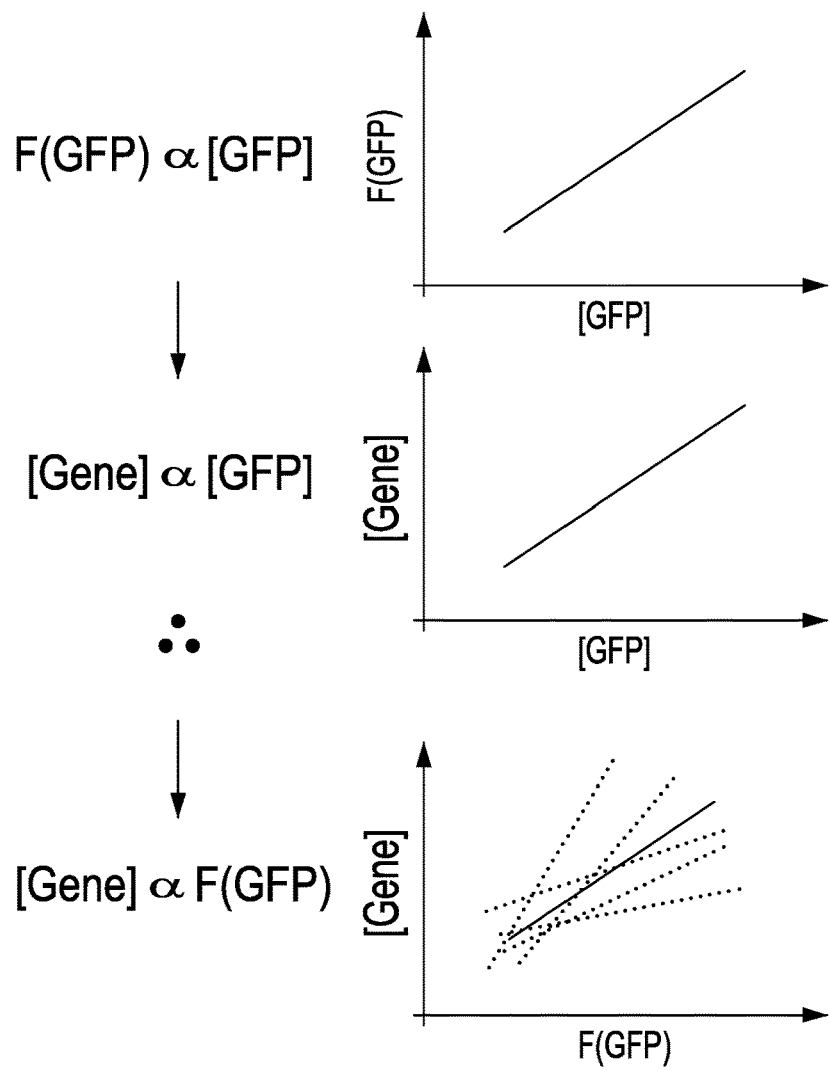
FIG. 1B illustrates the linear relationships between fluorescence output, fluorescent protein concentration, and protein of interest concentration allowing for Protein Quantitation Ratioing. Because the fluorescence output of GFP is directly proportional to its concentration (top panel and FIG. 1C), then using a PQR will produce a stoichiometric ratio between GFP and the protein of interest (middle panel), therefore enabling the fluorescence intensity of GFP to be used as a measure of the protein of interest concentration (bottom panel). Any (linear) differences in post-translational processing, maturation, or insertion rates of the protein of interest or GFP will change the slope of the relationship (dotted gray lines). For example, if at steady-state there are 11 functional molecules of a Shaker K+ channel for every 41 functional molecules of GFP, the relationship will still be linear. Importantly, protein concentrations is predominantly controlled by translation, with very small contribution from protein stability and degradation.
Figure 1C:
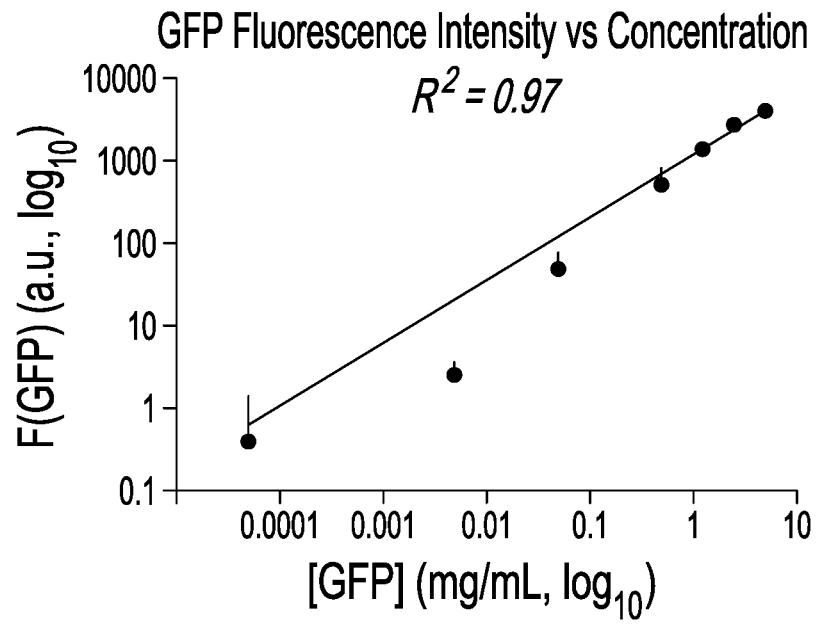
FIG. 1C shows that fluorescence intensity of GFP increases linearly as a function of its concentration over five orders of magnitude. Purified GFP was imaged using standard fluorescence microscopy. Pixel intensities are plotted in arbitrary units (a.u.) in $\log_{10}$. Coefficient of determination, $R^2$ values from a simple linear regression model were calculated from the averages of five experiments. Error bars standard deviations.
Figure 1D:
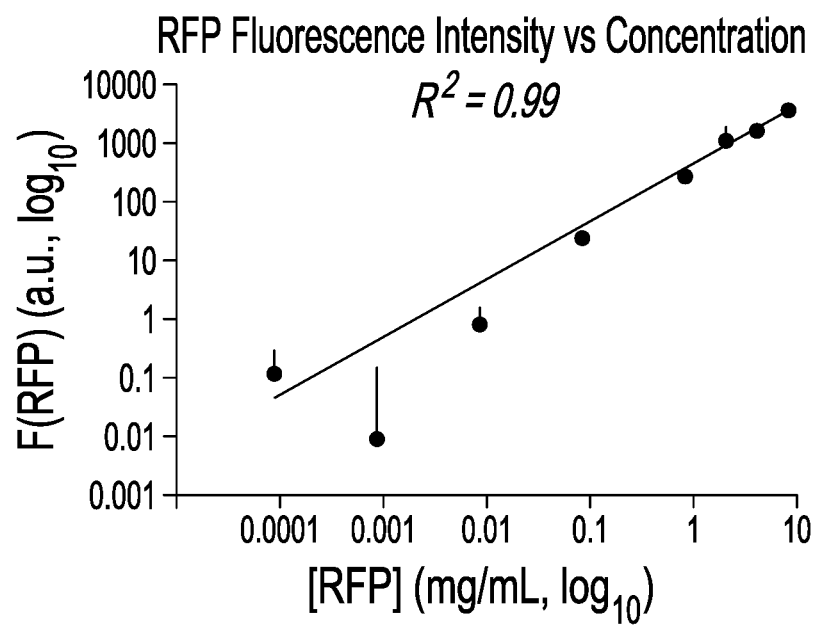
FIG. 1D shows that the fluorescence intensity of RFP increases linearly as a function of its concentration over five orders of magnitude. Purified RFP was imaged using standard fluorescence microscopy. Pixel intensities are plotted in arbitrary units (a.u.) in $\log_{10}$. Coefficient of determination, $R^2$ values from a simple linear regression model were calculated from the averages of five experiments. Error bars are standard deviations.

RNA sequences encoding peptides called cis-acting hydrolase elements (CHYSELs) can interact with the ribosome during protein translation to produce non-canonical protein coding events and separate a nascent polypeptide chain from an actively translating sequence. CHYSEL polypeptides (also known as "2A" and "2A-like" peptides, collectively) are used by RNA viruses to separate each of the viral genes to be translated. This allows for multiple proteins to be produced from the virus's single, polycistronic RNA strand. The mechanism by which separation of an upstream and downstream gene occurs is due to the specific and conserved sequence of CHYSEL residues upstream of a glycine proline separation point (FIG. 1A). In normal translation the peptidyl transferase activity of the ribosome produces the peptide bond of the growing peptide chain. The ribosome translocates and moves on to the next tRNA as the peptide chain is elongating through the exit tunnel. In the presence of the conserved CHYSEL residues that lie at the base of the exit tunnel, this forms a turn in the peptide chain that shifts the ester link between the peptide and the tRNA glycine away from the prolyl tRNA. This torsion causes the ribosome to stall and inhibits the peptidyl transferase activity, forcing the peptide chain to be released. The ribosome skips the glycyl-prolyl peptide bond, reinitiates from the proline, and translation continues with the downstream protein. This unique mechanism has been shown to produce equimolar amounts of upstream and downstream proteins, but previous high-throughput methods to quantitate bicistronic protein production have used CHYSEL peptides that do not consistently separate, and these poly-protein products contaminate the quantitation of protein concentration because they are by definition equimolar. Although CHYSEL sequences have been used for more than a decade, CHYSEL sequences were created in a novel concept to exploit the linear relationships between fluorescent molecule concentration and its fluorescence output, and fluorescent molecule concentration and the protein of interest concentration (FIG. 1B).

To create a protein quantitation reporter, CHYSEL sequences must meet two important criteria: first, separation of the protein of interest and the reporter must be close to 100% reliable, otherwise, the resulting poly-product may interfere with protein function, and second, production of the fluorescent reporter must be stoichiometric with the protein of interest, since many CHYSELs produce inconsistent stoichiometric separations depending on cell state, cell type, or at random. The production need not be equimolar at steady state levels, but consistently stoichiometric across cell states and types (FIG. 1B).

The present invention will be more readily understood by referring to the following examples which are given to illustrate the invention rather than to limit its scope.

Example I

Experimental Procedures

Figures 2A, 2B:
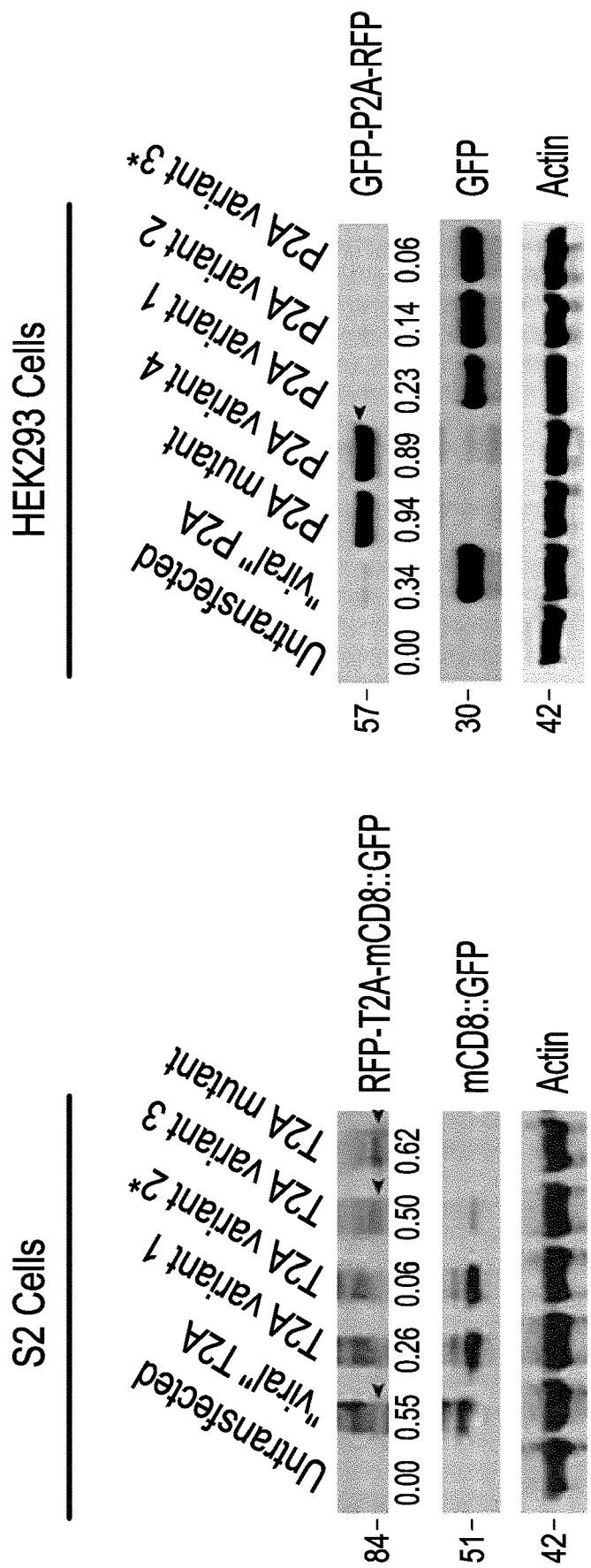
FIG. 2A illustrates that wild-type viral cis-acting hydrolase element (CHYSEL) sequences produce un-separated fusion proteins; PQR sequences produce reliable separation of separation efficiency using immunoblots (representative examples shown) and stoichiometric production of proteins using quantitative imagining. Anti-GFP antibody was used to detect GFP (middle blots) versus fusion product of unseparated RFP and GFP (top blots). Anti-Actin (bottom blots) was used to normalize pixel intensities of fusion product (numbers underneath top blots). We added gylcine and serine N-terminus linkers to all synthesized CHYSEL sequences, for example on the 2A-like sequence from Thosea asigna virus (T2A). Wildtype T2A viral codon usage or codon optimization produces fusion protein production, whereas codon de-optimization enhances separation efficiency. Separation efficiency for each CHYSEL construct was tested using immunoblotting of RFP-CHYSEL-mCD8::GFP constructs transfected into Drosophila S2 cells for T2A-derived sequences. Manipulation of the T2A peptide sequence by adding glycine and serine linkers still produced a large fraction of fusion protein (arrowhead in Lane 2, "viral" T2A). When we turned to manipulating codon sequence usage, we found that codon optimization produced equivalent or worse amounts of fusion products (arrowhead in Lane 5, T2A variant 3, 100% codon optimized) compared to the viral CHYSEL sequence, along with diminished amounts of separated mCD8::GFP. Codon de-optimization of specific amino acids reduced the proportion of fusion product (Lane 3, T2A variant 1 is 60% codon de-optimized and Land 4, T2A variant is 45% codon de-optimized). T2A variant 2, 45% codon de-optimization (asterisk), produced close to the background levels of the untransfected S2 cells lane. T2A mutant constructs (Lane 6) that produced fusion products were use as positive controls. All codon percentage change numbers do not include the glycine serine linker codons, which were required in all constructs (including "viral" sequences) to avoid large amounts of fusion products within the proteasome. Thus, using viral CHYSEL sequences will not work as Protein Quantitation Reporters, as these sequences leave a large fraction of uncleaved fusion protein product (arrowheads) that will contaminate any results of quantitation, and any experiments where fusion products are undesirable.
FIG. 2B illustrates that wild-type viral cis-acting hydrolase element (CHYSEL) sequences produces un-separated fusion proteins: PQR sequences produce reliable separation of proteins. We modified and synthesized different viral CHYSEL sequences to screen for separation efficiency using immunoblots (representative examples shown) and stoichiometric production of proteins using quantitative imaging. Anti-GFP antibody was used to detect GFP (middle blots versus fusion product of unseparated RFP and GFP (top blots). Anti-Actin (bottom blots) was used to normalize pixel intensities of fusion product (numbers underneath top blots). We added glycine and serine N-terminus linkers to all synthesized CHYSEL sequences, for example on the 2A sequences from Porcine teschovirus-1 (P2A). Codon de-optimization of specific CHYSEL residues produces reliable separation of proteins. We used HEK293 cells to test codon de-optimization of different CHYSEL residues using RFP—CHYSEL—GFP constructs derived from P2A sequences. We found that ~50% codon de-optimization of sequences (Lane 6, P2A variant 3), without altering the final four codons, allows for greatest separation efficiency. P2A variant 4, with the last 4 codons de-optimized (Lane 4) produced similar amounts of fusion product as the positive control (Lane 3), with negligible amounts of unseparated GFP (middle blot). P2A variants 1, 2, and 3, changing 100%, 80%, and 50%, respectively, of the codons (except for the last 4 codons) produced decreasing amounts of fusion product and increasing amounts of separated GFP. All codon percentage change numbers do not include the glycine serine linker codons, which were required in all constructs (including "viral" sequences) to avoid large amounts of fusion products within the proteasome. Thus, using viral CHYSEL sequences will not work as Protein Quantitation Reporters, as these sequences leave a large fraction of uncleaved fusion protein product (arrowheads) that will contaminate any results of quantitation, and any experiments where fusion products are undesirable.

Protein Quantitation Reporter Constructs. Sequences for CHYSEL peptides were tested from Group IV, positive-sense ssRNA viruses, including the Picornaviridae family for 2A peptides, or the Permutotetraviridae family for 2A-like peptides (Diao and White, 2012; Kim et al., 2011). For our initial screens, we mostly focused on four broad CHYSEL peptide sequences from the following viruses: Equine rhinitis A virus (E2A), Foot-and-mouth disease virus (F2A), Porcine teschovirus-1 (P2A), and Thosea asigna virus (T2A) and tested for stoichiometric production and separation of fluorescent proteins and Shaker potassium channel. We added glycine and serine linkers to the N-terminus of all CHYSEL sequences tested to enhance peptide separation (Yang et al., 2008). We selected the amino acid sequence ATNFSLLKQAGDVEENPGP (SEQ ID NO: 1) from the porcine teschovirus-1 for use in mammalian cells (Kim et al., 2011), and EGRGSLLTCGDVEENPGP (SEQ ID NO: 2) from the Thosea asigna insect virus for use in Drosophila cells (Diao and White, 2012). We compared codon optimization of the CHYSEL peptides versus the viral sequences of the CHYSEL peptides, and found that both the original viral sequence and the codon optimized forms resulted in a large fraction of un-separated, fusion product (FIGS. 2 and 11). Codon optimization often created a larger proportion of un-separated product, indicating that codon optimization could be worse for protein quantitation. Thus, we surmised that codon optimization could speed up ribosomal activity causing it to ignore the separation event between the final glycine and proline of the CHYSEL peptide. We tested DNA sequences that were selected for non-favored codons to decrease translation speed, which we found to enhance reliable separation (FIGS. 2 and 11) (Novoa and Ribas de Pouplana, 2012; Zhou et al., 2011). The DNA sequence chosen for the PQR in mammalian cells (P2A-derived with glycine and serine linker, codon variation 3) was: GGAAGCGGAGCGACGAATTTTAGTCTACT-GAAACAAGCGGGAGACGTGGAGGAAAACC CTG-GACCT (SEQ ID NO: 83). The DNA sequence chosen for the PQR in Drosophila cells (T2A-derived with glycine and serine linker, codon variation 2) was: GGAAGCGGA-GAAGGTCGTGGTAGTCTACTAACGTGTGGT-GACGTCGAGGAAAATCCTG GACCT (SEQ ID NO: 84). We also tested whether extended CHYSEL sequences, 30 amino acids in total length from the separation point, might enhance separation by further interacting with the exit tunnel (Luke et al., 2008). We found that these extended viral CHYSEL sequences still created a proportion of fusion product compared with shorter, 19 amino acid codon de-optimized CHYSEL sequences (FIG. 11c). Mutated PQR sequences that failed to separate were used as linkers for fusion protein experiments. All viral sequences were generated using gene synthesis into a pUC57 vector (BioBasic, Markham, ON), and cloned into pCAG for mammalian experiments or pJFRC7 for Drosophila melanogaster experiments. GFP, RFP, and BFP constructs were based on superfolderGFP, TagRFP-T, and mTagBFP2, respectively. SuperfolderGFP and TagRFP-T were chosen for their relatively fast maturation times, 6 min and 100 min, and average turnover rates at 26 hours, respectively (Corish and Tyler-Smith, 1999; Khmelinskii et al., 2012; Pedelacq et al., 2006; Shaner et al., 2008). For GFP and RFP protein concentration and fluorescence intensity measurements, proteins were purified from E. coli using GFP-specific chromatography columns (Biorad, Hercules, Calif.), and protein concentrations were measured using a Bradford assay with a Nano-Drop 2000 (Thermo Fisher). Samples were serially diluted and thin samples were imaged on glass slides to reduce any non-linear effects using a standard fluorescence microscope (see Image Acquisition). ShakerGFP cDNA and hs-PER:: YFP were kind gifts, and all other plasmids were obtained through Addgene (Cambridge, Mass.). GFP::RFP fusion proteins were verified using immunoblotting (FIG. 2), and imaging experiments verified that these large proteins were excluded from the nucleus.

Cell Culture. HEK293, Neuroblastoma-2A (N2A), and 22c10 cells were cultured at 37° C. under 5% $CO_2$ in Dulbecco's Modified Eagle Medium (Wisent, St-Bruno, QC) and H-Cell (22c10) (Wisent, St-Bruno, QC), or for Drosophila S2 and Kc cells, at 25° C. in Ex-Cell 420 Medium (Sigma-Aldrich, St. Louis, Mo.). Media for mammalian cells were supplemented with 10% fetal bovine serum (FBS) (Wisent), and 100 units/mL penicillin (Life Technologies, Carlsbad, Calif.) and 100 µg/mL streptomycin (Life Technologies). Cells were transfected with 5 pg of plasmid DNA in 35 mm dishes using Lipofectamine 3000 (Life Technologies). For genome editing experiments, 800 ng of CRISPR-Cas9 plasmid DNA were co-transfected with 800 ng of repair template circular plasmid in 12-well plates. After 2-7 days, cells were non-enzymatically dissociated and seeded on glass coverslips and prepared for imaging and electrophysiology experiments.

Immunoblotting. Immunoblot experiments were performed four times. One billion cells were placed into lysis buffer (25 mM HEPES, 150 mM NaCl, 1 mM EDTA, 1% Triton-X) with SIGMAFAST™ protease inhibitor tablet solution (Sigma-Aldrich). Protein concentrations were measured using a bicinchoninic acid protein assay (Pierce, Rockford, Ill.) and 30-40 µg of protein was loaded into a NuPAGE Novex 12% Bis-Tris Gel (Life Technologies). Proteins were separated by electrophoresis and transferred to a polyvinylidene fluoride membrane using Invitrogen iBlot dry transfer (Life Technologies). The membrane was blocked in 5% BSA in PBS-T and incubated with the following antibody dilutions: 1:1000 anti-RFP rabbit polyclonal (R10367, Life Technologies), 1:2000 anti-GFP rabbit polyclonal (A6455, Life Technologies), and 1:5000 anti-actin JLA-20 mouse monoclonal (Developmental Studies Hybridoma Bank, Iowa City, Iowa) for the top, middle, and bottom blots, respectively, in FIGS. 2 and 11. Secondary antibodies used were 1:10 000 HRP-conjugated Donkey anti-rabbit IgG (Jackson ImmunoResearch Laboratories, Inc.) and HRP-conjugated goat anti-mouse IgG (Abcam, USA). All antibodies were dissolved in 5% BSA in PBS-T. Membranes were imaged using the Pierce ECL Chemiluminescence Detection Kit for HRP (Thermo Scientific, USA). The ratio of band intensity of GFP or fusion products was normalized to actin and quantified using ImageJ, as described (Cvetkovska et al., 2013). We performed Western blots on all PQR constructs used in experiments and confirmed the absence of fusion protein products for GFP, RFP, ShakerGFP, PER, Cut, and RPL13A proteins (FIGS. 11 and 12).

Image Acquisition. Fluorescence and bright-field microscopy was performed using a Zeiss AxioScope A1, an Olympus laser scanning confocal microscope FV1000, and a Perkin Elmer UltraView spinning disk confocal Leica DMLFSA microscope. All images were acquired at 512×512 pixels using a 40× water objective, N.A. 1.0 (epifluorescence) or 60× oil, N.A. 1.4, or 63× water, N.A. 0.9, objectives (confocal) corresponding to an 215×160 µm or 120× 110 µm field of view, respectively. Fluorescence emission was detected using a charge-coupled device camera (MRm) for the Zeiss and (OrcaER, Hamamatsu) Leica microscopes, and photomultiplier tubes for the Olympus microscope. All image acquisition parameters were fixed for each imaging channel for exposure time, excitation intensity, gain, and voltages. Cells that were dimmer or brighter than the fixed initial acquisition dynamic range were not included for analysis. We verified that shifting the acquisition window across fluorescence intensity ranges produced linear correlations throughout the range. In co-transfection of GFP and RFP experiments, cells that were non-fluorescent in either the green or red channel were not imaged, therefore the $R^2$ values for our co-transfection experiments are likely to be overestimates of the true $R^2$.

Image Analysis. Images were selected for analysis based on identification of single cells and low background. Images were adjusted for contrast and brightness only. Image analysis was performed blind to genotype. Fluorescence pixel intensities were measured in several regions of interest (ROIs) within the cell using a custom written program in MatLab (MathWorks, Natick, Mass.) or ImageJ. Average pixel intensities were calculated from three ROIs of 10×10 pixels for measurements within the cytoplasm and nucleus, or from five ROIs of 3×3 pixels for membrane and mitochondrial measurements. For *Drosophila* small lateral ventral neuron analysis, six ROIs of 6×6 pixels were measured from six neurons per lobe, and six animals per time point were chosen. All signal intensities were background subtracted from the average of three 10×10 ROIs surrounding the cell. We verified that RFP was still cyclically co-translated at later time points by analyzing red fluorescence intensities on Day 5 and 6 using a lower acquisition setting (FIG. 10c).

Electrophysiology. Standard whole cell voltage clamp was used to record potassium currents from HEK293 cells. During recordings, cells were maintained for 1-2 hours at 25° C. in extracellular solution consisting of 140 mM NaCl, 10 mM $CaCl_2$, 5 mM KCl, 10 mM HEPES, and 10 mM glucose at pH 7.4, 319 mOsm. Patch electrodes were pulled from standard wall borosilicate glass (BF150-86-10, Sutter instruments, Novato, Calif.) with 3-5 MΩ resistances. The intracellular pipette solution was 150 mM KCl, 2 mM $MgCl_2$, 1 mM $CaCl_2$, 2 mM EGTA, 20 mM HEPES, and 20 mM sucrose at pH 7.23, 326 mOsm. Whole cell potassium currents were low pass filtered at 5 kHz and measured using an Axopatch 200B amplifier (Axon instruments, Sunnyvale, Calif.), and recorded using a DigiData 1200 with pClamp9 software (Molecular Devices). All pipette and cell capacitances were fully compensated. Cells were held at −80 mV and then given +10 mV steps of 35 ms. The steady-state current elicited at +30 mV was used for analysis. Consistent cell capacitance, and membrane and access resistances were verified before and after recordings.

Statistical Analysis. Linear correlations were calculated by fitting the data to a simple linear regression model, with the coefficient of determination, $R^2$. We tested the null hypothesis that the variables were independent of each other and that the true $R^2$ value was 0. To test the confidence of our $R^2$ values for each experiment, we calculated the F statistic and its P value of the F-test on the regression model. We also used the permutation test to obtain a P value on the likelihood of obtaining our $R^2$ value by randomly shuffling the data and calculating a new $R^2$ value, repeated for one million runs (FIG. 7). Both approaches gave similar P values for all experiments.

To compare the $R^2$ values generated from PQRs to other conditions, we used the data from the fusion protein experiments as positive controls. We used the bootstrap method to generate a 95% confidence interval for the true $R^2$ value of the positive controls. We randomly chose 80% of the positive control data points to calculate a new $R^2$ value and repeated this for ten million runs, and used these simulated $R^2$ values to obtain upper and lower estimates of the positive control $R^2$ values (FIG. 7). All statistical analyses were performed using custom-written programs in MatLab (Mathworks).

*Drosophila melanogaster* Circadian Experiments. To generate the UAS-RFP-PQR-PER::YFP construct, PER::YFP was amplified from hs-PER::YFP, ligated with the RFP-PQR fragment, and inserted into the pUAST vector. Transgenic fly lines were created using P-element transgenesis (Bestgene Inc, Chino Hills, Calif.). The UAS-RFP-PQR-PER::YFP flies were crossed to the per-Gal4 driver line, P{GAL4-per.BS}3. Crosses were maintained at 25° C. in a 12 hour light-dark cycle incubator and newly eclosed F1 progeny were entrained for three days before collection. Six female flies were selected for each time point (6 AM and 6 PM, or zeitgeber time ZT0 and ZT12, respectively). Flies were fixed in 3.7% paraformaldehyde in 0.2M carbonate-bicarbonate buffer, pH=9.5 at 4° C. for 12 hours. Fly brains were then dissected, mounted on slides, and imaged using confocal microscopy.

*Drosophila* Dendritic Complexity Experiments. The pJFRC-20XUAS-IVS-RFPnls-PQR-cut construct was created by genomic extraction of the cut coding region from the fly UAS-cut (Grueber et al., 2003). The cDNA was ligated to RFPnls-PQR, and the resulting construct was cloned into the pJFRC7 vector. The transgenic fly w-; P{20XUAS-IVS-RFPnls-PQR-cut}attP was created by PhiC31 integrase-mediated transgenesis (Bestgene Inc). Homozygous flies w-; P{20XUAS-IVS-RFPnls-PQR-cut}attP, were crossed to homozygous w-; 221-Gal4, UAS-mCD8::GFP to selectively express RFPnls-PQR-cut in class I da neurons. Crosses were maintained at 18° C. and wandering third instar larvae were used for imaging. Larvae were dissected in phosphate-buffered saline and the anterior end, gut, tracheal tubes, and fat bodies were removed prior to imaging. Class I ddaE living neurons were imaged using a Fluoview FV1000 confocal laser scanning microscope (Olympus). Neuronal morphology was visualized using the membrane-bound mCD8::GFP and Cut protein levels were determined by ROI analysis of nuclear red fluorescence intensity. Complete dendritic arbors were reconstructed and the number of terminal branches and total dendritic length were computed using the NeuronJ plugin in Fiji.

Genome Editing using CRISPR-Cas9. Guide RNAs were designed as 20 bp DNA oligonucleotides and cloned into pX330 (Addgene 42230), and co-transfected with a circular PQR repair template using Lipofectamine 3000 (Life Technologies). All CRISPR-Cas9 guide RNAs were tested for activity using SURVEYOR Nuclease and SURVEYOR Enhancer S (Transgenomics) on extracted genomic DNA. Re-annealed products were analyzed on 4%-20% Novex TBE polyacrylamide gels (Life Technologies). Repair templates were constructed by placing PQR-XFP between homology arms specific to human, mouse, or fly RPL13A. The homology arms lacked the RPL13A promoter, which prevented expression of the PQR-XFP until in-frame genomic integration within an active coding gene. Left and right homology arms were 1.0 kb for the human genome, 1.5 kb for the mouse genome, and 700 bp for the *Drosophila* genome. Cellular fluorescence from PQRs was observed four days post-transfection.

Validation of PQR Genomic Insertion. Genotyping experiments were performed in experimental duplicate. Integration of PQR into the endogenous RPL13A or IgK genomic locus was validated by genomic DNA extraction six days post-transfection and genotyping using primers outside and within the homology arms of the repair template.

The 5' and 3' ends were probed with two sets of primers and the endogenous RPL13a or IgK locus was PCR amplified. Restriction digests were then performed on PCR products at sites specific for PQR. All genomes were sequenced to identify the PQR and genomic junctions.

To verify that insertion of our PQR constructs into the endogenous RPL13A locus did not produce fusion protein products, we performed Western blots on manually enriched populations of the knock-in cell lines (FIG. 12). No fusion products were detected, and the enriched populations of knock-in cell lines were indistinguishable from wild-type cells with respect to phenotype and growth rate, and have been passaged multiple times. Finally, we also used quantitative PCR to verify that that the genome-edited cells produced RNA transcripts at similar levels to wildtype (FIG. 12).

Quantitative Real-Time PCR. For relative quantification of RPL13A and IgK mRNA levels from manually enriched stable cell lines, total RNA was extracted and purified using the PureLink RNA mini kit (Life Technologies) and genomic DNA was eliminated using DNaseI (New England Biolabs). Total RNA was reverse-transcribed with gene-specific primer cocktails (2 µM final concentration of each primer) using Superscript III reverse-polymerase (Life Technologies). This cDNA template was used for real-time PCR using the TaqMan Fast Advanced Mastermix (Life Technologies). Real-time PCR amplification was detected using the StepOnePlus Real-Time PCR System (Applied Biosystems) and cycle quantification values were calculated using the StepOne software. Experiments were performed in two to three experimental replicates with two technical replicates. Relative gene expression was determined using a ΔΔCq method. For relative quantification experiments, cycle quantification values were normalized to GAPDH in HEK293, N2A and 22c10 cells.

For absolute quantification of RPL13A and IgK mRNA levels from single cells, individual cells were imaged in drops of culture media on Teflon-coated glass slides before extraction and purification of total RNA using the TRIzol reagent (Life Technologies). Absolute quantification of RPL13A and IgK copy numbers was determined using standard curves generated with synthesized oligo standards containing the RPL13A and IgK target (sequences shown in Tables 4). Primers and double-quenched 5'-FAM/ZEN/IowaBlackFQ-3' probes were purchased from Integrated DNA Technologies (Coralville, Iowa). All DNA and primer sequences used are shown in Table 4.

TABLE 4A

Nucleotide sequence and amino acid sequence of the CHYSEL peptide used in the Examples

| CHYSEL peptides | CHYSEL DNA sequences | CHYSEL Oligo Peptide Sequences |
|---|---|---|
| vT2A_18aa | GAGGGCAGAGGAAGTCTGCTAACATGCGGTGACGTCGAGGAGAA TCCTGGACCT (SEQ ID NO: 7) | EGRGSLLTCGDVEENPGP (SEQ ID NO: 2) |
| T2A_variant 1_Optimized | GAGGGACGCGGATCCCTGCTGACCTGCGGCGATGTGGAGGAGA ACCCCGGACCG (SEQ ID NO: 85) | EGRGSLLTCGDVEENPGP (SEQ ID NO: 2) |
| T2A_variant 2_deoptimed | GAAGGTCGTGGTAGTCTACTAACGTGTGGTGATGTAGAAGAAAAT CCTGGACCT (SEQ ID NO: 86) | EGRGSLLTCGDVEENPGP (SEQ ID NO: 2) |
| T2A_variant 3_deoptimed | GAAGGTCGTGGTAGTCTACTAACGTGTGGTGACGTCGAGGAAAA TCCTGGACCT (SEQ ID NO: 87) | EGRGSLLTCGDVEENPGP (SEQ ID NO: 2) |
| T2A_mutant | GAGGGCAGAGGAAGTCTGCTAACATGCGGTGACGTCGAGGAGAA TGCGGCGCCT (SEQ ID NO: 88) | EGRGSLLTCGDVEENAAP (SEQ ID NO: 95) |
| vP2A_30aa | GCTATGACTGTGATGGCATTTCAGGGGCCAGGT- GCCACTAACTTCTCCCTTTTAAAACAAGCAGGGGATGTTGAAGAA AATCCCGGGCCC (SEQ ID NO: 89) | AMTVMAFQGPGATNFSLLKQAG DVEENPGP (SEQ ID NO: 96) |
| vP2A_19aa | GCTACTAACTTCAGCCTGCTGAAGCAGGCTGGAGACGTGGAGGA GAACCCTGGACCT (SEQ ID NO: 4) | ATNFSLLKQAGDVEENPGP (SEQ ID NO: 1) |
| P2A_variant 1 | GCGACGAATTTTAGTCTACTAAAACAAGCGGGTGATGTAGAAGAA AATCCGGGTCCG (SEQ ID NO: 90) | ATNFSLLKQAGDVEENPGP (SEQ ID NO: 1) |
| P2A_variant 2 | GCGACGAATTTTAGTCTACTAAAACAAGCGGGTGATGTAGAAGAA AACCCTGGACCT (SEQ ID NO: 91) | ATNFSLLKQAGDVEENPGP (SEQ ID NO: 1) |
| P2A_variant 3 | GCGACGAATTTTAGTCTACTGAAACAAGCGGGAGACGTGGAGGA AAACCCTGGACCT (SEQ ID NO: 92) | ATNFSLLKQAGDVEENPGP (SEQ ID NO: 1) |
| P2A_variant 4 | GCTACTAACTTCAGCCTGCTGAAGCAGGCTGGAGACGTGGAGGA GAATCCGGGTCCG (SEQ ID NO: 93) | ATNFSLLKQAGDVEENPGP (SEQ ID NO: 1) |
| P2A_mutant | GCTACTAACTTCAGCCTGCTGAAGCAGGCTGGAGACGTGGAGGA GAACGCGGCGCCT (SEQ ID NO: 94) | ATNFSLLKQAGDVEENAAP (SEQ ID NO: 1) |

TABLE 4B

Nucleotide sequence of primers and probes used in the Examples

| Gene | Forward Primer | Reverse Primer | Reverse-Transcription Primer | Probe |
|---|---|---|---|---|
| Human RPL13A outside of homology arms | CTGGAGGTCAGTGATGAGCA (SEQ ID NO: 97) | TGGAATGGTGTGGCAAGTTA (SEQ ID NO: 98) | | |
| Mouse Rpl13a outside of homology arms | CGGGTTGCTAACCTGGAATA (SEQ ID NO: 99) | CAGTCTCCATCAAGGGGAAA (SEQ ID NO: 100) | | |
| Drosophila RpL13A outside of homology arms | TGAACCTCTCGGGACACTTC (SEQ ID NO: 101) | TGTGGATATGGTTGCATTCTG (SEQ ID NO: 102) | | |
| Mouse IgK outside of homology arms | GGGGGAAAGGCTGCTCATAA ((SEQ ID NO: 103) | TAACTGGGGGAAGGGACACT ((SEQ ID NO: 104) | | |
| RFP | ATGGTGTCTAAGGGCGAAG (SEQ ID NO: 105) | TTACTTGTACAGCTCGTCCATG (SEQ ID NO: 106) | | |
| GFP | TTGATGGAGCCAAAGATGTG (SEQ ID NO: 107) | GTACGTGTTCCGTAAGACGG (SEQ ID NO: 108) | | |
| Human RPL13A | TGTTTGACGGCATCCCAC (SEQ ID NO: 109) | CTGTCACTGCCTGGTACTTC (SEQ ID NO: 110) | CTGCTGGCCACATTTTATGTC (SEQ ID NO: 111) | CTTCAGACGCACGACCTTGAGGG (SEQ ID NO: 112) |
| Mouse Rpl13a | TCCCTCCACCCTATGACAAG (SEQ ID NO: 113) | GTCACTGCCTGGTACTCC (SEQ ID NO: 114) | GCAGCCCTGCTACTCATTTTC (SEQ ID NO: 115) | ACGCCCCAGGTAAGCAAACTTTCT (SEQ ID NO: 116) |
| IgK | AGTGGAAGATTGATGGCAGTG (SEQ ID NO: 117) | CTGTCTTTGCTGTCCTGATCA (SEQ ID NO: 118) | GGTGGATTTCAGGGCAACTA (SEQ ID NO: 119) | ACAAAATGGCGTCCTGAACAGTTGG (SEQ ID NO: 120) |
| Human GAPDH | GATCATCAGCAATGCCTCCT (SEQ ID NO: 121) | GTCATGAGTCCTTCCACGATAC (SEQ ID NO: 122) | GTACATGACAAGGTGCGGCT (SEQ ID NO: 123) | TGGCCAAGGTCATCCATGACAACT (SEQ ID NO: 124) |
| Human RPL13A (Single Cell experiments) | CAAATACACAGAGGTCCTCAAGA (SEQ ID NO: 125) | CTTCGCCCTTAGACACCATAG (SEQ ID NO: 126) | CTGCTGGCCACATTTTATGTC (SEQ ID NO: 127) | TGGTCGGAAGCGGAGCTACTAACT (SEQ ID NO: 128) |
| Mouse Rpl13a (Single Cell experiments) | TGCAAGTTCACAGAGGTCC (SEQ ID NO: 129) | CTTCGCCCTTAGACACCATAG (SEQ ID NO: 130) | GCAGCCCTGCTACTCATTTTC (SEQ ID NO: 131) | AGACTAAAATTCGTCGCTCCGCTTCC (SEQ ID NO: 132) |
| IgK Constant Region | TCACAAGACATCAACTTCACCC (SEQ ID NO: 133) | TCCACGTCTCCAGCCTGCT (SEQ ID NO: 134) | GGTGGATTTCAGGGCAACTA (SEQ ID NO: 135) | AGCTCCGCTTCCACACTCATTCC (SEQ ID NO: 136) |
| Drosophila RpL13A knock-in animal | CGACGTCAGCTAGGAGTGTG (SEQ ID NO: 137) | TGAAATTGGTTTGTGCCTACC (SEQ ID NO: 138) | | |
| RFP knock-in animal | GGCCACCTGATCTGCAAC (SEQ ID NO: 139) | TTCTGCTGCCGTACATGAAG (SEQ ID NO: 140) | | |

TABLE 4C

Nucleotide sequence of the oligonucleotides used in the Examples

| Gene | Synthesized Oligo Sequence |
|---|---|
| Mouse Rpl13a | AGGCAGAAAAGAATGTGGAGAAGAAAATCTGCAAGTTCACAGAGGTCCTCAAGACCAACGGACTCCTGGTGGGAAGCGGAGCGACGAATTTTAGTCTACTAAAACAAGCGGGTGATGTAGAAGAAAACCCTGGACCT (SEQ ID NO: 141) |
| IgK | GACATAACAGCTATACCTGTGAGGCCACTCACAAGACATCAACTTCACCCATTGTCAAGAGCTTCAACAGGAATGAGTGTGGAAGCGGAGCTACTAACTTCAGCCTGCTGAAGCAGGCTGGAGACGTGGAGGAGAACCCTGGACCTGCTAGCATGGTGAGCAAGGGCGAGGAGGATAACATGGCCTCTCTC (SEQ ID NO: 142) |

TABLE 4C-continued

Nucleotide sequence of the oligonucleotides used in the Examples

Gene  Synthesized Oligo Sequence

Human  TACGGAAACAGGCCGAGAAGAACGTGGAGAAGAAAATTGACAAATACACAGAGGTCCTCAAGACCCACGGACTCCTGGTCGGA
RPL13A  AGCGGAGCTACTAACTTCAGCCTGCTGAAGCAGGCTGGAGACGTGGAGGAGAACCCTGGACCTATGGTGTCTAAGGGCGAAGA
  GCTGATTAAGGAGAACATGCACATGAAGCTGTACATGGAGGG (SEQ ID NO: 143)

Example II

Ratioing Using the Protein Quantification Reporter Linker (PQR linker)

The experimental procedures associated with this example were presented in Example I.

We modified and tested different CHYSEL sequences for efficient and stoichiometric separation of the upstream and downstream genes and identified different sequences for use in *Drosophila* cells and vertebrate cells. We first screened for CHYSEL sequences that produce reliable separation of the upstream and downstream protein (FIG. 2). We created different CHYSEL sequences for use in *Drosophila* and vertebrate cells, taken from different RNA viruses and modified, and then codon de-optimized at specific residues (FIG. 2 and Example I). Thus, we collectively called these different DNA constructs for *Drosophila* and for vertebrate use, Protein Quantitation Reporters (PQRs).

Next, we tested the stoichiometric ratio and linear relationship between different genes separated by our PQRs at the single cell level. First, we quantified fluorescence intensities in Human Embryonic Kidney 293 (HEK293) cells expressing a fusion protein of one molecule of green fluorescent protein (GFP) attached to one molecule of Red Fluorescent Protein (RFP) by a mutated PQR linker (FIG. 3). Because fluorescence intensity is directly proportional to the concentration of fluorescent molecules over several orders of magnitude, particularly at physiological concentrations (mg per mL) (Furtado and Henry, 2002) (FIG. 1c), we measured the fluorescence output (i.e., brightness) of a cell to quantitate the ratio of GFP to RFP molecules. We found that green and red fluorescence intensities in cells expressing GFP::RFP were linearly correlated with a coefficient of determination, $R^2=0.74$ (n=74 cells, P<0.001) (FIG. 3a). Co-transfection of GFP and RFP into cells produced green and red fluorescence intensities that had a weak covariance, with $R^2=0.37$ (n=59 cells, P<0.001) due to differences in uptake, gene expression, and protein expression of GFP- versus RFP-encoding plasmids (FIG. 3b). Co-transfection of plasmids is a common technique used for qualitative determination of protein co-expression, where the amount of DNA for each plasmid is titrated to a desired expression level, and it is then incorrectly assumed that the brightness of the cell corresponds to the expression level of the co-transfected plasmid(s) (FIG. 3b). When we expressed GFP and RFP separated by a PQR sequence in cells, we found that the green and red fluorescence intensities were correlated with an $R^2=0.78$ and 0.66 for GFP-PQR-RFP (n=77 cells, P<0.001) and RFP-PQR-GFP (n=77 cells, P<0.001), respectively (FIGS. 3c, d). These $R^2$ values for PQR constructs were within the 95% confidence interval for the $R^2$ value for the GFP::RFP fusion protein, whereas the co-transfection of GFP and RFP $R^2$ value was outside the 95% confidence interval (Example I and FIG. 7). These results demonstrate that a PQR can produce stoichiometric ratios of proteins indistinguishable from fusing a fluorescent reporter. These PQR results were also not due to the incomplete separation of the upstream and downstream genes, creating a subpopulation of GFP and RFP fusion product (FIG. 2). To further determine whether genes separated by a PQR produced spatially separated proteins, we expressed spectrally-distinct fluorophores with different subcellular localization signals, each separated by a PQR sequence in a single, polycistronic strand (YFPmito-PQR-CFPnls-PQR-RFP, FIGS. 8a-c). Fluorescence intensities of different colors in mitochondrial, nuclear, or cytoplasmic compartments were linearly correlated (ranging from $R^2=0.54$ to 0.69 for different organelles, n=40 cells, P<0.001), and intensities for the non-expected fluorophores were not detectable above background, confirming that fusion proteins were not formed and localized to inappropriate cellular compartments. This also demonstrates that stoichiometric production of proteins is maintained for polycistronic mRNAs using PQRs, allowing for protein quantification in multiple regions of interest using different subcellular localization signals.

Figure 3F:
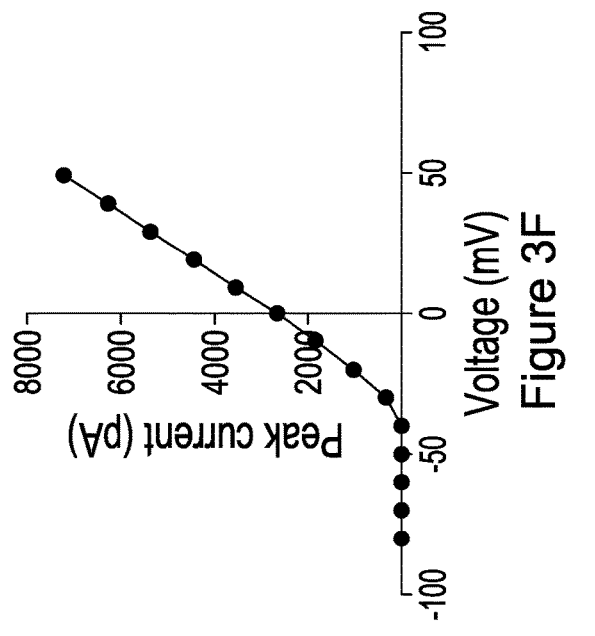
FIG. 3F shows an I-V curve generated using +10 voltage steps during a whole cell patch clamp recordings performed on HEK293 cells.
Figure 3H:
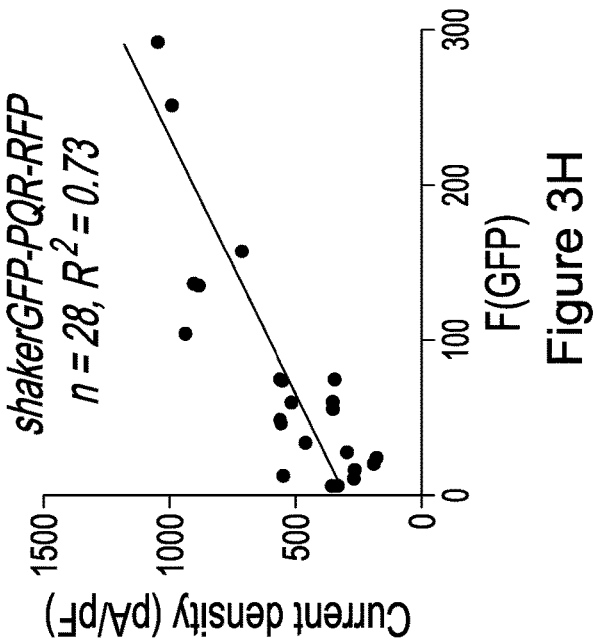
FIG. 3H shows that $K^+$ channel current density was linearly correlated with green fluorescence intensity in cells expressing the Shaker $K^+$ channel fused to GFP, with a coefficient of determination. $R^2+0.73$ (n=28 cells, $P<0.001$).
Figure 3E:
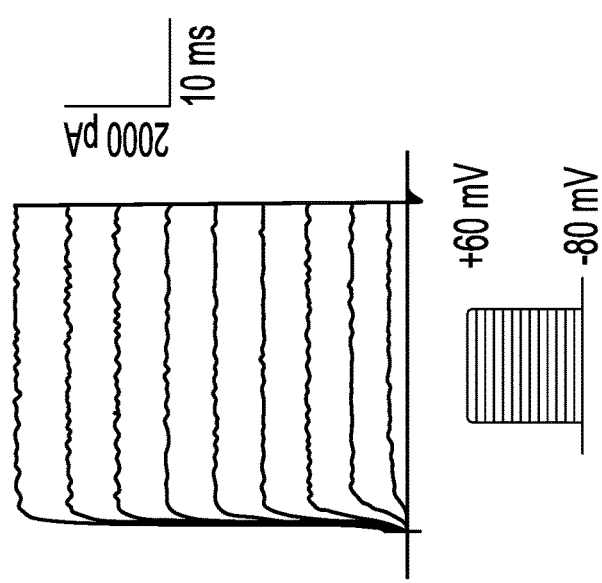
FIG. 3E shows whole cell patch clamp recordings performed on HEK293 cells.
Figure 3G:
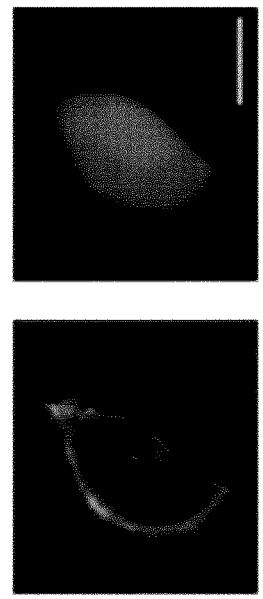
FIG. 3G shows sample micrographs of ShakerGFP-PQR-RFP-transfected HEK293 used to measure the GFP fluorescence intensity. The GFP signal (left panel) is localized to the plasma membrane whereas the RFP signal (right panel) is cytoplasmic. Scale bar is 25 μm.

PQR can relate cellular phenotype as a function of protein concentration. To determine whether PQR fluorescence intensity could correlate with a cellular phenotype directly related to protein concentration, we measured ion channel concentrations using whole cell patch clamp electrophysiology. We expressed the *Drosophila* Shaker potassium channel with a GFP molecule embedded within the inactivation domain (Batulan et al., 2010) separated by PQR-RFP (ShakerGFP-PQR-RFP) in HEK293 cells (FIG. 3e). Measurements of $K^+$ channel current density compared to green fluorescence intensity of the cell membrane produced a linear correlation of $R^2=0.73$ (n=28 cells, P<0.001) (FIG. 3f). Current density as a function of red fluorescence intensity had a correlation of $R^2=0.55$ (P<0.001), and green to red fluorescence correlation was $R^2=0.84$ (P<0.001) (FIGS. 3g-h), indicating that the steady-state ratio between RFP and a membrane protein four times larger and with several fold slower turnover maintained a linear relationship across expression ranges (coefficient of variation for current was 0.34) (Corish and Tyler-Smith, 1999; Zhao et al., 1995). We performed these electrophysiological and image analyses using different fluorescence microscopy methods and found strong linear correlations amongst all excitation methods (e.g., metal-halide lamp, mercury vapor lamp, lasers), fluorophores, and microscopy methods tested (ranging from $R^2=0.90$ to 0.94 between different methods) (FIG. 8d). This is expected because the linear relationship between concentration of a fluorophore and its brightness (FIG. 1c) will be maintained regardless of excitation source, fluorophore, or emission detection method. This demonstrates that all standard fluorescence microscopy methods can be used with this technique.

To demonstrate the applicability of this technique in single neurons in animals, we used the predictable and quantitative changes in protein amounts that occur in the circadian system (FIG. 4a). The transcription factor Period, or PER, controls the circadian rhythms of the *Drosophila* brain, and PER protein levels cycle every 24 hours as it is synthesized, shuttled into and out of the nucleus, and degraded in the proteasome. To measure cyclic changes in fluorescence intensity in single cells, we used a fusion protein of PER and Yellow Fluorescent Protein (PER::YFP) separated by PQR with RFP. We used period-Gal4 to drive expression of the UAS-PER::YFP-PQR-RFP construct within small lateral ventral neurons of the *Drosophila* brain (FIG. 4a). We found that yellow fluorescence intensities cycled with a 24 hour periodicity without increasing beyond a fixed point, as the PER::YFP fusion protein was continually formed and destroyed (FIG. 4b). RFP has a slightly longer half-life (26 hours) than PER, thus as RFP was co-translated and separated from the PER::YFP, we observed parallel production and degradation at early time points. However, the red fluorescence intensities eventually increased cyclically over several days until it saturated the fixed acquisition settings, set at the initially low red fluorescence intensities (FIG. 4b).

We next used PQR to determine a quantitative relationship between protein amount and cellular phenotype in single living cells. *Drosophila* dendritic arborization (da) neurons can be classified into four groups (class I, II, III, and IV) based on their dendritic arbor complexity, and the transcription factor Cut has been implicated in regulating this complexity in a dosage-dependent manner. However, it is not clear how Cut protein levels regulate neurite outgrowth. For example, the transcription factor may act as a binary switch, or have a linear relationship with dendritic growth. Because da neurons are relatively large cells (FIG. 4c) and we surmised that as a transcription factor, low levels of Cut would produce significant phenotypes, we used a PQR with a nuclear localization signal (RFPnls) to sequester the fluorophore and enhance the signal. We selectively expressed UAS-RFPnls-PQR-cut in class I da neurons using the 221-Gal4, UAS-mCD8::GFP line. We measured red fluorescence within the nucleus and used GFP to image the dendritic morphology to quantify the total dendritic arbor length and number of terminal branches (FIG. 4c). We found that dendritic arbor complexity (number of dendritic terminals or total dendritic length) increases logarithmically with Cut protein levels until the dendritic branching effect was saturated (FIG. 4d). These results indicate that Cut regulates dendritic arbor complexity in a concentration-dependent non-linear manner.

We next sought to insert PQRs into endogenous genomic loci to create a polycistronic mRNA that would preserve regulatory elements, such as the mRNA untranslated regions (UTR) (FIG. 5a). We used Clustered Regularly Interspaced Short Palindromic Repeats-Cas9 (CRISPR-Cas9) genome editing to generate custom RNAs that guide Cas9 nuclease to create a double-strand break at a specific genomic locus. DNA double-strand breaks within a cell can be repaired through homologous recombination, and in the presence of an exogenous repair template containing DNA sequences of interest flanked by homologous sequence arms, foreign sequences can be recombined into the genome. We generated repair templates to insert a PQR after the protein coding sequence of a gene, but before the final stop codon and 3' UTR, to produce a single RNA strand encoding the endogenous protein of interest and a fluorescent reporter (FIG. 5a). We inserted PQRs with RFP or blue fluorescent protein with a nuclear localization signal (BFPnls) within the endogenous RPL13A genomic locus in human, *Drosophila*, and mouse genomes using HEK293, Kc, and Neuroblastoma-2A cells, respectively (FIGS. 5b-d).

Using these genome-edited cells, we then wanted to examine the relationship between absolute mRNA transcript numbers and protein amount in the same cell. We combined PQR of endogenous protein production with single cell quantitative PCR (FIG. 6). We first imaged a live cell expressing a PQR and then lysed the cell to extract and measure its PQR mRNA transcripts (FIG. 6a). Using our HEK293 cell line carrying a PQR-RFP reporter at the endogenous RPL13A locus (FIG. 5b), we found that the number of mRNA molecules ranged from 50 to 570, and RPL13A relative protein amounts as measured by RFP fluorescence intensity, clustered between 200 to 800 arbitrary units, resulting in no correlation between RPL13A mRNA versus protein amounts ($R^2=0.03$; n=22) (FIG. 6b-d). As a comparison, we inserted a PQR-GFP reporter into the immunoglobulin kappa (κ) light chain genomic locus, IgK, in the mouse monoclonal antibody cell line, 22c10 (FIG. 6e). As expected, these 22c10 cells produced a large amount of IgK mRNA ranging from 1 500 to 180 500 molecules in a single cell, despite being derived from a single clonal cell (FIGS. 6f, g). The green fluorescence intensity distribution also varied widely, which produced a weak correlation between IgK transcript number and IGK protein amount ($R^2=0.22$, n=36) (FIG. 6h). To confirm that our fluorescence intensity distributions and correlations were not due to differences between the fluorophores, cell types, or procedure, we first swapped the PQR fluorophores from the Rpl13a and IgK genes to create Rpl13a-PQR-GFPnls and IgK-PQR-RFP. Next, we used CRISPR-Cas9 genome-editing on both of these genes within a single cell line to create double knock-in cells (FIG. 9). By measuring green fluorescence in the nucleus and red fluorescence in the cytoplasm within a single 22c10 cell, and then quantifying its Rpl13a and IgK mRNA amounts, we verified that the mRNA expression of these genes is a poor predictor of actual protein translation. These results using both mouse and human genes confirm previous studies demonstrating the poor correspondence between mRNA expression and actual protein production.

The technique we describe here, Protein Quantitation Ratioing, uses standard fluorescence imaging available through multiple microscopy methods. PQR is fast, has sensitivity at single cell resolution, and can be performed with time-lapse in living cells. Using a cell's brightness as a readout for the protein expression level of a gene, PQR can have a wide range of applications in cell biology to quantitatively measure relationships between phenotypes and protein levels.

The PQR technique quantifies steady-state protein levels within a cell, and differences in kinetics of the upstream and downstream proteins (e.g., folding, maturation, or turnover rates) will change the slope of the linear relationship, but the fluorescence will still be proportional to the number of molecules translated (FIG. 1b). For example, the *Drosophila* Shaker $K^+$ channel is homo-tetrameric (i.e., four molecules are required for a single functional channel), has a turnover rate of several days, but has complex and comparatively rapid internalization and insertion rates on timescales of minutes to hours. Our PQR results using the Shaker $K^+$ channel demonstrate that the technique can be used even for complicated membrane proteins with slow degradation rates. In addition, protein concentration is predominantly controlled by translation, with very small contribution (<5%) from protein stability and degradation. To model how differences in protein dynamics might affect PQR measurements, we simulated two cells expressing PQRs that exhibited different kinetics of a protein of interest (FIG. 10a). We found that differences in protein turnover did not adversely affect PQR accuracy, with >85% of cases producing at least 90% accurate quantification, across tens of thousands of proteins with randomly varying kinetics (FIG. 10). This is because PQR measurements are ratiometric between two cells rather than absolute measurements of protein abundance, and because the CHYSEL mechanism forces not only the identical ON rate of the protein of interest, but also the exact protein amount being produced. This creates a regularly resetting mechanism for the PQR fluorophore to match the protein of interest kinetics. Experimentally, we used the circadian system as an extreme example of very tightly regulated gene expression, with precisely controlled mRNA production and mRNA degradation, and protein production and degradation. Our PQR measurements could integrate the cyclic production of PER protein until the PQR fluorescence intensities saturated (FIG. 4b). However, cyclic changes in PER protein can still be accurately measured at any arbitrary later time point by resetting the acquisition setting for PQR fluorescence (FIG. 10c), demonstrating the robust sensitivity of the PQR technique. More precise spatial and temporal measurements of protein kinetics may be obtained through the use of photoswitchable molecules to allow for subcellular activation and quantitative imaging of newly synthesized fluorescent molecules. Although the PQR technique quantifies protein amounts indirectly, it is a similarly indirect measurement as quantitative immuno-blots and quantitative PCR. Currently, the only alternatives to PQR are quantitative immuno-blots and protein assays, which require isolation of large amounts of heterogeneous starting material.

For our positive controls, we fused a fluorescent protein to a protein of interest to track and quantitate protein amounts. However, unlike a physical tag, PQR uses a genetic tag separated during protein synthesis, leaving only ~20 amino acids on the carboxy terminus of the upstream protein and a single proline at the start of the downstream protein. A fusion protein must be expressed at high enough levels to detect, and be accessible for analysis (e.g., it may be membrane-associated or may be secreted), and any modification can interfere with protein stability, activity, or function (e.g., N-terminus and C-terminus additions can affect Type I and Type II transmembrane proteins, or alter intracellular signaling). Using the integral membrane protein Shaker K$^+$ channel, we verified that placement of the Shaker gene upstream or downstream of the PQR sequences did not affect its membrane insertion or properties (FIG. 8e). Separation of the PQR to different locations than the protein of interest allows for easier quantification of genes expressed at low levels (FIG. 4c), where the PQR can be sequestered within the nucleus or nucleolus or for large or complex cells such as neurons (FIG. 4c), or for quantification of transmembrane and secreted proteins, such as the production of antibodies. For example, the genomic organization of vertebrate antibodies joins upstream variable exons to a final 3' constant exon and insertion of a PQR between the coding sequence and the 3' UTR will allow for quantification of antibody production in all cells that synthesize the specific antibody type.

The RPL13A gene encodes for Ribosomal Protein L13A and is expressed in every cell in all eukaryotes at moderately high levels (FIG. 6b), and is commonly used as a housekeeping gene for normalization in quantitative DNA and protein measurements. Therefore, quantitation of endogenous RPL13A protein levels in single cells can be used as a measure of an individual cell's overall transcriptional and translational status (FIGS. 5, 6). Quantifying RPL13A fluorescence levels in a second channel (e.g., RFP or BFPnls) allows for normalization across cells or experiments, and for optical effects such as spherical aberration, optical distortions, and imaging depths during in vivo imaging. Thus, using this approach the relative levels of any protein of interest can be determined across conditions using the ratio of fluorescence between the protein of interest normalized to RPL13A fluorescence.

Quantification of endogenous proteins using PQR does not necessarily require the generation of knock-in organisms. For example, efficient genome editing of post-mitotic neurons transfected with the CRISPR-Cas9 system has been demonstrated using biolistic transfection and in utero electroporation. This will allow for PQR of endogenous proteins within specific cells in vivo, for example by transfection of CRISPR-Cas9 for homologous recombination of PQR constructs within neurons. The Protein Quantitation Ratioing technique has broad expansion possibilities, such as measuring protein production in single cells over time for drug screening, quantitation of endogenous protein levels in single cells in vivo, normalization across experiments and optical effects using the ratio of RPL13A levels, and allowing a wide range of quantitative experiments examining gene to phenotype relationships.

Example III

PQR Optimization

The experimental procedures used in this example are presented in Example I.

In order to determine how to optimize PQR, we first assessed whether the tri-peptide GSG was necessary for performing protein quantification, we compared the cleavage of a PQR linker bearing and lacking the GSG tri-peptide (refer to Table 5 for a description of the sequences used).

TABLE 5

Description of wild-type and GSG-modified P2A and T2A peptides as well as wild-type and codon-optimized DNA sequences encoding for such peptides.

| SEQ ID NO | Sequence | Description |
|---|---|---|
| 1 | ATNFSLLKQAGDVEENPGP | Native P2A peptide from Teschovirus-1 |
| 3 | GSGATNFSLLKQAGDVEENPGP | P2A peptide from teschovirus-1 to which a GSG peptide has been added at the N-terminus |

TABLE 5-continued

Description of wild-type and GSG-modified P2A and T2A peptides as well as wild-type and codon-optimized DNA sequences encoding for such peptides.

| SEQ ID NO | Sequence | Description |
|---|---|---|
| 4 | GCT ACT AAC TTC AGC CTG CTG AAG CAG GCT GGA GAC GTG GAG GAG AAC CCT GGA CCT | DNA sequence encoding the native P2A peptide (SEQ ID NO: 1) and corresponding to the viral RNA sequence (i.e., not-codon optimized) |
| 5 | GGA AGC GGA GCC ACA AAC TTC AGT CTC CTG AAA CAG GCA GGC GAT GTG GAG GAG AAT CCC GGC CCA | DNA sequence encoding the modified P2A peptide (SEQ ID NO: 3). The sequence corresponds to a 100% (excluding the GSG tri-peptide encoding sequence, identified in bold) or 86% (including the GSG tri-peptide encoding sequence) codon-optimized for the mouse model. |
| 2 | EGRGSLLTCGDVEENPGP | Native T2A peptide from Thosea asigna virus |
| 6 | GSGEGRGSLLTCGDVEENPGP | Modified T2A peptide to which a GSG peptide has been added at the N-terminus |
| 7 | GAG GGC AGA GGA AGT CTG CTA ACA TGC GGT GAC GTC GAG GAG AAT CCT GGA CCT | DNA sequence encoding the native T2A peptide (SEQ ID NO: 2) and corresponding to the viral RNA sequence (i.e., not-codon optimized) |
| 8 | GGA AGC GGA GAG GGG AGA GGG TCT CTG CTG ACC TGC GGG GAT GTC GAG GAG AAC CCC GGC CCC | DNA sequence encoding the modified T2A peptide (SEQ ID NO: 6) and corresponding to a 100% (excluding the GSG tri-peptide encoding sequence, identified in bold) or 86% (including the GSG tri-peptide encoding sequence) codon-optimized for the Drosophila melanogaster model. |

As shown on FIG. 14, the presence of the GSG tri-peptide is required for proper separation of the two poly-proteins and for proper protein function (FIG. 14A). Without the proper separation, the resulting fusion protein product that is produced is often non-functional and degraded by the cell (FIG. 14B).

Next, we wanted to determine if codon optimization of the corresponding DNA sequences encoding the PQR peptides could further increase cleavage of the two proteins. To do so, native viral DNA sequences and codon optimized DNA sequences (but both with GSG-modification, refer to table 5 for a complete description) were first compared for their ability to produce separate proteins and limit the presence of a fusion protein product. We found that both the original viral sequence and the codon optimized forms resulted in a fraction of un-separated, fusion product (FIG. 13). To our surprise however, we also found that codon optimization sometimes created a larger proportion of un-separated product, meaning the codon optimization could be worse for using a PQR for protein quantitation in single cells.

Without wishing to be bound by theory, it was hypothesized that codon optimization sometimes sped up the ribosomal activity during translation causing it to ignore the separation event between the glycine and proline bond of the CHYSEL peptide (Zhou et al. 2011; Novoa and Ribas de Pouplana 2012). Slowing down the ribosome using unfavored codons should therefore increase separation of the PQR sequence. Consequently, we tested the variations of the P2A and T2A sequences presented in Table 6 to determine their usefulness in protein ratioing.

TABLE 6

DNA sequences encoding the P2A (SEQ ID NO: 1) or T2A (SEQ ID NO: 3) peptides. Codons in bold have been de-optimized to for the mouse model (i.e., the codon least favored in the host has been selected). Codons underlined with a double line have been optimized for the Drosophila melanogaster model (i.e., the codon most favored in the host has been selected). Underlined codons have been mutated to code for alanine.

| SEQ ID NO | Sequence | Description |
|---|---|---|
| 4 | GCT ACT AAC TTC AGC CTG CTG AAG CAG GCT GGA GAC GTG GAG GAG AAC CCT GGA CCT | Wild-type viral DNA sequence encoding SEQ ID NO: 1 |

TABLE 6-continued

DNA sequences encoding the P2A (SEQ ID NO: 1) or T2A (SEQ ID NO: 3) peptides. Codons in bold have been de-optimized to for the mouse model (i.e., the codon least favored in the host has been selected). Codons underlined with a double line have been optimized for the *Drosophila melanogaster* model (i.e., the codon most favored in the host has been selected). Underlined codons have been mutated to code for alanine.

| SEQ ID NO: | Sequence | Description |
|---|---|---|
| 9 | GGA AGC GGA GCG ACG AAT TTT AGT CTA CTA AAA CAA GCG GGT GAT GTA GAA GAA AAT CCG GGT CCG | Variation 1 of SEQ ID NO: 4. This sequence corresponds to a 100% (excluding the GSG tri-peptide encoding sequence) or 86% (including the GSG tri-peptide encoding sequence) codon-deoptimized sequence. |
| 10 | GGA AGC GGA GCG ACG AAT TTT AGT CTA CTA AAA CAA GCG GGT GAT GTA GAA GAA AAC CCT GGA CCT | Variation 2 of SEQ ID NO: 4. This sequence corresponds to a 80% (excluding the GSG tri-peptide encoding sequence) or 68% (including the GSG tri-peptide encoding sequence) codon-deoptimized sequence. |
| 11 | GGA AGC GGA GCG ACG AAT TTT AGT CTA CTG AAA CAA GCG GGA GAC GTG GAG GAA AAC CCT GGA CCT | Variation 3 of SEQ ID NO: 4. This sequence corresponds to a 50% (excluding the GSG tri-peptide encoding sequence) or 45% (including the GSG tri-peptide encoding sequence) codon-deoptimized sequence. |
| 12 | GGA AGC GGA GCT ACT AAC TTC AGC CTG CTG AAG CAG GCT GGA GAC GTG GAG GAG AAT CCG GGT CCG | Variation 4 of SEQ ID NO: 4. This sequence corresponds to a 21% (excluding the GSG tri-peptide encoding sequence) or a 18% (including the GSG-tripeptide encoding sequence) codon-deoptimized sequence. |
| 13 | GGA AGC GGA GCT ACT AAC TTC AGC CTG CTG AAG CAG GCT GGA GAC GTG GAG GAG AAC <u>GCG GCG</u> CCT | Mutant of SEQ ID NO: 4 in which the underlined codons have been mutated to code for an alanine. This sequence serves as a control in which none of the fusion proteins are cleaved. |
| 6 | GAG GGC AGA GGA AGT CTG CTA ACA TGC GGT GAC GTC GAG GAG AAT CCT GGA CCT | Wild-type viral DNA sequence encoding SEQ ID NO: 3 |
| 14 | GGA AGC GGA GAA GGT CGT GGT AGT CTA CTA ACG TGT GGT GAT GTA GAA GAA AAT CCT GGA CCT | Variation 1 of SEQ ID NO: 6. This sequence corresponds to a 60% (excluding the GSG tri-peptide encoding sequence) or 52% (including the GSG-tripeptide encoding sequence) codon-deoptimized sequence. |
| 15 | GGA AGC GGA GAA GGT CGT GGT AGT CTA CTA ACG TGT GGT GAC GTC GAG GAA AAT CCT GGA CCT | Variation 2 of SEQ ID NO: 6. This sequence corresponds to a 45% (excluding the GSG tri-peptide encoding sequence) or 38% (including the GSG-tripeptide encoding sequence) codon-deoptimized sequence. |
| 16 | GGA AGC GGA GAG <u>GGA CGC</u> GGA <u>TCC</u> CTG <u>CTG ACC</u> TGC <u>GGC GAT GTG</u> GAG GAG <u>AAC CCC</u> GGA <u>CCG</u> | Variation 3 of SEQ ID NO: 6. This sequence corresponds to a 60% (excluding the GSG tri-peptide encoding sequence) or a 52% (including the GSG-tripeptide encoding sequence) codon-optimized sequence. The codons underlined with a double line have been optimized by the software bestgene |

The DNA sequences presented in Table 6 were introduced in HEK 293 cells using lipofectamine (life technologies Inc.) for the PQR sequences from P2A-based variants, and *Drosophila* S2 cells for the PQR sequences from T2A-based variants. We then tested each sequence for how much fusion product each variation would create, using immuno-blots (FIG. 7) to detect the fusion product. The actin and GFP bottom and middle row blots, respectively are controls to demonstrate that the separated product does form. The untransfected columns are used as negative controls. The P2A mutant and T2A mutant is used as a positive control to indicate where a fusion protein product will occur (what size the protein should run at on the immuno-blot). As shown on FIG. 7a, P2A variation 3 and T2A variation 2 produce the least amount of fusion product, close to background levels of the untransfected cell column. The quantitation of the results presented in FIG. 7a is shown in FIG. 7b.

As indicated in FIG. 15, stochoimetric cleavage have been achieved when using a sequence derived from the F2A peptide (SEQ ID NO: 17 to which as GSG peptide sequence has been added) as a PQR between the GFP and RFP reporter proteins. The PQR-encoding sequence was the following: GGT TCT GGT GCT CCT GTC AAA CAA ACT CTT AAC TTT GAT TTA CTC AAA CTG GCT GGG GAT GTA GAA AGC AAT CCA GGT CCA (SEQ ID NO: 82).

Example IV

In Vivo PQR

A knock-in animal with a protein quantitation reporter and fluorescent protein (PQR-XFP) integrated into the Ribosomal Protein L13A (RPL13A) locus can be an invaluable resource for biologists. It allows the quantification of RPL13A expression in any cell type and developmental stage of the animal. The PQR RPL13A fluorescence output represents the relative levels of RPL13A protein expression, and this can be used as a standard reference for normalization during in vivo imaging or to normalize a single cell's transcriptional and translational states. The knock-in PQR-XFP can be stably maintained in the RPL13A locus and passed on from generation to generation provided that the knock-in is genetically stabilized and heritable.

To create a knock-in Drosophila expressing PQR-RFPnols at the RpL13A genomic locus, we employed the strategy of first creating a transgenic fly expressing the guide RNA (gRNA) taregeting the RpL13A locus to be crossed to another fly expressing the Cas9 nuclease within the embryos (Port et al., 2014). The subsequent combination of the customized gRNA and Cas9 nuclease in the offspring, both expressed only in the embryo stage, forms the active CRISPR-Cas9 complex to perform genome editing at the the specific locus. The repair template containing the edited PQR-RFP locus is injected into these embryos, and are screened for positive results later in development and in their offspring to ensure germlie transmission.

To create the gRNA transgenic flies, a U6:3gRNA plasmid was first constructed and its genome targeting was verified in Drosophila Kc cells lines. High quality DNA plasmid was then prepared and sent to a transgenic service (The Bestgene, Inc) for embryo injections to create the transgenic flies. These gRNA flies were then crossed to nanos-cas9 flies, and embryos expressing the two components gRNA and Cas9 were collected for injection with the circular DNA repair template, RPL13A-PQR-RFPnols (Bestgene, Inc). After reaching adulthood, these G0 flies were crossed to one another and the resulting F1 larvae with red nucleoli in all cells were identified and isolated using a standard epifluorescence microscope (FIG. 16). The knock-in was verified by genotyping and Sanger sequencing (FIG. 16), as described above.

We have characterized the pattern of red fluorescent nuclei in living and dissected third instar larvae. Red nuclei were observed throughout the entire animal with varying degrees of fluorescent intensities between different tissues, implying different levels of cellular transcription and translation. For cells undergoing rapid proliferation during development, such as the body wall tissue and the gut, the fluorescence intensities are significantly stronger than those from post-mitotic cells, like neurons (FIG. 16). For cells of the same type, the variation in fluorescence intensity is considerably smaller than compared to cells coming from different tissues.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Batulan, Z., Haddad, G. A., and Blunck, R. (2010). An intersubunit interaction between S4-S5 linker and S6 is responsible for the slow off-gating component in Shaker K+ channels. The Journal of biological chemistry 285, 14005-14019.

Corish, P., and Tyler-Smith, C. (1999). Attenuation of green fluorescent protein half-life in mammalian cells. Protein engineering 12, 1035-1040.

Cvetkovska, V., Hibbert, A. D., Emran, F., and Chen, B. E. (2013). Overexpression of Down syndrome cell adhesion molecule impairs precise synaptic targeting. Nature neuroscience 16, 677-682.

Diao, F., and White, B. H. (2012). A novel approach for directing transgene expression in Drosophila: T2A-Gal4 in-frame fusion. Genetics 190, 1139-1144.

Furtado, A., and Henry, R. (2002). Measurement of green fluorescent protein concentration in single cells by image analysis. Analytical biochemistry 310, 84-92.

Gaj, T., Gersbach, C. A., and Barbas, C. F., 3rd (2013). ZFN, TALEN, and CRISPR/Cas-based methods for genome engineering. Trends in biotechnology 31, 397-405.

Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.

Grueber, W. B., Jan, L. Y., and Jan, Y. N. (2003). Different levels of the homeodomain protein cut regulate distinct dendrite branching patterns of Drosophila multidendritic neurons. Cell 112, 805-818.

Hardin, P. E., Hall, J. C., and Rosbash, M. (1990). Feedback of the Drosophila period gene product on circadian cycling of its messenger RNA levels. Nature 343, 536-540.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Kim, J. H., Lee, S. R., Li, L. H., Park, H. J., Park, J. H., Lee, K. Y., Kim, M. K., Shin, B. A., and Choi, S. Y. (2011). High cleavage efficiency of a 2A peptide derived from porcine teschovirus-1 in human cell lines, zebrafish and mice. PloS one 6, e18556.

Khmelinskii, A., Keller, P. J., Bartosik, A., Meurer, M., Barry, J. D., Mardin, B. R., Kaufmann, A., Trautmann, S., Wachsmuth, M., Pereira, G., et al. (2012). Tandem fluorescent protein timers for in vivo analysis of protein dynamics. Nature biotechnology 30, 708-714.

Lindstrom, M. S. (2009). Emerging functions of ribosomal proteins in gene-specific transcription and translation. Biochemical and biophysical research communications 379, 167-170.

Luke, G. A., de Felipe, P., Lukashev, A., Kallioinen, S. E., Bruno, E. A., and Ryan, M. D. (2008). Occurrence, function and evolutionary origins of '2A-like' sequences in virus genomes. The Journal of general virology 89, 1036-1042.

Mane, V. P., Heuer, M. A., Hillyer, P., Navarro, M. B., and Rabin, R. L. (2008). Systematic method for determining an ideal housekeeping gene for real-time PCR analysis. Journal of biomolecular techniques: JBT 19, 342-347.

Novoa, E. M., and Ribas de Pouplana, L. (2012). Speeding with control: codon usage, tRNAs, and ribosomes. Trends in genetics: TIG 28, 574-581.

Pedelacq, J. D., Cabantous, S., Tran, T., Terwilliger, T. C., and Waldo, G. S. (2006). Engineering and characterization of a superfolder green fluorescent protein. Nature biotechnology 24, 79-88.

Pfeiffer, B. D., Ngo, T. T., Hibbard, K. L., Murphy, C., Jenett, A., Truman, J. W., and Rubin, G. M. (2010). Refinement of tools for targeted gene expression in Drosophila. Genetics 186, 735-755.

Port F, Chen H M, Lee T, Bullock S L. Optimized CRISPR/Cas tools for efficient germline and somatic genome engineering in Drosophila. Proc Natl Acad Sci USA. 2014 Jul. 22; 111(29): E2967-76.

Reddy, P., Zehring, W. A., Wheeler, D. A., Pirrotta, V., Hadfield, C., Hall, J. C., and Rosbash, M. (1984). Molecular analysis of the period locus in Drosophila melanogaster and identification of a transcript involved in biological rhythms. Cell 38, 701-710.

Shaner, N. C., Lin, M. Z., McKeown, M. R., Steinbach, P. A., Hazelwood, K. L., Davidson, M. W., and Tsien, R. Y. (2008). Improving the photostability of bright monomeric orange and red fluorescent proteins. Nat Methods 5, 545-551.

Szymczak, A. L., Workman, C. J., Wang, Y., Vignali, K. M., Dilioglou, S., Vanin, E. F., and Vignali, D. A. (2004). Addendum: Correction of multi-gene deficiency in vivo using a single 'self-cleaving' 2A peptide-based retroviral vector. Nature biotechnology 22, 760.

Yang, S., Cohen, C. J., Peng, P. D., Zhao, Y., Cassard, L., Yu, Z., Zheng, Z., Jones, S., Restifo, N. P., Rosenberg, S. A., et al. (2008). Development of optimal bicistronic lentiviral vectors facilitates high-level TCR gene expression and robust tumor cell recognition. Gene therapy 15, 1411-1423.

Zhao, M. L., Sable, E. O., Iverson, L. E., and Wu, C. F. (1995). Functional expression of Shaker K+ channels in cultured Drosophila "giant" neurons derived from Sh cDNA transformants: distinct properties, distribution, and turnover. The Journal of neuroscience: the official journal of the Society for Neuroscience 15, 1406-1418.

Zhou, J. H., Zhang, J., Chen, H. T., Ma, L. N., Ding, Y. Z., Pejsak, Z., and Liu, Y. S. (2011). The codon usage model of the context flanking each cleavage site in the polyprotein of foot-and-mouth disease virus. Infection, genetics and evolution: journal of molecular epidemiology and evolutionary genetics in infectious diseases 11, 1815-1819.

What is claimed is:

1. A protein quantitation reporter linker nucleic acid molecule for quantifying a protein of interest in a host cell, the protein quantitation reporter:
   (i) encoding a cleavable peptide having the amino acid sequence of SEQ ID NO: 1, 2 or 17; and
   (ii) being a nucleic acid molecule having the nucleic acid sequence in which at least 50% of the codons encoding the amino acid sequence of SEQ ID NO: 1, 2 or 17 are de-optimized in function of the host cell.

2. The protein quantitation reporter linker nucleic acid molecule of claim 1 being a deoxyribonucleic (DNA) molecule.

3. The protein quantitation reporter linker nucleic acid molecule of claim 1, wherein at least 80% of the codons are de-optimized in function of the host cell.

4. A vector for quantifying a protein of interest in a host cell, said vector comprising a first nucleic acid molecule encoding the protein quantitation reporter linker nucleic acid molecule of claim 1.

5. The vector of claim 4, further comprising a second nucleic acid molecule encoding a reporter protein operatively linked to the first nucleic acid molecule so that the first nucleic acid molecule and second nucleic acid molecule are transcribed as a single messenger RNA transcript from the vector.

6. The vector of claim 5, wherein the reporter protein is selected from the group consisting of a fluorescent protein, an antibiotic-resistance protein, an immunoglobulin protein, an ion channel, a transcription factor, a ribosomal protein, an enzyme and a receptor.

7. The vector of claim 6, wherein the fluorescent protein is selected from the group consisting of a green-fluorescent protein (GFP), a red fluorescent protein (RFP), a yellow fluorescent protein (YFP), a blue fluorescent protein (BFP) and a cyan fluorescent protein (CFP).

8. The vector of claim 4, further comprising a third nucleic acid molecule encoding a protein of interest operatively linked to the first nucleic acid molecule so that the first nucleic acid molecule and the third nucleic acid molecule are transcribed as a single messenger RNA transcript from the vector.

9. The vector of claim 4, further comprising a second nucleic acid molecule encoding a reporter protein and a third nucleic acid molecule encoding a protein of interest, wherein the second nucleic acid molecule and the third nucleic acid molecule are operatively linked to the first nucleic acid molecule and wherein the first nucleic acid molecule is located between the second nucleic acid molecule and the third nucleic acid molecule, so that the that the first nucleic acid molecule, the second nucleic acid molecule and the third nucleic acid molecule are transcribed as a single messenger RNA transcript from the vector.

10. The vector of claim 9, wherein the second nucleic acid molecule is upstream of the third nucleic acid molecule.

11. The vector of claim 9, wherein the second nucleic acid molecule is downstream of the third nucleic acid molecule.

12. A method for quantifying a protein of interest in a host or a host cell, said method comprising (i) expressing the vector of claim 9 in the host or the host cell so as to cause the generation of a nucleic acid transcript encoding a poly-protein, wherein the poly-protein comprises the protein of interest, a cleavable peptide and a reporter protein and wherein the cleavable peptide can be cleaved during the translation of the nucleic acid transcript to generate a cleaved reporter protein and (ii) measuring a signal associated with the cleaved reporter protein to quantify the protein of interest.

13. The method of claim 12, wherein the reporter protein is a fluorescent protein and step (ii) further comprises determining the fluorescence associated with the cleaved reporter protein.

14. The method of claim 12, wherein the host cell is a living cell.

15. The method of claim 12, wherein the host cell is a single cell.

16. The protein quantitation reporter linker nucleic acid molecule of claim 1, wherein the cleavable peptide further comprises a GSG tripeptide.

17. The protein quantitation reporter linker nucleic acid molecule of claim 1 encoding the amino acid sequence of SEQ ID NO: 2 and having the nucleic acid sequence of SEQ ID NO: 86 or 87.

18. The protein quantitation reporter linker nucleic acid molecule of claim 1 encoding the amino acid sequence of SEQ ID NO: 1 and having the nucleic acid sequence of SEQ ID NO: 90, 91 or 92.

19. The protein quantitation reporter linker nucleic acid molecule of claim 16 having the nucleic acid sequence of SEQ ID NO: 82.

20. The protein quantitation reporter linker nucleic acid molecule of claim 16 having the nucleic acid sequence of SEQ ID NO: 83.

21. The protein quantitation reporter linker nucleic acid molecule of claim 16 having the nucleic acid sequence of SEQ ID NO: 84.

* * * * *

SEQUENCE LISTING

```
<160> NUMBER OF SEQ ID NOS: 143

<210> SEQ ID NO 1
<211> LENGTH: 19
<212> TYPE: PRT
<213> ORGANISM: Porcine teschovirus

<400> SEQUENCE: 1

Ala Thr Asn Phe Ser Leu Leu Lys Gln Ala Gly Asp Val Glu Glu Asn
1               5                   10                  15

Pro Gly Pro

<210> SEQ ID NO 2
<211> LENGTH: 18
<212> TYPE: PRT
<213> ORGANISM: Thosea asigna insect virus

<400> SEQUENCE: 2

Glu Gly Arg Gly Ser Leu Leu Thr Cys Gly Asp Val Glu Glu Asn Pro
1               5                   10                  15

Gly Pro

<210> SEQ ID NO 3
<211> LENGTH: 22
<212> TYPE: PRT
<213> ORGANISM: Artificial Sequence
<220> FEATURE:
<223> OTHER INFORMATION: GSG-modified P2A peptide

<400> SEQUENCE: 3

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 4
<211> LENGTH: 57
```

```
<212> TYPE: DNA
<213> ORGANISM: Porcine teschovirus

<400> SEQUENCE: 4
gctactaact tcagcctgct gaagcaggct ggagacgtgg aggagaaccc tggacct       57

<210> SEQ ID NO 5
<211> LENGTH: 66
<212> TYPE: DNA
<213> ORGANISM: Artificial Sequence
<220> FEATURE:
<223> OTHER INFORMATION: Codon optimized sequence encoding the P2A
      peptide

<400> SEQUENCE: 5
ggaagcggag ccacaaactt cagtctcctg aaacaggcag gcgatgtgga ggagaatccc   60
ggccca                                                               66

<210> SEQ ID NO 6
<211> LENGTH: 21
<212> TYPE: PRT
<213> ORGANISM: Artificial Sequence
<220> FEATURE:
<223> OTHER INFORMATION: GSG-modified T2A peptide

<400> SEQUENCE: 6

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 7
<211> LENGTH: 54
<212> TYPE: DNA
<213> ORGANISM: Thosea asigna insect virus

<400> SEQUENCE: 7
gagggcagag gaagtctgct aacatgcggt gacgtcgagg agaatcctgg acct          54

<210> SEQ ID NO 8
<211> LENGTH: 63
<212> TYPE: DNA
<213> ORGANISM: Artificial Sequence
<220> FEATURE:
<223> OTHER INFORMATION: Codon optimized sequence encoding the T2A
      peptide

<400> SEQUENCE: 8
ggaagcggag aggggagagg gtctctgctg acctgcgggg atgtcgagga gaacccggc    60 ccc                                                                  63

<210> SEQ ID NO 9
<211> LENGTH: 66
<212> TYPE: DNA
<213> ORGANISM: Artificial Sequence
<220> FEATURE:
<223> OTHER INFORMATION: Variation 1 of SEQ ID NO: 4

<400> SEQUENCE: 9
ggaagcggag cgacgaattt tagtctacta aacaagcgg gtgatgtaga agaaaatccg    60
ggtccg                                                               66

<210> SEQ ID NO 10
```

```
<211> LENGTH: 66
<212> TYPE: DNA
<213> ORGANISM: Artificial Sequence
<220> FEATURE:
<223> OTHER INFORMATION: Variation 2 of SEQ ID NO: 4

<400> SEQUENCE: 10
ggaagcggag cgacgaattt tagtctacta aaacaagcgg gtgatgtaga agaaaaccct      60
ggacct                                                                66

<210> SEQ ID NO 11
<211> LENGTH: 66
<212> TYPE: DNA
<213> ORGANISM: Artificial Sequence
<220> FEATURE:
<223> OTHER INFORMATION: Variation 3 od SEQ ID NO: 4

<400> SEQUENCE: 11
ggaagcggag cgacgaattt tagtctactg aaacaagcgg gagacgtgga ggaaaaccct      60
ggacct                                                                66

<210> SEQ ID NO 12
<211> LENGTH: 66
<212> TYPE: DNA
<213> ORGANISM: Artificial Sequence
<220> FEATURE:
<223> OTHER INFORMATION: Variation 4 of SEQ ID NO: 4

<400> SEQUENCE: 12
ggaagcggag ctactaactt cagcctgctg aagcaggctg gagacgtgga ggagaatccg      60
ggtccg                                                                66

<210> SEQ ID NO 13
<211> LENGTH: 66
<212> TYPE: DNA
<213> ORGANISM: Artificial Sequence
<220> FEATURE:
<223> OTHER INFORMATION: Mutant of SEQ ID NO: 4

<400> SEQUENCE: 13
ggaagcggag ctactaactt cagcctgctg aagcaggctg gagacgtgga ggagaacgcg      60
gcgcct                                                                66

<210> SEQ ID NO 14
<211> LENGTH: 63
<212> TYPE: DNA
<213> ORGANISM: Artificial Sequence
<220> FEATURE:
<223> OTHER INFORMATION: Variation 1 of SEQ ID NO: 6

<400> SEQUENCE: 14
ggaagcggag aaggtcgtgg tagtctacta acgtgtggtg atgtagaaga aaatcctgga      60
cct                                                                   63

<210> SEQ ID NO 15
<211> LENGTH: 63
<212> TYPE: DNA
<213> ORGANISM: Artificial Sequence
<220> FEATURE:
<223> OTHER INFORMATION: Variation 2 of SEQ ID NO: 6

<400> SEQUENCE: 15
ggaagcggag aaggtcgtgg tagtctacta acgtgtggtg acgtcgagga aaatcctgga      60
```

-continued

```
cct                                                             63

<210> SEQ ID NO 16
<211> LENGTH: 63
<212> TYPE: DNA
<213> ORGANISM: Artificial Sequence
<220> FEATURE:
<223> OTHER INFORMATION: Variation 3 of SEQ ID NO: 6

<400> SEQUENCE: 16
ggaagcggag agggacgcgg atccctgctg acctgcggcg atgtggagga gaaccccgga   60
ccg                                                             63

<210> SEQ ID NO 17
<211> LENGTH: 22
<212> TYPE: PRT
<213> ORGANISM: Foot-and-mouth disease virus

<400> SEQUENCE: 17

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 18
<211> LENGTH: 20
<212> TYPE: PRT
<213> ORGANISM: Equine rhinitis A virus

<400> SEQUENCE: 18

Gln Cys Thr Asn Tyr Ala Leu Leu Lys Leu Ala Gly Asp Val Glu Ser
1               5                   10                  15

Asn Pro Gly Pro
            20

<210> SEQ ID NO 19
<211> LENGTH: 18
<212> TYPE: PRT
<213> ORGANISM: Thosea asigna insect virus

<400> SEQUENCE: 19

Glu Gly Arg Gly Ser Leu Leu Thr Cys Gly Asp Val Glu Glu Asn Pro
1               5                   10                  15

Gly Pro

<210> SEQ ID NO 20
<211> LENGTH: 19
<212> TYPE: PRT
<213> ORGANISM: Porcine teschovirus

<400> SEQUENCE: 20

Ala Thr Asn Phe Ser Leu Leu Lys Gln Ala Gly Asp Val Glu Glu Asn
1               5                   10                  15

Pro Gly Pro

<210> SEQ ID NO 21
<211> LENGTH: 22
<212> TYPE: PRT
<213> ORGANISM: Artificial Sequence
<220> FEATURE:
<223> OTHER INFORMATION: Consensus sequence from F2A, E2A, T2A and P2A
      peptides
```

```
<220> FEATURE:
<221> NAME/KEY: VARIANT
<222> LOCATION: (1)..(1)
<223> OTHER INFORMATION: V or absent
<220> FEATURE:
<221> NAME/KEY: VARIANT
<222> LOCATION: (2)..(2)
<223> OTHER INFORMATION: K or absent
<220> FEATURE:
<221> NAME/KEY: VARIANT
<222> LOCATION: (3)..(3)
<223> OTHER INFORMATION: Q or absent
<220> FEATURE:
<221> NAME/KEY: VARIANT
<222> LOCATION: (4)..(4)
<223> OTHER INFORMATION: T, C, A or absent
<220> FEATURE:
<221> NAME/KEY: VARIANT
<222> LOCATION: (5)..(5)
<223> OTHER INFORMATION: L, T or E
<220> FEATURE:
<221> NAME/KEY: VARIANT
<222> LOCATION: (6)..(6)
<223> OTHER INFORMATION: N or G
<220> FEATURE:
<221> NAME/KEY: VARIANT
<222> LOCATION: (7)..(7)
<223> OTHER INFORMATION: F, Y or R
<220> FEATURE:
<221> NAME/KEY: VARIANT
<222> LOCATION: (8)..(8)
<223> OTHER INFORMATION: D, A, G or S
<220> FEATURE:
<221> NAME/KEY: VARIANT
<222> LOCATION: (9)..(9)
<223> OTHER INFORMATION: L or S
<220> FEATURE:
<221> NAME/KEY: VARIANT
<222> LOCATION: (11)..(11)
<223> OTHER INFORMATION: K or L
<220> FEATURE:
<221> NAME/KEY: VARIANT
<222> LOCATION: (12)..(12)
<223> OTHER INFORMATION: L, T or Q
<220> FEATURE:
<221> NAME/KEY: VARIANT
<222> LOCATION: (13)..(13)
<223> OTHER INFORMATION: A or C
<220> FEATURE:
<221> NAME/KEY: VARIANT
<222> LOCATION: (18)..(18)
<223> OTHER INFORMATION: S or E

<400> SEQUENCE: 21

Xaa Xaa Xaa Xaa Xaa Xaa Xaa Xaa Xaa Leu Xaa Xaa Xaa Gly Asp Val
1               5                   10                  15

Glu Xaa Asn Pro Gly Pro
            20

<210> SEQ ID NO 22
<211> LENGTH: 19
<212> TYPE: PRT
<213> ORGANISM: Artificial Sequence
<220> FEATURE:
<223> OTHER INFORMATION: Consensus sequence from T2A and P2A peptides
<220> FEATURE:
<221> NAME/KEY: VARIANT
<222> LOCATION: (1)..(1)
<223> OTHER INFORMATION: A or absent
<220> FEATURE:
<221> NAME/KEY: VARIANT
<222> LOCATION: (2)..(2)
<223> OTHER INFORMATION: E or T
<220> FEATURE:
<221> NAME/KEY: VARIANT
<222> LOCATION: (3)..(3)
```

```
<223> OTHER INFORMATION: G or N
<220> FEATURE:
<221> NAME/KEY: VARIANT
<222> LOCATION: (4)..(4)
<223> OTHER INFORMATION: R or F
<220> FEATURE:
<221> NAME/KEY: VARIANT
<222> LOCATION: (5)..(5)
<223> OTHER INFORMATION: G or S
<220> FEATURE:
<221> NAME/KEY: VARIANT
<222> LOCATION: (6)..(6)
<223> OTHER INFORMATION: S or L
<220> FEATURE:
<221> NAME/KEY: VARIANT
<222> LOCATION: (8)..(8)
<223> OTHER INFORMATION: L or K
<220> FEATURE:
<221> NAME/KEY: VARIANT
<222> LOCATION: (9)..(9)
<223> OTHER INFORMATION: T or Q
<220> FEATURE:
<221> NAME/KEY: VARIANT
<222> LOCATION: (10)..(10)
<223> OTHER INFORMATION: C or A

<400> SEQUENCE: 22

Xaa Xaa Xaa Xaa Xaa Xaa Leu Xaa Xaa Xaa Gly Asp Val Glu Glu Asn
1               5                   10                  15

Pro Gly Pro

<210> SEQ ID NO 23
<211> LENGTH: 25
<212> TYPE: PRT
<213> ORGANISM: Artificial Sequence
<220> FEATURE:
<223> OTHER INFORMATION: GSG-modified consensus sequence from F2A, E2A,
      T2A and P2A peptides
<220> FEATURE:
<221> NAME/KEY: VARIANT
<222> LOCATION: (4)..(4)
<223> OTHER INFORMATION: V or absent
<220> FEATURE:
<221> NAME/KEY: VARIANT
<222> LOCATION: (5)..(5)
<223> OTHER INFORMATION: K or absent
<220> FEATURE:
<221> NAME/KEY: VARIANT
<222> LOCATION: (6)..(6)
<223> OTHER INFORMATION: Q or absent
<220> FEATURE:
<221> NAME/KEY: VARIANT
<222> LOCATION: (7)..(7)
<223> OTHER INFORMATION: T, C, A or absent
<220> FEATURE:
<221> NAME/KEY: VARIANT
<222> LOCATION: (8)..(8)
<223> OTHER INFORMATION: L, T or E
<220> FEATURE:
<221> NAME/KEY: VARIANT
<222> LOCATION: (9)..(9)
<223> OTHER INFORMATION: N or G
<220> FEATURE:
<221> NAME/KEY: VARIANT
<222> LOCATION: (10)..(10)
<223> OTHER INFORMATION: F, Y or R
<220> FEATURE:
<221> NAME/KEY: VARIANT
<222> LOCATION: (11)..(11)
<223> OTHER INFORMATION: D, A, G or S
<220> FEATURE:
<221> NAME/KEY: VARIANT
<222> LOCATION: (12)..(12)
<223> OTHER INFORMATION: L or S
<220> FEATURE:
<221> NAME/KEY: VARIANT
```

```
<222> LOCATION: (14)..(14)
<223> OTHER INFORMATION: K or L
<220> FEATURE:
<221> NAME/KEY: VARIANT
<222> LOCATION: (15)..(15)
<223> OTHER INFORMATION: L, T or Q
<220> FEATURE:
<221> NAME/KEY: VARIANT
<222> LOCATION: (16)..(16)
<223> OTHER INFORMATION: A or C
<220> FEATURE:
<221> NAME/KEY: VARIANT
<222> LOCATION: (21)..(21)
<223> OTHER INFORMATION: S or E

<400> SEQUENCE: 23

Gly Ser Gly Xaa Xaa Xaa Xaa Xaa Xaa Xaa Xaa Xaa Leu Xaa Xaa Xaa
1               5                   10                  15

Gly Asp Val Glu Xaa Asn Pro Gly Pro
            20                  25

<210> SEQ ID NO 24
<211> LENGTH: 22
<212> TYPE: PRT
<213> ORGANISM: Artificial Sequence
<220> FEATURE:
<223> OTHER INFORMATION: GSG-modified consensus sequence from T2A and
      P2A peptides
<220> FEATURE:
<221> NAME/KEY: VARIANT
<222> LOCATION: (4)..(4)
<223> OTHER INFORMATION: A or absent
<220> FEATURE:
<221> NAME/KEY: VARIANT
<222> LOCATION: (5)..(5)
<223> OTHER INFORMATION: E or T
<220> FEATURE:
<221> NAME/KEY: VARIANT
<222> LOCATION: (6)..(6)
<223> OTHER INFORMATION: G or N
<220> FEATURE:
<221> NAME/KEY: VARIANT
<222> LOCATION: (7)..(7)
<223> OTHER INFORMATION: R or F
<220> FEATURE:
<221> NAME/KEY: VARIANT
<222> LOCATION: (8)..(8)
<223> OTHER INFORMATION: G or S
<220> FEATURE:
<221> NAME/KEY: VARIANT
<222> LOCATION: (9)..(9)
<223> OTHER INFORMATION: S or L
<220> FEATURE:
<221> NAME/KEY: VARIANT
<222> LOCATION: (11)..(11)
<223> OTHER INFORMATION: L or K
<220> FEATURE:
<221> NAME/KEY: VARIANT
<222> LOCATION: (12)..(12)
<223> OTHER INFORMATION: T or Q
<220> FEATURE:
<221> NAME/KEY: VARIANT
<222> LOCATION: (13)..(13)
<223> OTHER INFORMATION: C or A

<400> SEQUENCE: 24

Gly Ser Gly Xaa Xaa Xaa Xaa Xaa Xaa Leu Xaa Xaa Xaa Gly Asp Val
1               5                   10                  15

Glu Glu Asn Pro Gly Pro
            20

<210> SEQ ID NO 25
<211> LENGTH: 75
```

```
<212> TYPE: DNA
<213> ORGANISM: Artificial Sequence
<220> FEATURE:
<223> OTHER INFORMATION: Nucleic acid molecule encoding the peptide
      having the amino acid sequence of SEQ ID NO: 23 or SEQ ID NO: 24
<220> FEATURE:
<221> NAME/KEY: misc_feature
<222> LOCATION: (1)..(63)
<223> OTHER INFORMATION: Represent any nucleic acid capable of forming
      codons encoding residues 1 to 21 of SEQ ID NO: 23 or residues 1 to
      18 of SEQ ID NO: 24
<220> FEATURE:
<221> NAME/KEY: misc_feature
<222> LOCATION: (69)..(69)
<223> OTHER INFORMATION: T or U
<220> FEATURE:
<221> NAME/KEY: misc_feature
<222> LOCATION: (75)..(75)
<223> OTHER INFORMATION: T or U

<400> SEQUENCE: 25
nnnnnnnnnn nnnnnnnnnn nnnnnnnnnn nnnnnnnnnn nnnnnnnnnn nnnnnnnnnn    60
nnnaayccng gaccn                                                     75

<210> SEQ ID NO 26
<211> LENGTH: 75
<212> TYPE: DNA
<213> ORGANISM: Artificial Sequence
<220> FEATURE:
<223> OTHER INFORMATION: Nucleic acid molecule encoding the peptide
      having the amino acid sequence of SEQ ID NO: 23 or SEQ ID NO: 24
<220> FEATURE:
<221> NAME/KEY: misc_feature
<222> LOCATION: (1)..(63)
<223> OTHER INFORMATION: Represent any nucleic acid capable of forming
      codons encoding residues 1 to 21 of SEQ ID NO: 23 or residues 1 to
      18 of SEQ ID NO: 24

<400> SEQUENCE: 26
nnnnnnnnnn nnnnnnnnnn nnnnnnnnnn nnnnnnnnnn nnnnnnnnnn nnnnnnnnnn    60
nnnaaycctg gacct                                                     75

<210> SEQ ID NO 27
<211> LENGTH: 28
<212> TYPE: PRT
<213> ORGANISM: Artificial Sequence
<220> FEATURE:
<223> OTHER INFORMATION: GSG-modified CHYSEL

<400> SEQUENCE: 27

Gly Ser Gly Gly Ile Phe Asn Ala His Tyr Ala Gly Tyr Phe Ala Asp
1               5                   10                  15

Leu Leu Ile His Asp Ile Glu Thr Asn Pro Gly Pro
            20                  25

<210> SEQ ID NO 28
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 28

Gly Ser Gly Gly Ile Phe Asn Ala His Tyr Ala Gly Tyr Phe Ala Asp
1               5                   10                  15

Leu Leu Ile His Asp Ile Glu Thr Asn Pro Gly Pro
            20                  25
```

```
<210> SEQ ID NO 29
<211> LENGTH: 28
<212> TYPE: PRT
<213> ORGANISM: Artificial Sequence
<220> FEATURE:
<223> OTHER INFORMATION: GSG-modified CHYSEL

<400> SEQUENCE: 29

Gly Ser Gly Arg Ile Phe Asn Ala His Tyr Ala Gly Tyr Phe Ala Asp
1               5                   10                  15

Leu Leu Ile His Asp Ile Glu Thr Asn Pro Gly Pro
            20                  25

<210> SEQ ID NO 30
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 30

Gly Ser Gly His Val Phe Glu Thr His Tyr Ala Gly Tyr Phe Ser Asp
1               5                   10                  15

Leu Leu Ile His Asp Val Glu Thr Asn Pro Gly Pro
            20                  25

<210> SEQ ID NO 31
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 31

Gly Ser Gly Lys Ala Val Arg Gly Tyr His Ala Asp Tyr Tyr Lys Gln
1               5                   10                  15

Arg Leu Ile His Asp Val Glu Met Asn Pro Gly Pro
            20                  25

<210> SEQ ID NO 32
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 32

Gly Ser Gly Arg Ala Val Arg Ala Tyr His Ala Asp Tyr Tyr Lys Gln
1               5                   10                  15

Arg Leu Ile His Asp Val Glu Met Asn Pro Gly Pro
            20                  25

<210> SEQ ID NO 33
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 33

Gly Ser Gly Lys Ala Val Arg Gly Tyr His Ala Asp Tyr Tyr Arg Gln
1               5                   10                  15

Arg Leu Ile His Asp Val Glu Thr Asn Pro Gly Pro
            20                  25
```

<210> SEQ ID NO 34
<211> LENGTH: 28
<212> TYPE: PRT
<213> ORGANISM: Artificial Sequence
<220> FEATURE:
<223> OTHER INFORMATION: GSG-modified CHYSEL peptide

<400> SEQUENCE: 34

Gly Ser Gly Lys His Val Arg Glu Tyr His Ala Ala Tyr Tyr Lys Gln
1               5                   10                  15

Arg Leu Met His Asp Val Glu Thr Asn Pro Gly Pro
            20                  25

<210> SEQ ID NO 35
<211> LENGTH: 29
<212> TYPE: PRT
<213> ORGANISM: Artificial Sequence
<220> FEATURE:
<223> OTHER INFORMATION: GSG-modified CHYSEL peptide

<400> SEQUENCE: 35

Gly Ser Gly Met His Ser Asp Glu Met Asp Phe Ala Gly Gly Lys Phe
1               5                   10                  15

Leu Asn Gln Cys Gly Asp Val Glu Thr Asn Pro Gly Pro
            20                  25

<210> SEQ ID NO 36
<211> LENGTH: 29
<212> TYPE: PRT
<213> ORGANISM: Artificial Sequence
<220> FEATURE:
<223> OTHER INFORMATION: GSG-modified CHYSEL peptide

<400> SEQUENCE: 36

Gly Ser Gly Met His Asn Asp Glu Met Asp Tyr Ser Gly Gly Lys Phe
1               5                   10                  15

Leu Asn Gln Cys Gly Asp Val Glu Ser Asn Pro Gly Pro
            20                  25

<210> SEQ ID NO 37
<211> LENGTH: 29
<212> TYPE: PRT
<213> ORGANISM: Artificial Sequence
<220> FEATURE:
<223> OTHER INFORMATION: GSG-modified CHYSEL

<400> SEQUENCE: 37

Gly Ser Gly Met His Ser Asp Glu Met Asp Phe Ala Gly Gly Lys Phe
1               5                   10                  15

Leu Asn Gln Cys Gly Asp Val Glu Thr Asn Pro Gly Pro
            20                  25

<210> SEQ ID NO 38
<211> LENGTH: 29
<212> TYPE: PRT
<213> ORGANISM: Artificial Sequence
<220> FEATURE:
<223> OTHER INFORMATION: GSG-modified CHYSEL

<400> SEQUENCE: 38

Gly Ser Gly Tyr His Asp Lys Asp Met Asp Tyr Ala Gly Gly Lys Phe
1               5                   10                  15

Leu Asn Gln Cys Gly Asp Val Glu Thr Asn Pro Gly Pro

```
                       20                  25

<210> SEQ ID NO 39
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 39

Gly Ser Gly Leu Leu Asn Phe Asp Leu Leu Lys Leu Ala Gly Asp Val
1               5                   10                  15

Glu Ser Asn Pro Gly Pro
            20

<210> SEQ ID NO 40
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 40

Gly Ser Gly Leu Leu Asn Phe Asp Leu Leu Lys Leu Ala Gly Asp Val
1               5                   10                  15

Glu Ser Asn Pro Gly Pro
            20

<210> SEQ ID NO 41
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 41

Gly Ser Gly Leu Leu Asn Phe Asp Leu Leu Lys Leu Ala Gly Asp Val
1               5                   10                  15

Glu Ser Asn Pro Gly Pro
            20

<210> SEQ ID NO 42
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 42

Gly Ser Gly Leu Leu Asn Phe Asp Leu Leu Lys Leu Ala Gly Asp Met
1               5                   10                  15

Glu Ser Asn Pro Gly Pro
            20

<210> SEQ ID NO 43
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 43

Gly Ser Gly Leu Thr Asn Phe Asp Leu Leu Lys Leu Ala Gly Asp Val
1               5                   10                  15
```

Glu Ser Asn Pro Gly Pro
            20

<210> SEQ ID NO 44
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 44

Gly Ser Gly Leu Leu Asn Phe Asp Leu Leu Lys Leu Ala Gly Asp Val
1               5                   10                  15

Glu Ser Asn Pro Gly Pro
            20

<210> SEQ ID NO 45
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 45

Gly Ser Gly Leu Leu Ser Phe Asp Leu Leu Lys Leu Ala Gly Asp Val
1               5                   10                  15

Glu Ser Asn Pro Gly Pro
            20

<210> SEQ ID NO 46
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 46

Gly Ser Gly Met Cys Asn Phe Asp Leu Leu Lys Leu Ala Gly Asp Val
1               5                   10                  15

Glu Ser Asn Pro Gly Pro
            20

<210> SEQ ID NO 47
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 47

Gly Ser Gly Leu Leu Asn Phe Asp Leu Leu Lys Leu Ala Gly Asp Val
1               5                   10                  15

Glu Ser Asn Pro Gly Pro
            20

<210> SEQ ID NO 48
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 48

Gly Ser Gly Cys Thr Asn Tyr Ser Leu Leu Lys Leu Ala Gly Asp Val
1               5                   10                  15

Glu Ser Asn Pro Gly Pro
            20

<210> SEQ ID NO 49
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 49

Gly Ser Gly Gly Ala Thr Asn Phe Ser Leu Leu Lys Leu Ala Gly Asp
1               5                   10                  15

Val Glu Leu Asn Pro Gly Pro
            20

<210> SEQ ID NO 50
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 50

Gly Ser Gly Gly Ala Thr Asn Phe Asp Leu Leu Lys Leu Ala Gly Asp
1               5                   10                  15

Val Glu Ser Asn Pro Gly Pro
            20

<210> SEQ ID NO 51
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 51

Gly Ser Gly Gly Pro Gly Ala Thr Asn Phe Ser Leu Leu Lys Gln Ala
1               5                   10                  15

Gly Asp Val Glu Glu Asn Pro Gly Pro
            20                  25

<210> SEQ ID NO 52
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 52

Gly Ser Gly Gly Pro Gly Ala Thr Asn Phe Ser Leu Leu Lys Gln Ala
1               5                   10                  15

Gly Asp Val Glu Glu Asn Pro Gly Pro
            20                  25

<210> SEQ ID NO 53
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 53

Gly Ser Gly Gly Pro Gly Ala Ser Ser Phe Ser Leu Leu Lys Gln Ala

Gly Asp Val Glu Glu Asn Pro Gly Pro
            20                  25

<210> SEQ ID NO 54
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 54

Gly Ser Gly Gly Pro Gly Ala Ser Asn Phe Ser Leu Leu Lys Gln Ala
1               5                   10                  15

Gly Asp Val Glu Glu Asn Pro Gly Pro
            20                  25

<210> SEQ ID NO 55
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 55

Gly Ser Gly Gly Pro Gly Ala Ala Asn Phe Ser Leu Leu Arg Gln Ala
1               5                   10                  15

Gly Asp Val Glu Glu Asn Pro Gly Pro
            20                  25

<210> SEQ ID NO 56
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 56

Gly Ser Gly Gly Pro Gly Ala Thr Asn Phe Ser Leu Leu Lys Gln Ala
1               5                   10                  15

Gly Asp Val Glu Glu Asn Pro Gly Pro
            20                  25

<210> SEQ ID NO 57
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 57

Gly Ser Gly Gly Pro Gly Ala Thr Asn Phe Ser Leu Leu Lys Gln Ala
1               5                   10                  15

Gly Asp Val Glu Glu Asn Pro Gly Pro
            20                  25

<210> SEQ ID NO 58
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 58

```
Gly Ser Gly Gly Pro Gly Ala Thr Asn Phe Ser Leu Leu Lys Gln Ala
1               5                   10                  15
Gly Asp Ile Glu Glu Asn Pro Gly Pro
            20                  25
```

<210> SEQ ID NO 59
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 59

```
Gly Ser Gly Gly Pro Gly Ala Thr Asn Phe Ser Leu Leu Lys Gln Ala
1               5                   10                  15
Gly Asp Val Glu Glu Asn Pro Gly Pro
            20                  25
```

<210> SEQ ID NO 60
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 60

```
Gly Ser Gly Gly Pro Gly Ala Thr Asn Phe Ser Leu Leu Lys Gln Ala
1               5                   10                  15
Gly Asp Val Glu Glu Asn Pro Gly Pro
            20                  25
```

<210> SEQ ID NO 61
<211> LENGTH: 25
<212> TYPE: PRT
<213> ORGANISM: Artificial Sequence
<220> FEATURE:
<223> OTHER INFORMATION: GSG-modified CHYSEL

<400> SEQUENCE: 61

```
Gly Ser Gly Gly Pro Gly Ala Thr Asn Phe Ser Leu Leu Lys Arg Ala
1               5                   10                  15
Gly Asp Val Glu Glu Asn Pro Gly Pro
            20                  25
```

<210> SEQ ID NO 62
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 62

```
Gly Ser Gly Phe Leu Arg Lys Arg Thr Gln Leu Leu Met Ser Gly Asp
1               5                   10                  15
Val Glu Ser Asn Pro Gly Pro
            20
```

<210> SEQ ID NO 63
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 63

Gly Ser Gly Glu Ala Ala Arg Gln Met Leu Leu Leu Ser Gly Asp
1               5                   10                  15

Val Glu Thr Asn Pro Gly Pro
            20

<210> SEQ ID NO 64
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 64

Gly Ser Gly Gly Ser Trp Thr Asp Ile Leu Leu Leu Ser Gly Asp
1               5                   10                  15

Val Glu Thr Asn Pro Gly Pro
            20

<210> SEQ ID NO 65
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 65

Gly Ser Gly Gly Ser Trp Thr Asp Ile Leu Leu Leu Ser Gly Asp
1               5                   10                  15

Val Glu Thr Asn Pro Gly Pro
            20

<210> SEQ ID NO 66
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 66

Gly Ser Gly Gly Ser Trp Thr Asp Ile Leu Leu Leu Trp Ser Gly Asp
1               5                   10                  15

Val Glu Thr Asn Pro Gly Pro
            20

<210> SEQ ID NO 67
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 67

Gly Ser Gly Thr Arg Ala Glu Ile Glu Asp Glu Leu Ile Arg Ala Gly
1               5                   10                  15

Ile Glu Ser Asn Pro Gly Pro
            20

<210> SEQ ID NO 68
<211> LENGTH: 23
<212> TYPE: PRT
<213> ORGANISM: Artificial Sequence
<220> FEATURE:
<223> OTHER INFORMATION: GSG-modified CHYSEL

```
<400> SEQUENCE: 68

Gly Ser Gly Arg Ala Glu Gly Arg Gly Ser Leu Leu Thr Cys Gly Asp
1               5                   10                  15

Val Glu Glu Asn Pro Gly Pro
            20

<210> SEQ ID NO 69
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 69

Gly Ser Gly Gln Gly Ala Gly Arg Gly Ser Leu Val Thr Cys Gly Asp
1               5                   10                  15

Val Glu Glu Asn Pro Gly Pro
            20

<210> SEQ ID NO 70
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 70

Gly Ser Gly Asn Tyr Pro Met Pro Glu Ala Leu Gln Lys Ile Ile Asp
1               5                   10                  15

Leu Glu Ser Asn Pro Pro Pro
            20

<210> SEQ ID NO 71
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 71

Gly Ser Gly Gly Thr Trp Glu Ser Val Leu Asn Leu Leu Ala Gly Asp
1               5                   10                  15

Ile Glu Leu Asn Pro Gly Pro
            20

<210> SEQ ID NO 72
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 72

Gly Ser Gly Ala Gln Gly Trp Val Pro Asp Leu Thr Val Asp Gly Asp
1               5                   10                  15

Val Glu Ser Asn Pro Gly Pro
            20

<210> SEQ ID NO 73
<211> LENGTH: 23
<212> TYPE: PRT
<213> ORGANISM: Artificial Sequence
<220> FEATURE:
<223> OTHER INFORMATION: GSG-modified CHYSEL
```

<400> SEQUENCE: 73

Gly Ser Gly Ile Gly Gly Gly Gln Lys Asp Leu Thr Gln Asp Gly Asp
1               5                   10                  15

Ile Glu Ser Asn Pro Gly Pro
            20

<210> SEQ ID NO 74
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 74

Gly Ser Gly Ala Gln Gly Trp Ala Pro Asp Leu Thr Gln Asp Gly Asp
1               5                   10                  15

Val Glu Ser Asn Pro Gly Pro
            20

<210> SEQ ID NO 75
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 75

Gly Ser Gly Ile Gly Gly Gly Gln Arg Asp Leu Thr Gln Asp Gly Asp
1               5                   10                  15

Ile Glu Ser Asn Pro Gly Pro
            20

<210> SEQ ID NO 76
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 76

Gly Ser Gly Val Gly Asp Arg Gly Ser Leu Leu Thr Cys Gly Asp Val
1               5                   10                  15

Glu Ser Asn Pro Gly Pro
            20

<210> SEQ ID NO 77
<211> LENGTH: 22
<212> TYPE: PRT
<213> ORGANISM: Artificial Sequence
<220> FEATURE:
<223> OTHER INFORMATION: GSG-modified CHYSEL

<400> SEQUENCE: 77

Gly Ser Gly Ser Gly Gly Arg Gly Ser Leu Leu Thr Ala Gly Asp Val
1               5                   10                  15

Glu Lys Asn Pro Gly Pro
            20

<210> SEQ ID NO 78
<211> LENGTH: 22
<212> TYPE: PRT
<213> ORGANISM: Artificial Sequence
<220> FEATURE:

<223> OTHER INFORMATION: GSG-modified CHYSEL

<400> SEQUENCE: 78

Gly Ser Gly Gly Asp Pro Ile Glu Asp Leu Thr Asp Asp Gly Asp Ile
1               5                   10                  15

Glu Lys Asn Pro Gly Pro
            20

<210> SEQ ID NO 79
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 79

Gly Ser Gly Ser Lys Phe Gln Ile Asp Arg Ile Leu Ile Ser Gly Asp
1               5                   10                  15

Ile Glu Leu Asn Pro Gly Pro
            20

<210> SEQ ID NO 80
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 80

Gly Ser Gly Ala Lys Phe Gln Ile Asp Lys Ile Leu Ile Ser Gly Asp
1               5                   10                  15

Val Glu Leu Asn Pro Gly Pro
            20

<210> SEQ ID NO 81
<211> LENGTH: 23
<212> TYPE: PRT
<213> ORGANISM: Artificial Sequence
<220> FEATURE:
<223> OTHER INFORMATION: GSG-modified CHYSEL

<400> SEQUENCE: 81

Gly Ser Gly Ser Lys Phe Gln Ile Asp Lys Ile Leu Ile Ser Gly Asp
1               5                   10                  15

Ile Glu Leu Asn Pro Gly Pro
            20

<210> SEQ ID NO 82
<211> LENGTH: 81
<212> TYPE: DNA
<213> ORGANISM: Artificial Sequence
<220> FEATURE:
<223> OTHER INFORMATION: PQR-encoding sequence using wilt-type F2A

<400> SEQUENCE: 82
ggttctggtg ctcctgtcaa acaaactctt aactttgatt tactcaaact ggctggggat      60
gtagaaagca atccaggtcc a                                                81

<210> SEQ ID NO 83
<211> LENGTH: 66
<212> TYPE: DNA
<213> ORGANISM: Artificial Sequence
<220> FEATURE:
<223> OTHER INFORMATION: Oligonucleotide

<400> SEQUENCE: 83
ggaagcggag cgacgaattt tagtctactg aaacaagcgg gagacgtgga ggaaaaccct    60
ggacct                                                               66

<210> SEQ ID NO 84
<211> LENGTH: 63
<212> TYPE: DNA
<213> ORGANISM: Artificial Sequence
<220> FEATURE:
<223> OTHER INFORMATION: Oligonucleotide

<400> SEQUENCE: 84
ggaagcggag aaggtcgtgg tagtctacta acgtgtggtg acgtcgagga aaatcctgga    60
cct                                                                  63

<210> SEQ ID NO 85
<211> LENGTH: 54
<212> TYPE: DNA
<213> ORGANISM: Artificial Sequence
<220> FEATURE:
<223> OTHER INFORMATION: Oligonucleotide

<400> SEQUENCE: 85
gagggacgcg gatccctgct gacctgcggc gatgtggagg agaaccccgg accg          54

<210> SEQ ID NO 86
<211> LENGTH: 54
<212> TYPE: DNA
<213> ORGANISM: Artificial Sequence
<220> FEATURE:
<223> OTHER INFORMATION: Oligonucleotide

<400> SEQUENCE: 86
gaaggtcgtg gtagtctact aacgtgtggt gatgtagaag aaaatcctgg acct          54

<210> SEQ ID NO 87
<211> LENGTH: 54
<212> TYPE: DNA
<213> ORGANISM: Artificial Sequence
<220> FEATURE:
<223> OTHER INFORMATION: Oligonucleotide

<400> SEQUENCE: 87
gaaggtcgtg gtagtctact aacgtgtggt gacgtcgagg aaaatcctgg acct          54

<210> SEQ ID NO 88
<211> LENGTH: 54
<212> TYPE: DNA
<213> ORGANISM: Artificial Sequence
<220> FEATURE:
<223> OTHER INFORMATION: Oligonucleotide

<400> SEQUENCE: 88
gagggcagag gaagtctgct aacatgcggt gacgtcgagg agaatgcggc gcct          54

<210> SEQ ID NO 89
<211> LENGTH: 90
<212> TYPE: DNA
<213> ORGANISM: Artificial Sequence
<220> FEATURE:
<223> OTHER INFORMATION: Oligonucleotide

<400> SEQUENCE: 89

```
gctatgactg tgatggcatt tcaggggcca ggtgccacta acttctccct tttaaaacaa      60 gcagggatg ttgaagaaaa tcccgggccc                                       90
```

<210> SEQ ID NO 90
<211> LENGTH: 57
<212> TYPE: DNA
<213> ORGANISM: Artificial Sequence
<220> FEATURE:
<223> OTHER INFORMATION: Oligonucleotide

<400> SEQUENCE: 90

```
gcgacgaatt ttagtctact aaaacaagcg ggtgatgtag aagaaaatcc gggtccg       57
```

<210> SEQ ID NO 91
<211> LENGTH: 57
<212> TYPE: DNA
<213> ORGANISM: Artificial Sequence
<220> FEATURE:
<223> OTHER INFORMATION: Oligonucleotide

<400> SEQUENCE: 91

```
gcgacgaatt ttagtctact aaaacaagcg ggtgatgtag aagaaaaccc tggacct       57
```

<210> SEQ ID NO 92
<211> LENGTH: 57
<212> TYPE: DNA
<213> ORGANISM: Artificial Sequence
<220> FEATURE:
<223> OTHER INFORMATION: Oligonucleotide

<400> SEQUENCE: 92

```
gcgacgaatt ttagtctact gaaacaagcg ggagacgtgg aggaaaaccc tggacct       57
```

<210> SEQ ID NO 93
<211> LENGTH: 57
<212> TYPE: DNA
<213> ORGANISM: Artificial Sequence
<220> FEATURE:
<223> OTHER INFORMATION: Oligonucleotide

<400> SEQUENCE: 93

```
gctactaact tcagcctgct gaagcaggct ggagacgtgg aggagaatcc gggtccg       57
```

<210> SEQ ID NO 94
<211> LENGTH: 57
<212> TYPE: DNA
<213> ORGANISM: Artificial Sequence
<220> FEATURE:
<223> OTHER INFORMATION: Oligonucleotide

<400> SEQUENCE: 94

```
gctactaact tcagcctgct gaagcaggct ggagacgtgg aggagaacgc ggcgcct       57
```

<210> SEQ ID NO 95
<211> LENGTH: 18
<212> TYPE: PRT
<213> ORGANISM: Artificial Sequence
<220> FEATURE:
<223> OTHER INFORMATION: Oligopeptide

<400> SEQUENCE: 95

```
Glu Gly Arg Gly Ser Leu Leu Thr Cys Gly Asp Val Glu Glu Asn Ala
1               5                   10                  15

Ala Pro
```

<210> SEQ ID NO 96
<211> LENGTH: 30
<212> TYPE: PRT
<213> ORGANISM: Artificial Sequence
<220> FEATURE:
<223> OTHER INFORMATION: Oligopeptide

<400> SEQUENCE: 96

Ala Met Thr Val Met Ala Phe Gln Gly Pro Gly Ala Thr Asn Phe Ser
1               5                   10                  15

Leu Leu Lys Gln Ala Gly Asp Val Glu Glu Asn Pro Gly Pro
            20                  25                  30

<210> SEQ ID NO 97
<211> LENGTH: 20
<212> TYPE: DNA
<213> ORGANISM: Artificial Sequence
<220> FEATURE:
<223> OTHER INFORMATION: Oligonucleotide

<400> SEQUENCE: 97
ctggaggtca gtgatgagca                                              20

<210> SEQ ID NO 98
<211> LENGTH: 20
<212> TYPE: DNA
<213> ORGANISM: Artificial Sequence
<220> FEATURE:
<223> OTHER INFORMATION: Oligonucleotide

<400> SEQUENCE: 98
tggaatggtg tggcaagtta                                              20

<210> SEQ ID NO 99
<211> LENGTH: 20
<212> TYPE: DNA
<213> ORGANISM: Artificial Sequence
<220> FEATURE:
<223> OTHER INFORMATION: Oligonucleotide

<400> SEQUENCE: 99
cgggttgcta acctggaata                                              20

<210> SEQ ID NO 100
<211> LENGTH: 20
<212> TYPE: DNA
<213> ORGANISM: Artificial Sequence
<220> FEATURE:
<223> OTHER INFORMATION: Oligonucleotide

<400> SEQUENCE: 100
cagtctccat caaggggaaa                                              20

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide

<400> SEQUENCE: 101
tgaacctctc gggacacttc                                              20

<210> SEQ ID NO 102
<211> LENGTH: 21

```
<212> TYPE: DNA
<213> ORGANISM: Artificial Sequence
<220> FEATURE:
<223> OTHER INFORMATION: Oligonucleotide

<400> SEQUENCE: 102
tgtggatatg gttgcattct g                                              21

<210> SEQ ID NO 103
<211> LENGTH: 20
<212> TYPE: DNA
<213> ORGANISM: Artificial Sequence
<220> FEATURE:
<223> OTHER INFORMATION: Oligonucleotide

<400> SEQUENCE: 103
gggggaaagg ctgctcataa                                                20

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide

<400> SEQUENCE: 104
taactggggg aagggacact                                                20

<210> SEQ ID NO 105
<211> LENGTH: 19
<212> TYPE: DNA
<213> ORGANISM: Artificial Sequence
<220> FEATURE:
<223> OTHER INFORMATION: Oligonucleotide

<400> SEQUENCE: 105
atggtgtcta agggcgaag                                                 19

<210> SEQ ID NO 106
<211> LENGTH: 22
<212> TYPE: DNA
<213> ORGANISM: Artificial Sequence
<220> FEATURE:
<223> OTHER INFORMATION: Oligonucleotide

<400> SEQUENCE: 106
ttacttgtac agctcgtcca tg                                             22

<210> SEQ ID NO 107
<211> LENGTH: 20
<212> TYPE: DNA
<213> ORGANISM: Artificial Sequence
<220> FEATURE:
<223> OTHER INFORMATION: Oligonucleotide

<400> SEQUENCE: 107
ttgatggagc caaagatgtg                                                20

<210> SEQ ID NO 108
<211> LENGTH: 20
<212> TYPE: DNA
<213> ORGANISM: Artificial Sequence
<220> FEATURE:
<223> OTHER INFORMATION: Oligonucleotide

<400> SEQUENCE: 108
```

```
gtacgtgttc cgtaagacgg                                              20

<210> SEQ ID NO 109
<211> LENGTH: 18
<212> TYPE: DNA
<213> ORGANISM: Artificial Sequence
<220> FEATURE:
<223> OTHER INFORMATION: Oligonucleotide

<400> SEQUENCE: 109
tgtttgacgg catcccac                                                18

<210> SEQ ID NO 110
<211> LENGTH: 20
<212> TYPE: DNA
<213> ORGANISM: Artificial Sequence
<220> FEATURE:
<223> OTHER INFORMATION: Oligonucleotide

<400> SEQUENCE: 110
ctgtcactgc ctggtacttc                                              20

<210> SEQ ID NO 111
<211> LENGTH: 21
<212> TYPE: DNA
<213> ORGANISM: Artificial Sequence
<220> FEATURE:
<223> OTHER INFORMATION: Oligonucleotide

<400> SEQUENCE: 111
ctgctggcca cattttatgt c                                            21

<210> SEQ ID NO 112
<211> LENGTH: 23
<212> TYPE: DNA
<213> ORGANISM: Artificial Sequence
<220> FEATURE:
<223> OTHER INFORMATION: Oligonucleotide

<400> SEQUENCE: 112
cttcagacgc acgaccttga ggg                                          23

<210> SEQ ID NO 113
<211> LENGTH: 19
<212> TYPE: DNA
<213> ORGANISM: Artificial Sequence
<220> FEATURE:
<223> OTHER INFORMATION: Oligonucleotide

<400> SEQUENCE: 113
gtcactgcct ggtacttcc                                               19

<210> SEQ ID NO 114
<211> LENGTH: 19
<212> TYPE: DNA
<213> ORGANISM: Artificial Sequence
<220> FEATURE:
<223> OTHER INFORMATION: Oligonucleotide

<400> SEQUENCE: 114
gtcactgcct ggtacttcc                                               19

<210> SEQ ID NO 115
<211> LENGTH: 21
<212> TYPE: DNA
<213> ORGANISM: Artificial Sequence
```

```
<220> FEATURE:
<223> OTHER INFORMATION: Oligonucleotide

<400> SEQUENCE: 115
gcagccctgc tactcatttt c                                              21

<210> SEQ ID NO 116
<211> LENGTH: 24
<212> TYPE: DNA
<213> ORGANISM: Artificial Sequence
<220> FEATURE:
<223> OTHER INFORMATION: Oligonucleotide

<400> SEQUENCE: 116
acgccccagg taagcaaact ttct                                           24

<210> SEQ ID NO 117
<211> LENGTH: 21
<212> TYPE: DNA
<213> ORGANISM: Artificial Sequence
<220> FEATURE:
<223> OTHER INFORMATION: Oligonucleotide

<400> SEQUENCE: 117
agtggaagat tgatggcagt g                                              21

<210> SEQ ID NO 118
<211> LENGTH: 21
<212> TYPE: DNA
<213> ORGANISM: Artificial Sequence
<220> FEATURE:
<223> OTHER INFORMATION: Oligonucleotide

<400> SEQUENCE: 118
ctgtctttgc tgtcctgatc a                                              21

<210> SEQ ID NO 119
<211> LENGTH: 20
<212> TYPE: DNA
<213> ORGANISM: Artificial Sequence
<220> FEATURE:
<223> OTHER INFORMATION: Oligonucleotide

<400> SEQUENCE: 119
ggtggatttc agggcaacta                                                20

<210> SEQ ID NO 120
<211> LENGTH: 25
<212> TYPE: DNA
<213> ORGANISM: Artificial Sequence
<220> FEATURE:
<223> OTHER INFORMATION: Oligonucleotide

<400> SEQUENCE: 120
acaaaatggc gtcctgaaca gttgg                                          25

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide

<400> SEQUENCE: 121
gatcatcagc aatgcctcct                                                20
```

```
<210> SEQ ID NO 122
<211> LENGTH: 22
<212> TYPE: DNA
<213> ORGANISM: Artificial Sequence
<220> FEATURE:
<223> OTHER INFORMATION: Oligonucleotide

<400> SEQUENCE: 122
gtcatgagtc cttccacgat ac                                              22

<210> SEQ ID NO 123
<211> LENGTH: 20
<212> TYPE: DNA
<213> ORGANISM: Artificial Sequence
<220> FEATURE:
<223> OTHER INFORMATION: Oligonucleotide

<400> SEQUENCE: 123
gtacatgaca aggtgcggct                                                 20

<210> SEQ ID NO 124
<211> LENGTH: 24
<212> TYPE: DNA
<213> ORGANISM: Artificial Sequence
<220> FEATURE:
<223> OTHER INFORMATION: Oligonucleotide

<400> SEQUENCE: 124
tggccaaggt catccatgac aact                                            24

<210> SEQ ID NO 125
<211> LENGTH: 23
<212> TYPE: DNA
<213> ORGANISM: Artificial Sequence
<220> FEATURE:
<223> OTHER INFORMATION: Oligonucleotide

<400> SEQUENCE: 125
caaatacaca gaggtcctca aga                                             23

<210> SEQ ID NO 126
<211> LENGTH: 21
<212> TYPE: DNA
<213> ORGANISM: Artificial Sequence
<220> FEATURE:
<223> OTHER INFORMATION: Oligonucleotide

<400> SEQUENCE: 126
cttcgccctt agacaccata g                                               21

<210> SEQ ID NO 127
<211> LENGTH: 21
<212> TYPE: DNA
<213> ORGANISM: Artificial Sequence
<220> FEATURE:
<223> OTHER INFORMATION: Oligonucleotide

<400> SEQUENCE: 127
ctgctggcca cattttatgt c                                               21

<210> SEQ ID NO 128
<211> LENGTH: 24
<212> TYPE: DNA
<213> ORGANISM: Artificial Sequence
<220> FEATURE:
<223> OTHER INFORMATION: Oligonucleotide
```

```
<400> SEQUENCE: 128
tggtcggaag cggagctact aact                                              24

<210> SEQ ID NO 129
<211> LENGTH: 19
<212> TYPE: DNA
<213> ORGANISM: Artificial Sequence
<220> FEATURE:
<223> OTHER INFORMATION: Oligonucleotide

<400> SEQUENCE: 129
tgcaagttca cagaggtcc                                                    19

<210> SEQ ID NO 130
<211> LENGTH: 21
<212> TYPE: DNA
<213> ORGANISM: Artificial Sequence
<220> FEATURE:
<223> OTHER INFORMATION: Oligonucleotide

<400> SEQUENCE: 130
cttcgccctt agacaccata g                                                 21

<210> SEQ ID NO 131
<211> LENGTH: 21
<212> TYPE: DNA
<213> ORGANISM: Artificial Sequence
<220> FEATURE:
<223> OTHER INFORMATION: Oligonucleotide

<400> SEQUENCE: 131
gcagccctgc tactcattt c                                                  21

<210> SEQ ID NO 132
<211> LENGTH: 26
<212> TYPE: DNA
<213> ORGANISM: Artificial Sequence
<220> FEATURE:
<223> OTHER INFORMATION: Oligonucleotide

<400> SEQUENCE: 132
agactaaaat tcgtcgctcc gcttcc                                            26

<210> SEQ ID NO 133
<211> LENGTH: 22
<212> TYPE: DNA
<213> ORGANISM: Artificial Sequence
<220> FEATURE:
<223> OTHER INFORMATION: Oligonucleotide

<400> SEQUENCE: 133
tcacaagaca tcaacttcac cc                                                22

<210> SEQ ID NO 134
<211> LENGTH: 19
<212> TYPE: DNA
<213> ORGANISM: Artificial Sequence
<220> FEATURE:
<223> OTHER INFORMATION: Oligonucleotide

<400> SEQUENCE: 134
tccacgtctc cagcctgct                                                    19

<210> SEQ ID NO 135
```

```
<210> SEQ ID NO 136
<211> LENGTH: 20
<212> TYPE: DNA
<213> ORGANISM: Artificial Sequence
<220> FEATURE:
<223> OTHER INFORMATION: Oligonucleotide

<400> SEQUENCE: 135
ggtggatttc agggcaacta                                              20

<210> SEQ ID NO 136
<211> LENGTH: 23
<212> TYPE: DNA
<213> ORGANISM: Artificial Sequence
<220> FEATURE:
<223> OTHER INFORMATION: Oligonucleotide

<400> SEQUENCE: 136
agctccgctt ccacactcat tcc                                          23

<210> SEQ ID NO 137
<211> LENGTH: 20
<212> TYPE: DNA
<213> ORGANISM: Artificial Sequence
<220> FEATURE:
<223> OTHER INFORMATION: Oligonucleotide

<400> SEQUENCE: 137
cgacgtcagc taggagtgtg                                              20

<210> SEQ ID NO 138
<211> LENGTH: 21
<212> TYPE: DNA
<213> ORGANISM: Artificial Sequence
<220> FEATURE:
<223> OTHER INFORMATION: Oligonucleotide

<400> SEQUENCE: 138
tgaaattggt ttgtgcctac c                                            21

<210> SEQ ID NO 139
<211> LENGTH: 18
<212> TYPE: DNA
<213> ORGANISM: Artificial Sequence
<220> FEATURE:
<223> OTHER INFORMATION: Oligonucleotide

<400> SEQUENCE: 139
ggccacctga tctgcaac                                                18

<210> SEQ ID NO 140
<211> LENGTH: 20
<212> TYPE: DNA
<213> ORGANISM: Artificial Sequence
<220> FEATURE:
<223> OTHER INFORMATION: Oligonucleotide

<400> SEQUENCE: 140
ttctgctgcc gtacatgaag                                              20

<210> SEQ ID NO 141
<211> LENGTH: 137
<212> TYPE: DNA
<213> ORGANISM: Artificial Sequence
<220> FEATURE:
<223> OTHER INFORMATION: Oligonucleotide

<400> SEQUENCE: 141
```

```
aggcagaaaa gaatgtggag aagaaaatct gcaagttcac agaggtcctc aagaccaacg      60
gactcctggt gggaagcgga gcgacgaatt ttagtctact aaaacaagcg ggtgatgtag     120
aagaaaaccc tggacct                                                    137

<210> SEQ ID NO 142
<211> LENGTH: 191
<212> TYPE: DNA
<213> ORGANISM: Artificial Sequence
<220> FEATURE:
<223> OTHER INFORMATION: Oligonucleotide

<400> SEQUENCE: 142
gacataacag ctatacctgt gaggccactc acaagacatc aacttcaccc attgtcaaga      60
gcttcaacag gaatgagtgt ggaagcggag ctactaactt cagcctgctg aagcaggctg     120
gagacgtgga ggagaaccct ggacctgcta gcatggtgag caagggcgag gaggataaca     180
tggcctctct c                                                         191

<210> SEQ ID NO 143
<211> LENGTH: 208
<212> TYPE: DNA
<213> ORGANISM: Artificial Sequence
<220> FEATURE:
<223> OTHER INFORMATION: Oligonucleotide

<400> SEQUENCE: 143
tacggaaaca ggccgagaag aacgtggaga agaaaattga caaatacaca gaggtcctca      60
agacccacgg actcctggtc ggaagcggag ctactaactt cagcctgctg aagcaggctg     120
gagacgtgga ggagaaccct ggacctatgg tgtctaaggg cgaagagctg attaaggaga     180
acatgcacat gaagctgtac atggaggg                                       208
```